(12) United States Patent
Spear et al.

(10) Patent No.: US 6,641,818 B1
(45) Date of Patent: Nov. 4, 2003

(54) CELLULAR PROTEINS WHICH MEDIATE HERPESVIRUS ENTRY

(75) Inventors: Patricia G. Spear, Chicago, IL (US); Morgyn S. Warner, Chicago, IL (US); Robert J. Geraghty, Lexington, KY (US); Wanda M. Martinez, Chicago, IL (US); Rebecca I. Montgomery, Hinsdale, IL (US); Gary H. Cohen, Havertown, PA (US); Roselyn J. Eisenberg, Haddonfield, NJ (US); Charles J. Whitbeck, Glenside, PA (US); Claude Krummenacher, Philadelphia, PA (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 09/723,368

(22) Filed: Nov. 28, 2000

Related U.S. Application Data

(63) Continuation of application No. PCT/US99/12235, filed on Jun. 2, 1999.
(60) Provisional application No. 60/087,862, filed on Jun. 3, 1998.

(51) Int. Cl.[7] ............... A61K 39/295; A61K 39/245; C12P 19/34
(52) U.S. Cl. ................ 424/204.1; 424/229.1; 435/41.1; 536/23.72; 530/300
(58) Field of Search ................ 424/204.1, 186.1, 424/229.1, 130.1; 435/69.1, 345, 91.1; 530/300, 350; 536/23.72

(56) References Cited

U.S. PATENT DOCUMENTS 6,469,155 B1 * 10/2002 Fume et al. ............... 536/23.5

OTHER PUBLICATIONS

Babic, et al., 1996, J. Gen. Virol. 77:2277–2285.
Barbas, 1995, Nature Medicine 1:837–839.
Buckmaster, et al., 1984, Virology 139:408–413.
Burton, et al., 1994, Adv. Immunol. 57:191–280.
Campadelli–Fiume, et al., 1988, J. Virol. 62:159–167.
Chadeneau, et al., 1994, J. Biol Chem. 269:15601–15605.
Chase, et al., Virology 194:365–369.
Chiang, et al., 1994, J. Virol. 68:2529–2543.
Cocchi, et al., 1998, J. Virol. 72:9992–10002.
Cocchi, et al., 1998, Proc. Natl. Acad. Sci. USA 95:15700–15705.
Cohen, 1993, Science 259:1691–1692.
Cohen, et al., 1980, J. Virol. 34:521–531.
Cohen, et al., 1984, J. Virol. 49:102–108.
Cohen, et al., 1986, J. Virol. 60:157–166.
Cranage, et al., 1986, EMBO J. 5:3057–3063.
Cunningham, et al., 1991, Science 254:821–825.
de Kruif, et al., 1995, J. Mol. Biol. 248:97–105.
Dean, et al., 1994, Virology, 199:67–80.
Dubin and Jiang, 1995, J. Virol. 69:4564–4568.
Eberle, et al., 1995, Gene 159:267–272.
Eisenberg, et al., 1982, J. Virol. 41:1099–1104.
Eisenberg, et al., 1987, Microb. Pathol. 3:423–435.
Ejercito, et al., 1968, J. Gen. Virol. 2:357–364.
Friedman, et al., 1984, Nature (London) 309:633–635.
Fynan, et al., 1993, Proc. Natl. Acad. Sci. 90:11478–11482.
Gilbert and Balaban–Malenbaum, 1980, Adv. in Neuroblastoma Res., 59–72.
Handler, et al., 1996, J. Virol. 70:6067–6075.
Ho and Mocarski, 1988, Virology 167:279–283.
Hoggan and Roizman, 1959, Amer. J. Hygiene 70:208–219.
Hsu, et al., 1997, J. Biol. Chem. 272:13471–13474.
Isola, et al., 1989, J. Virol. 63:2325–2334.
Izumi, et al., 1990, J. Exp. Med. 172:487–496.
Johnson and Ligas, 1988, J. Virol. 62:4605–4612.
Johnson, et al., 1990, J. Virol. 64:2569–2576.
Karger and Mettenleiter, 1993, Virology 194:654–664.
Kay, et al., 1997, Proc. Natl. Acad. Sci. USA 94:12744–12746.
Koike, et al., 1990, EMBO 9:3217–3224.
Koike, et al., 1992, J. Virol. 66:7059–7066.
Kuroda, et al., 1990, Virology 174:418–429.
Kwon, et al., 1997, J. Biol. Chem. 272;14272–14276.
Lee and Fuller, 1993, J. Virol. 67:5088–5097.
Lennon, et al., 1996, Genomics 33:151–152.
Liang, et al., 1991, J. Virol. 65:1124–1132.
Long, et al., 1992, J. Virol. 66:6668–6685.
Lopez, et al., 1997, In: *Identification of a New Class of Ig Superfamily Antigens Expressed in Hemopoiesis*, p.p. 1081–1083, Garland Publishing ed., N.Y.
Lopez, et al., 1995, Gene 155:261–265.
Marks, et al., 1991, J. Mol. Biol. 222:581–597.
Marsters, et al., 1997, J. Biol. Chem. 272:14029–14032.
Mauri, et al., 1998, Immunity 8:21–30.
Mendelsohn, et al., 1989, Cell 56:855–865.
Mettenleiter, 1995, In: Viral Vectors, 20:367–393.
Miller, et al., 1995, Am. J. Vet. Res. 56:870–874.
Mizukami, et al., 1998, Proc. Natl. Acad. Sci. USA 85:9273–9277.
Montgomery, et al., 1996, Cell 87:427–436.
Morrison and Racaniello, 1992, J. Virol. 66:2807–2813.
Muggeridge, et al., 1988, J. Virol. 62:3274–3280.
Munk and Donner, 1963, Arch. Gesamte Virus–forsch. 13:529–540.
Nicola, et al., 1996, J. Virol. 70:3815–3822; 46, 50, 53.

(List continued on next page.)

Primary Examiner—Ali R. Salimi
(74) Attorney, Agent, or Firm—Morgan, Lewis & Bockius, LLP

(57) ABSTRACT

A cellular herpesvirus entry protein, or a mutant, a homolog, a derivative, a variant or a biologically active fragment thereof, suspended in a pharmaceutically active carrier in an amount effective to inhibit entry of an alphaherpesvirus into a cell, wherein the cellular herpesvirus entry protein is a member of the immunoglobulin superfamily, is provided and method of use thereof

3 Claims, 49 Drawing Sheets

OTHER PUBLICATIONS

Nicola, et al., 1997, J. Virol. 71:2940–2946.
Nicola, et al., 1998, J. Virol. 72:3595–3601.
Nielsen, et al., 1991, Science 254:1497.
Peng, et al., 1998, J. Virol. 72:65–72.
Peterson, et al., 1968, Proc. Soc. Exper. Biol. & Med. 128:772–776.
Petrovskis, et al., 1988, J. Virol. 62:2196–2199.
Reilly, et al., 1997, Clin. Pharmacol. 32:313–323.
Rux, et al., 1996, J. Virol. 70:5455–5465.
Rux, et al., 1998, J. Virol. 72:7091–7098.
Seidel–Dugan, et al., 1988, J. Virol. 62:4027–4036.
Shieh, et al., 1992, J. Cell Biol. 116:1273–1281.
Showalter, et al., 1981, Infect. Immun. 34:684–692.
Sisk, et al., 1994, J. Virol. 68:766–775.
Sodora, et al., 1991, J. Virol. 65:4424–4431.
Spear, 1993, Sem. Virol. 4:167–180.
Tal–Singer, et al., 1994, Virology. 202:1050–1053.
Terhune, et al., 1998, J. Infect. Disease, 178:8–15.
Terry–Allison, et al., 1998, J. Virol. 72:5802–5810.
Tessier, et al., 1991, Gene. 98:177–183.
Thomas and Laimins, 1998, J. Virol. 72:1131–1137.
Whitbeck, et al., 1997, J. Virol. 71:6083–6093.
Willey, et al., 1996, Am. J. Respir. Cell. Mol. Biol. 14:262–271.
Willis, et al., 1998, J. Virol. 72:5937–5947.
Wolff, et al., 1991, Biotechniques 11:474–485.

* cited by examiner

Fig. 1A

```
   1  GAGCAGAACA GGGAGGCTAG AGCGCAGCGG GAACCGGCCC GGAGCCGGAG CCGGAGCCCC
  61  ACAGGCACCT ACTAAACCGC CCAGCCGATC GGCCCCCACA GAGTGGCCCG CGGGCCTCCG
 121  GCCGGGCCCA GTCCCCTCCC GGGCCCTTCA TGGCCCGGGC CGCTGCCCTC CTGCCGTCGA
 181  GATCGCCGCC GACGCCGCTG CTGTGGCCGC TGCTGCTGCT GCTGCTCCTG GAAACCGGAG
 241  CCCAGGATGT GCGAGTTCAA GTGCTACCCG AGGTGCGAGG CCAGCTCGGG GGCACCGTGG
 301  AGCTGCCGTG CCACCTGCTG CCACCTGTTC CTGGACTGTA CATCTCCCTG GTGACCTGGC
 361  AGCGCCCAGA TGCACCTGCG AACCACCAGA ATGTGGCCGC CTTCCACCCT AAGATGGGTC
 421  CCAGCTTCCC CAGCCCGAAG CCTGGCAGCG AGCGGCTGTC CTTCGTCTCT GCCAAGCAGA
 481  GCACTGGGCA AGACACAGAG GCAGAGCTCC AGGACGCCAC GCTGGCCCTC CACGGGCTCA
 541  CGGTGGAGGA CGAGGGCAAC TACACTTGCG AGTTTGCCAC CTTCCCCAAG GGGTCCGTCC
 601  GAGGGATGAC CTGGCTCAGA GTCATAGCCA AGCCCCAAGAA CCAAGCTGAG GCCCAGAAGG
 661  TCACGTTCAG CCAGGACCCT ACGACAGTGG CCCTCTGCAT CTCCAAAGAG GGCCGCCCAC
 721  CTGCCCCGGAT CTCCTGGCTC TCATCCCTGG ACTGGGAAGC CAAAGAGACT CAGGTGTCAG
 781  GGACCCTGGC CGGAACTGTC ACTGTCACCA GCCGCTTCAC CTTGGTGCCC TCGGGCCGAG
 841  CAGATGGTGT CACGGTCACC TGCAAAGTGG AGCATGAGAG CTTCGAGGAA CCAGCCCTGA
 901  TACCTGTGAC CCTCTCTGTA CGCTACCCTC CTGAAGTGTC CATCTCCGGC TATGATGACA
 961  ACTGGTACCT CGGCCGTACT GATGCCACCC CTGAGCTGTGA CGTCCGCAGC AACCCAGAGC
1021  CCACGGCTA TGACTGGAGC ACGACCTCAG GCACCTTCCC GACCTCCGCA GTGGCCCAGG
1081  GCTCCCAGCT GGTCATCCAC GCAGTGGACA GTCTGTTCAA TACCACCTTC GTCTGCACAG
1141  TCACCAATGC CGTGGGCATG GGCCGCGCTG AGCAGGTCAT CTTTGTCCGA GAAACCCCCA
```

```
1201  GGGCCTCGCC  CCGAGATGTG  GGCCCGCTGG  TGTGGGGGGC  CGTGGGGGGG  ACACTGCTGG
1261  TGCTGCTGCT  TCTGGCTGGG  GGGTCCTTGG  CCTTCATCCT  GCTGAGGGTG  AGGAGGAGGA
1321  GGAAGAGCCC  TGGAGGAGCA  GGAGGAGGAG  CCAGTGGCGA  CGGGGATTC   TACGATCCGA
1381  AAGCTCAGGT  GTTGGAAAT   GGGGACCCCG  TCTTCTGGAC  ACCAGTAGTC  CCTGTCCCA
1441  TGGAACCAGA  TGGCAAGGAT  GAGGAGGAGG  AGGAGGAGGA  AGAGAAGGCA  GAGAAAGCC
1501  TCATGTTGCC  TCCACCCCA   GCACTCGAGG  ATGACATGGA  GTCCCAGCTG  GACGGCTCCC
1561  TCATCTCACG  GCGGGCAGTT  TATGTGTGAC  CTGGACACAG  ACAGAGACAG  AGCCAGGCCC
1621  GGCCCTCCCG  CCCCCGACCT  GACCACGCCG  GCCTAGGGTT  CCAGACTGGT  TGGACTTGTT
1681  CGTCTGGACG  ACACTGGAGT  GGAACACTGC  CTCCCACTT   CTTGGGACTT  GGAGGAGGT
1741  GGAACAGCAC  ACTGGACTTC  TCCCGTCTCT  AGGGCTGCAT  GGGGAGCCCG  GGGAGCTGAG
1801  TAGTGGGGAT  CCAGAGAGGA  CCCCCGCCCC  CAGAGACTTG  GTTTGGCTC   CAGCCTTCCC
1861  CTGGCCCCGT  GACACTCAGG  AGTTAATAA   GAAACAAAA   GAAAACAAAA  AAAAAAAAAA
1921  AAAAAAA
```

Fig. 1B

```
MARAAALLPS RSPPTPLLWP LLLLLLLETG AQDVRVQVLP EVRGQLGGTV ELPCHLLPPV
PGLYISLVTW QRPDAPANHQ NVAAFHPKMG PSFPSPKPGS ERLSFVSAKQ STGQDTEAEL
QDATLALHGL TVEDEGNYTC EFATFPKGSV RGMTWLRVIA KPKNQAEAQK VTFSQDPTTV
ALCISKEGRP PARISWLSSL DWEAKETQVS GTLAGTVTVT SRFTLVPSGR ADGVTVTCKV
EHESFEEPAL IPVTLSVRYP PEVSISGYDD NWYLGRTDAT LSCDVRSNPE PTGYDWSTTS
GTFPTSAVAQ GSQLVIHAVD SLFNTTFVCT VTNAVGMGRA EQVIFVRETP RASPRDVGPL
VWGAVGGTLL VLLLLAGGSL AFILLRVRRR RKSPGGAGGG ASGDGGFYDP KAQVLGNGDP
VFWTPVVPGP MEPDGKDEEE EEEEEKAEKG LMLPPPPALE DDMESQLDGS LISRRAVYV
```

Fig. 1C

```
   1  CACCCAGCCC  ACCCCGCCCC  GGCCGACGGC  TGCAGCTGAC  CTGGATCCTT  CGAGCGCCCG
  61  CCGACCGCCA  GCGATCTTCC  CTCATCTTCC  GGGCTGGTTT  CTGCTGCGCG  AGGAGCGCTG
 121  CCCTCGCCGC  CCCTCTCGCC  GGACCCCCGG  CCCCCGATGG  CTCGGATGGG  GCTTGCGGGC
 181  GCCGCTGGAC  GCTGGTGGGG  ACTCGCTCTC  GGCTTGACCG  CATTCTTCCT  CCCAGGCGTC
 241  CACTCCCAGG  TGGTCCAGGT  GAACGACTCC  ATGTATGGCT  TCATCGGCAC  AGACGTGGTT
 301  CTGCACTGCA  GCTTTGCCAA  CCCGCTTCCC  AGCGTGAAGA  TCACCCAGGT  CACATGGCAG
 361  AAGTCCACCA  ATGGCTCCAA  GCAGAACGTG  GCCATCTACA  ACCCATCCAT  GGGCGTGTCC
 421  GTGCTGGCTC  CCTACCGCGA  GCGTGTGGAA  TTCCTGCGGC  CCTCCTTCAC  CGATGGCACT
 481  ATCCGCCTCT  CCCGCCTGGA  GCTGGAGGAT  GAGGGTGTCT  ACATCTGCGA  GTTTGCTACC
 541  TTCCCTACGG  GCAATCGAGA  AAGCCAGCTC  AATCTCACGG  TGATGGCCAA  ACCCACCAAT
 601  TGGATAGAGG  GTACCCAGGC  AGTGCTTCGA  GCCAAGAAGG  GGCAGGATGA  CAAGGTCCTG
 661  GTGGCCACCT  GCACCTCAGC  CAATGGGAAG  CCTCCCAGTG  TGGTATCCTG  GGAAACTCGG
 721  TTAAAAGGTG  AGGCAGAGTA  CCAGGAGATC  CGGAACCCCA  ATGGCACAGT  GACGGTCATC
 781  AGCCGCTACC  GCCTGGTGCC  CAGCAGGGAA  GCCCACCAGC  AGTCCCTTGC  CTGCATCGTC
 841  AACTACCACA  TGGACCGCTT  CAAGGAAAGC  CTCACTCTCA  ACGTGCAGTA  TGAGCCTGAG
 901  GTAACCATTG  AGGGGTTTGA  TGGCAACTGG  TACCTGCAGC  GGATGGACGT  GAAGCTCACC
 961  TGCAAAGCTG  ATGCTAACCC  CCCAGCCACT  GAGTACCACT  GGACCACGCT  AAATGGCTCT
1021  CTCCCCAAGG  GTGTGGAGGC  CCAGAACAGA  ACCCTCTTCT  TCAAGGGACC  CATCAACTAC
```

Fig. 2A

```
1081 AGCCTGGCAG GGACCTACAT CTGTGAGGCC ACCAACCCCA TCGGTACACG CTCAGGCCAG
1141 GTGGAGGTCA ATATCACAGA ATTCCCCTAC ACCCCGTCTC CTCCCGAACA TGGGCGGCGC
1201 GCCGGGCCGG TGCCCACGGC CATCATTGGG GGCGTGGCGG GGAGCATCCT GCTGGTGTTG
1261 ATTGTGGTCG GCGGGATCGT GGTCGCCCTG CGTCGCCGCC GGCACACCTT CAAGGGTGAC
1321 TACACAGCACCA AGAAGCACGT GTATGGCAAC GGCTACAGCA AGGCAGGCAT CCCCCAGCAC
1381 CACCCACCAA TGGCACAGAA CCTGCAGTAC CCCGACGACT CAGACGACGA GAAGAAGGCC
1441 GGCCCACTGG GTGGAAGCAG CTATGAGGAG GAGGAGGAGG AGGAGGAGGG CGGTGGAGGG
1501 GGCGAGCGCA AGGTGGGCGG CCCCCACCCC AAATATGACG AGGACGCCAA GCGGCCCTAC
1561 TTCACCGTGG ATGAGGCCGA GGCCCGTCAG GACGGGCTACG GGGACCGGAC TCTGGCTAC
1621 CAGTACGACC CTGAGCAGCT GGACTTGGCT GAGAACATGG TTTCTCAGAA CGACGGGTCT
1681 TTCATTTCCA AGAAGGAGTG GTACGTGTAG
```

Fig. 2B

MARMGLAGAA GRWWGLALGL TAFFLPGVHS QVVQVNDSMY GFIGTDVVLH CSFANPLPSV KITQVTWQKS
TNGSKQNVAI YNPSMGVSVL APYRERVEFL RPSFTDGTIR LSRLELEDEG VYICEFATFP TGNRESQLNL
TVMAKPTNWI EGTQAVLRAK KGQDDKVLVA TCTSANGKPP SVVSWETRLK GEAEYQEIRN PNGTVTVISR
YRLVPSREAH QQSLACIVNY HMDRFKESLT LNVQYEPEVT IEGFDGNWYL QRMDVKLTCK ADANPPATEY
HWTTLNGSLP KGVEAQNRTL FFKGPINYSL AGTYICEATN PIGTRSGQVE VNITEFPYTP SPPEHGRRAG
PVPTAIIGGV AGSILLVLIV VGGIVVALRR RRHTFKGDYS TKKHVYGNGY SKAGIPQHHP PMAQNLQYPD
DSDDEKKAGP LGGSSYEEEE EEEGGGGGE RKVGGPHPKY DEDAKRPYFT VDEAEARQDG YGDRTLGYQY
DPEQLDLAEN MVSQNDGSFI SKKEWYV

Fig. 2C

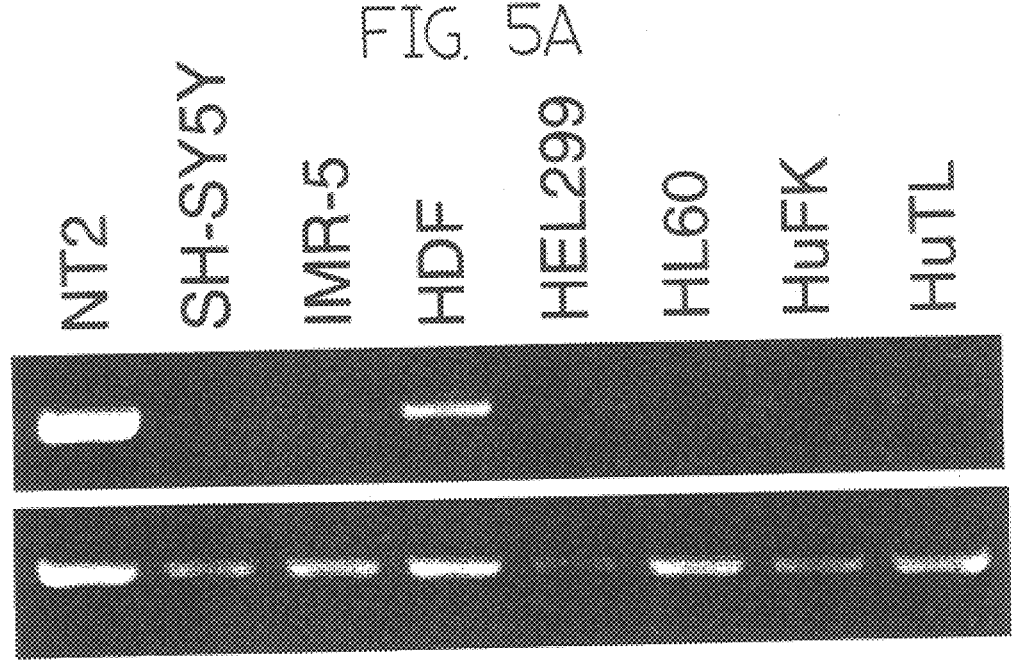

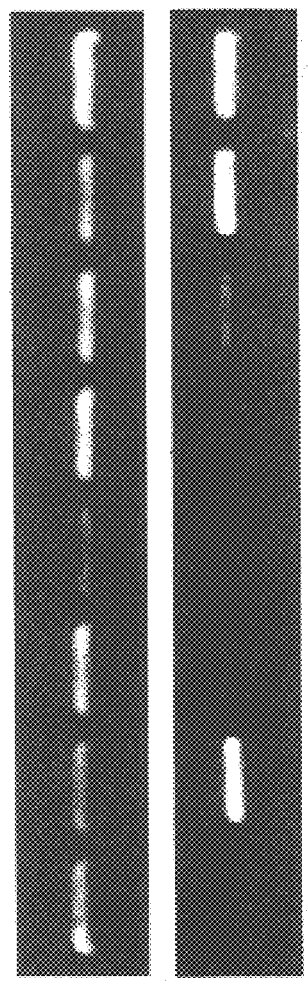
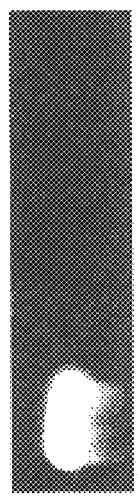
FIG. 10C  
FIG. 10B  
FIG. 10A

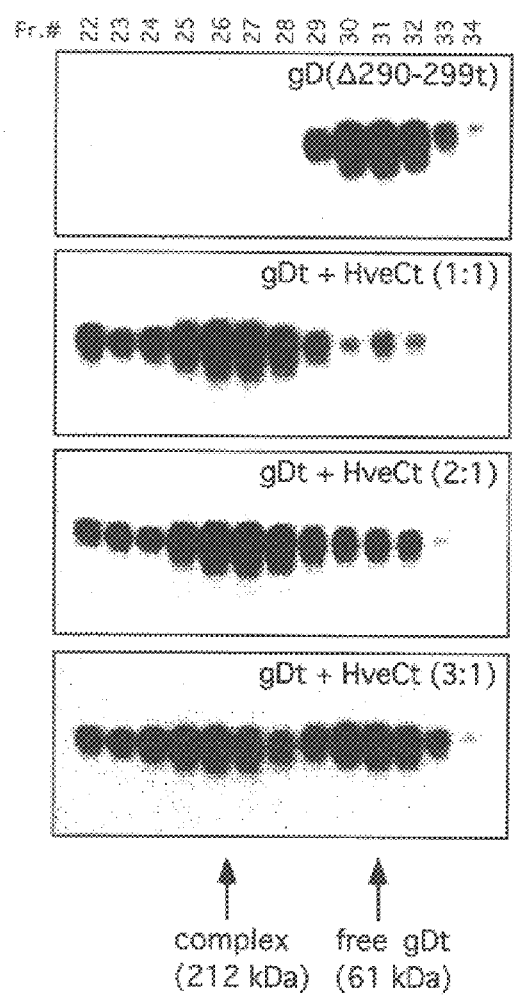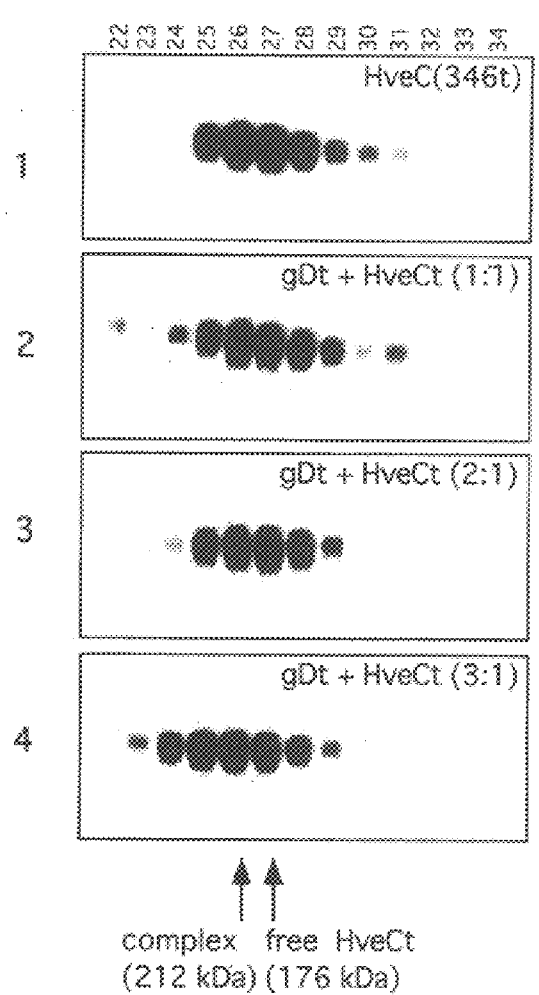

ed on Jun. 3, 1998.

CELLULAR PROTEINS WHICH MEDIATE HERPESVIRUS ENTRY

CROSS-REFERENCE TO RELATED APPLICATIONS

This application is a continuation of International Patent Application PCT/US99/12235, filed Jun. 2, 1999.

This application is entitled to priority pursuant to 35 U.S.C. § 119(e) to U.S. Provisional Patent Application No. 60/087,862, which was filed on Jun. 3, 1998.

STATEMENT REGARDING FEDERALLY SUPPORTED RESEARCH OR DEVELOPMENT

This research was supported in part by U.S. Government NIH Grant No. AI136293, and the U.S. Government may therefore have certain rights in the invention.

FIELD OF THE INVENTION

The field of the invention is cellular proteins which mediate entry of viruses into cells.

BACKGROUND OF THE INVENTION

Herpesviruses are ubiquitous viruses which are the causative agents of numerous diseases in both humans and animals. These viruses are enveloped double stranded icosahedral DNA containing viruses, which envelope is acquired by budding of the nucleocapsid through the inner nuclear membrane. Members of the herpesvirus family that are important human pathogens include herpes simplex virus type 1 (HSV-1), herpes simplex virus type 2 (HSV-2), varicella zoster virus (VZV), Epstein Barr virus (EBV), cytomegalovirus (CMV), and human herpesviruses type 6, type 7 and type 8 (HHV-6, HHV-7 and HHV-8).

A key feature of viral infection of cells is the binding of one or more viral proteins with one or more cellular proteins expressed on the surface of a cell, which binding results in entry of the virus into the cell. Members of the alphaherpesvinrs subfamily of the herpesviruses typically have a broad host range and a short replicative cycle, are highly cytotoxic to cultured cells, and can establish latent infections in cells of the nervous system of the natural host (Roizman, 1993, The family herpesviridae. In: The Human Herpesviruses (Roizman, Whitley and Lopez, Eds.), pp. 1–9. Raven Press Ltd., New York). Human and animal representatives of the alphaherpesvirus subfamily exhibit common requirements for entry into cells (Mettenleiter, 1995, Molecular properties of alphaherpesviruses used in transneuronal pathway tracing. In: Viral Vectors, pp. 367–393. Academic Press, Inc; Spear, 1993, Sem. Virol. 4:167–180). In most cases, five viral envelope glycoproteins (gB, gC, gD, gH and gL) mediate virus binding to cells and entry therein. The initial interaction of virus with cells is binding of gC, and in some cases also gB, to cell surface glycosaminoglycans (GAGs), and preferentially to heparan sulfate. Although gC is dispensable for the infection of many cultured cells, gB, gD, gH arid gL are required for mediating the fusion between the virion envelope and the cell membrane that allows viral penetration. Various lines of evidence point to the interaction of some of these envelope glycoproteins, particularly gD, with cell surface receptors other than heparan sulfate and to competition among alphaherpesviruses for binding to gD receptors (Campadelli-Fiume et al., 1988, J. Virol. 62:159–167; Chase et al., 1993, Virology 194:365–369; Johnson et al., 1990, J. Virol. 64:2569–2576; Johnson and Ligas, 1988, J. Virol. 62:4605–4612; Karger and Mettenleiter, 1993, Virology 194:654–664; Lee and Fuller, 1993, J. Virol. 67:5088–5097; Liang et al., 1991, J. Virol. 65:1124–1132; Petrovskis et al., 1988, J. Virol. 62:2196–2199).

An expression cloning assay has been devised for isolating plasmids encoding cell surface proteins that can mediate herpes simplex virus type 1 (HSV-1) entry (Montgomery et al., 1996, Cell 87:427–436). This assay relies on the use of Chinese hamster ovary (CHO) cells, which express GAGs required for virus binding to cells but are resistant to the entry of certain HSV-1 strains such as HSV-1 (KOS) (Shieh et al., 1992, J. Cell Biol. 116:1273–1281). Expression libraries, or sub-divisions of the libraries, that contain plasmids capable of conferring susceptibility to HSV-1(KOS) can be identified by transfecting the CHO cells and then assaying for infection with a recombinant HSV-1(KOS) expressing a reporter gene.

A cell surface protein having herpesvirus entry activity was identified using the aforementioned assay. This cell surface protein is a previously undescribed member of the human TNF receptor family, which was originally named herpesvirus entry mediator (HVEM) and is designated herein as herpesvirus entry protein A (HveA). HveA is disclosed in U.S. application Ser. No. 08/509,024, filed on Jul. 28, 1995, which is hereby incorporated herein by reference in its entirety. HveA is a type I membrane glycoprotein with cysteine-rich repeats in the ectodomain that are characteristic of the TNF receptor family (Montgomery et al., 1996, Cell 87 :427) and with a cytoplasmic domain that can interact with members of the TRAF family of signaling molecules (Hsu et al., 1997, J. Biol. Chem. 272:13471–13474; Marsters et al., 1997, J. Biol. Chem. 272:14029–14032). HveA is a receptor for two members of the TNF family, lymphotoxin a and LIGHT (Mauri et al., 1998, Immunity 8:21–30). HveA also binds to isolated HSV-1 or HSV-2 gD and to gD in virions (Nicola et al., 1998, J. Virol. 72:3595–3601; Whitbeck et al., 1997, J. Virol. 71:6083–6093).

HveA is expressed in many fetal and adult human tissues, including lung, liver and kidney (Montgomery et al., 1996, Cell 87:427), but appears to be most abundantly expressed in lymphoid organs and cells (Hsu et al., 1997, J. Biol. Chem. 272:13471–13474; Kwon et al., 1997, J. Biol. Chem. 272:14272–14276; Marsters et al., 1997, J. Biol. Chem. 272:14029–14032). The use of anti-HveA antibodies that blocked HSV entry established that HveA serves as the principal co-receptor for entry of HSV-1(KOS) into activated human T lymphocytes (Montgomery et al., 1996, Cell 87:427). However, the antibodies did not protect a number of other human cell types from infection, indicating that there are other co-receptors for HSV entry.

Another indication for the existence of multiple independent co-receptors for HSV entry was the finding that, although HveA expression in CHO cells enhanced the entry of all wild-type HSV-1 and HSV-2 strains tested, HveA failed to mediate the entry of three mutant HSV-1strains (Montgomery et al., 1996, Cell 87:427). Two of these strains, designated HSV-1(KOS)Rid1 and HSV-1(KOS) Rid2 and abbreviated herein as KOS-Rid1 and KOS-Rid2, are viable mutants which were selected for theft ability to overcome interference with viral entry imposed by the expression of wild-type HSV-1 gD in cells (Dean et al., 1994, Virology 199:67–80). The third strain, HSV-1(ANG), was isolated from a clinical specimen (Munk and Donner, 1963, Arch. Gesamte Virus-forsch. 13:529–540) under conditions that would be expected to inhibit the replication of wild-type HSV (under an overlay of agar containing inhibitory sulfated polysaccharides) and perhaps select for viral variants. This strain proved to be as resistant to gD-mediated interference as KOS-Rid1 and KOS-Rid2 (Dean et al., 1994, Virology 199, 67–80). All three strains have amino acid substitutions, in gD at position 27 (Q27P or Q27R), that are sufficient to confer the mutant phenotype of resistance to gD-mediated interference. Consistent with the failure of the mutant strains to use HveA for entry, the mutant forms of gD failed to bind HveA whereas wild-type forms of HSV-1 and HSV-2 gD were able to bind HveA (Whitbeck et al., 1997, J. Virol. 71 :6083–6093). Because the mutant HSV-1 strains can infect a number of human or other cell types, despite failure to use HveA for entry, other co-receptors for entry must be expressed in these cells.

Currently, there are no fully effective treatments for herpesvirus infection of humans, which infections are of ten severe, and sometimes even fatal. Clearly, the identification of compounds which inhibit entry of herpesvirus into cells would greatly facilitate treatment of herpesviruses in humans. To date, there are no commercially available compounds which are approved for treatment of herpesvirus infection, which compounds inhibit entry of virus into cells. Thus, there is a long felt need for the identification of and methods of use of such compounds. The present invention satisfies this need.

SUMMARY OF THE INVENTION

The invention relates to a cellular herpesvirus entry protein, or a mutant, a homolog, a derivative, a variant or a biologically active fragment thereof, suspended in a pharmaceutically active carrier in an amount effective to inhibit entry of an alphaherpesvirus into a cell, wherein the cellular herpesvirus entry protein is a member of the immunoglobulin superfamily.

In one aspect, the cellular herpesvirus entry protein is selected from the group consisting of HveB and HveC.

In another aspect, the alphaherpesvirus is selected from the group consisting of HSV-1, HSV-2, and the animal viruses, pseudorabies virus (PRV) and bovine herpesvirus 1 (BHV-1).

The invention also relates to a recombinant cell comprising an isolated nucleic acid encoding a cellular herpesvirus entry protein, or a mutant, cL homolog, a derivative, a variant or a biologically active fragment thereof, wherein the cellular herpesvirus entry protein is a member of the immunoglobulin superfamily and the herpesvirus is an alphaherpesvirus.

In one aspect, cellular herpesvirus entry protein is selected from the group consisting of HveB and HveC.

In another aspect, the alphaherpesvirus is selected from the group consisting of HSV-1, HSV-2, PRV and BHV-1.

In yet another aspect, the cell is selected from the group consisting of Chinese hamster ovary cells, murine melanoma cells, and swine testes cells.

Also included in the invention is a vector comprising an isolated nucleic acid encoding a cellular herpesvirus entry protein, or a mutant, a homolog, a derivative, a variant or a biologically active fragment thereof, wherein the cellular herpesvirus entry protein is a member of the immunoglobulin superfamily and the herpesvirus is an alphaherpesvirus.

In one aspect, the cellular herpesvirus entry protein is selected from the group consisting of HveB and HveC.

In another aspect, the alphaherpesvirus is selected from the group consisting of HSV-1, HSV-2, PRV and BHV-1.

The invention further relates to an anti-cellular herpesvirus protein compound, wherein the compound binds herpesvirus glycoprotein D.

In one aspect, the cellular herpesvirus entry protein is selected from the group consisting of HveB and HveC.

In another aspect, the herpesvirus is selected from the group consisting of HSV-1, HSV-2, PRV and BHV-1.

The invention additionally relates to an anti-cellular herpesvirus protein compound, wherein the compound is selected from the group consisting of an antisense oligonucleotide, an antibody specific for the cellular herpesvirus protein, a peptide and a peptidomimetic.

Also included in the invention is a method of identifying a compound capable of inhibiting entry of an alphaherpesvirus into a cell. The method comprises providing a population of cells which express a cellular herpesvirus entry protein, wherein the cellular herpesvirus entry protein is a member of the immunoglobulin superfamily, infecting the cells in the presence or absence of a test compound, and measuring the level of entry of an alphaherpesvirus into the cells, wherein a lower level of entry of the virus into the cells in the presence of the test compound compared with the level of entry of the virus into the cells in the absence of the test compound is an indication that the test compound is an anti-cellular herpesvirus entry protein compound.

The invention also includes an anti-cellular herpesvirus entry protein compound identified by the method of identifying a compound capable of inhibiting entry of an alphaherpesvirus into a cell. The method comprises providing a population of cells which express a cellular herpesvirus entry protein, wherein the cellular herpesvirus entry protein is a member of the immunoglobulin superfamily, infecting the cells in the presence or absence of a test compound, and measuring the level of entry of an alphaherpesvirus into the cells, wherein a lower level of entry of the virus into the cells in the presence of the test compound compared with the level of entry of the virus into the cells in the absence of the test compound is an indication that the test compound is an anti-cellular herpesvirus entry protein compound.

The invention also relates to a method of inhibiting entry of an alphaherpesvirus into a cell comprising adding to the cell an anti-cellular herpesvirus entry protein compound thereby inhibiting entry of the virus into the cell.

In addition, the invention relates to a method of treating an alphaherpesvirus infection in an animal comprising administering to the animal an anticellular herpesvirus entry protein compound, wherein the cellular herpesvirus entry protein is a member of the immunoglobulin superfamily.

In one aspect, the animal is a human.

In another aspect, the herpesvirus is selected from the group consisting of HSV-1 and HSV-2.

The invention further relates to a composition comprising a soluble alphaherpesvirus glycoprotein D-binding cellular herpesvirus entry protein.

In one aspect, the cellular herpesvirus entry protein is selected from the group consisting of HveB and HveC. In a preferred embodiment, the .HveB and the HveC are truncated.

BRIEF DESCRIPTION OF THE DRAWINGS

FIG. 1, comprising FIGS. 1A, 1B, and 1C, is the nucleotide sequence (FIGS. 1A and 1B; SEQ ID NO:1) and corresponding amino acid sequence (FIG. 1C; SEQ ID NO:2) of HveB.

FIG. 2, comprising FIGS. 2A, 2B, and 2C, is the nucleotide sequence (FIGS. 2A and 2B; SEQ ID NO:3) and corresponding amino acid sequence (FIG. 2C; SEQ ID NO:4) of HveC.

FIG. 4, comprising In FIG. 4A, the cells were CHO-IEβ8/HveB (hatched bar) and CHO-IEβ8 (open bar) while in FIG. 4B, the cells were CHO-K1 transiently transfected with HveB-expressing pMW2O (hatched bars) or empty vector pcDNA3 (open bars). After 6 hours, the cells were permeabilized and incubated with ONPG substrate for quantitation of β-galactosidase activity. The results depicted how entry of virus at a single input dose in the linear range of the dose-response curve for each virus ($3 \times 10^4$ PFU/well for both HSV-2 strains, $10^7$ PFU/well for BHV-1 and PRV).

FIG. 5, FIGS. 5A, 5B, and 5C, is a series of images of gels depicting expression of HveB mRNA in various cell types. Total RNA was isolated from the cells indicated, cDNAs were produced and PCR was performed using primers specific for HveB m-RNA (FIG. 5A and 5C) or -actin mRNA (FIG. 5B). The products were separated by electrophoresis on an agarose gel and then stained with ethidium bromide. Human cells passaged only a limited number of times in culture included diploid fibroblasts (HDF), embryonic lung fibroblasts (HEL299), foreskin keratinocytes (HuFK) and T lymphoblasts (HuTL). Human cell lines included teratocarcinoma (NT2), neuroblastoma (SH-SY5Y and IMR-5) and promyelocytic leukemia (HL60). Also shown are results obtained using RNA extracted from control CHO-K1 cells and stable transfectants expressing HveA, HveB or HveC (FIG. 5C). The β-actin controls in FIG. 5B are also presented herein in Example 2 wherein expression of HveC mRNA is apparent in the aforementioned cell types.

FIG. 6, FIGS. 6A and 6B, is a pair of graphs depicting susceptibility of HveB-expressing CHO cells (FIG. 6A) and HEL299 cells (FIG. 6B) to KOS-gD6 complemented with KOS-Rid1 gD (circles) but not with KOS gD (triangles). The cells in 96-well plates were inoculated with virus at the indicated input doses and 6 hours later, the cells were permeabilized and ONPG substrate was added for quantitation of β-galactosidase activity.

FIG. 7, comprising

FIG. 9, FIGS. 9A, 9B, 9C, and 9D, is a series of graphs which depict enhanced entry of BHV-1(FIG. 9A), HSV-1 (FIG. 9B), PRV (FIG. 9C), and HSV-1-Rid1 (FIG. 9D), into HveC- and Pvr-HveD-expressing CHO cells. Subconfluent CHO-IEβ8 cells (Montgomery et al., 1996, Cell 87:427) were transfected with plasmids expressing HveA (pBec10) (Montgomery et al., 1996, Cell 87:427), HveC (pBG38), Pvr-HveD (pBG42.16), or control DNA (pcDNA3). Twenty four hours later, the transfected cells were replated in 96-well plates (approximately $2-4 \times 10^4$ per well), and the next day the cells were exposed to HSV-1(KOS), HSV-1 (KOS)Rid1, PRV(Kaplan), or BHV-1(Cooper) isolates expressing β-galactosidase as described herein. Six hours after inoculation, the cells were lysed and β-galactosidase activity determined as a measure of virus entry also as described herein. The infections were performed in triplicate, repeated four times, and the mean values plus standard deviations for a representative experiment are depicted. PFU (plaque forming units). In these figures, diamonds correspond to data relating to HveA; circles correspond to data relating to HveC; triangles correspond to data relating to HveD; and squares correspond to data relating to the control.

FIG. 10, comprising FIGS. 10A, 10B, and 10C, is a series of images of gels depicting expression of HveC mRNA. Total RNA was isolated from established cell lines and primary cells, cDNA was obtained, and PCR was performed as described herein. FIG. 10A depicts HveC mRNA expression in CHO lines stably expressing HveA (HveA-12), HveB (HveB-1), or HveC (HveC-1) and also the parental CHO cell line (K1). FIG. 10B depicts HveC mRNA expression in human cell lines described herein and primary cell cultures: HDF (human diploid fibroblasts); HuFK (human foreskin keratinocytes); HuTL (phytohemagglutinin-activated human T-cell blasts). FIG. 10C depicts M-actin mRNA expression detected in the RNA samples from corresponding lanes in FIG. 10B. The β-actin control results are also presented in a figure demonstrating HveB expression in these same cell lines (see Example 1).

FIG. 11, comprising

FIG. 13, comprising FIG. 13A is an image of a silver stained gel of HveCt after nickel chromatography purification and SDS PAGE under denaturing and reducing conditions. The size of the molecular weight markers (M) is indicated in kilodaltons. FIG. 13B is an image of Western blot wherein proteins separated on an SDS-PAGE gel run under in denaturing and reducing conditions were transferred to nitrocellulose and were detected with R145 antipeptide serum. Lane 1 and 3: purified HveCt used as mock-digested controls. In lane 2, N-1 inked carbohydrates of the purified protein were digested by glycopeptidase F and in lane 4, purified HveCt was treated with endoglycosidase H. FIG. 13C is a graph of mass spectrometry analysis of purified HveCt. Calculated mass of singly charged species is indicated in kDa. FIG. 13D is a graph depicting purified HveCt (24 mM in PBS) which was loaded on a Superdex 200 size exclusion column and eluted with PBS. The elution profile monitored by absorbance at 280 nm is shown. Calculated size- is based on positions of molecular size standards, indicated in kDa.

FIG. 15, comprising FIG. 15A depicts glycoproteins bound to immobilized HveC which were detected with specific antibodies (R7 for gD, R147 for gC, R69 for gB and R137 for gH/gL) followed by peroxidase conjugated secondary antibody and substrate. FIG. 15B depicts gD-1(306t) from strain KOS and gD-2 (306t) from strain 333 at various concentrations which were incubated on HveCt coated plates. FIG. 15C depicts mutant gD(QAAt) lacking N-CHO compared with the glycosylated control gD(306t) for binding to immobilized HveCt. FIG. 15D depicts purified gD-1(306t) which was reduced and alkylated prior to incubation on the HveCt coated plate. Rabbit R7 polyclonal serum was used to detect any type of gD.

FIG. 16, comprising FIG. 16A depicts glycoprotein D from both HSV(ANG) and HSV (rid1) which were expressed in baculovirus as truncated forms and affinity purified. Cysteine residues on gD(306t) from KOS wild type strain as well as mutated residues are indicated. The hatched box represent the mellitin signal peptide and the black lollipops represent N-linked carbohydrates. gD from these strains were compared to gD (KOS) for binding to immobilized HveAt (B) or HveCt (C). The procedure previously described was used to detect bound gD in these ELISA.

FIG. 17, comprising FIG. 17A-1 to 17A-3, 17B-1 to 17B-3, 17C-1 to 17C-3, and 17D-1 to 17D-3, depicts the effects of linker insertions in functional regions of gD on binding to HveCt (FIGS. 17A-3, 17B-3, 17C-3 and 17D-3) and HveAt (FIGS. 17A-2, 17B-2, 17C-2 and 17D-2. ELISA plates were saturated with HveAt or HveCt and were incubated with various concentrations of purified mutant gDs. Binding of each mutant is compared to binding of wild type gD(306t) (black squares). gD(-34t) is mutated in functional region I (FIG. 17A-1), gD(-126t) in region II (FIG. 17B-1), gD(-243t) in region III (FIG. 17C-1) and gD(Δ290–299) in functional region IV (FIG. 17D-1). Position of the linker insertion is schematically represented for each mutant. R7 antiserum was used to detect bound gD.

FIG. 18, comprising FIG. 18A depicts shorter versions of gD-1 KOS which were produced in the baculovirus expression system, purified and tested for binding to HveC. FIG. 18B is a graph depicting an ELISA assay which was performed with HveCt bound to the plate and incubated with variable amounts of gD. Bound gD was detected with R7 antiserum.

FIG. 19, comprising FIG. 19A depicts purified HSV-1 KOS virions ($10^7$ PFU) which were incubated at 4° C. for 2 hours with (lane 2) or without (lane 1) HveCt (150 μg) and then were loaded onto a sucrose gradient. The viral band was collected and analyzed by SDS-PAGE and Western blotting. Membranes were probed for the presence of VP5 and HveCt (R154 serum). In blocking experiments, virions were preincubated with cocktails of antibodies specific for HSV glycoproteins. The antibodies were: for gB: 5510(0.5 μl ascites), DL16(5 μg IgG), DL21(5 μg IgG) and R69(0.5 μl serum) (lane 3); for gC: MP1 (0.5 μl ascites), MP5 (5 μg IgG), 1C8(5 μg IgG) and R46(0.5 μl serum) (lane 4); for gD: 1D3(0.5 μl ascites), DL2(5 μg IgG), DL11 (5 μg IgG) and R7(0.5 μl serum) (lane 5) or for gH/gL: LP11 (0.5 μl ascites), 53S (5 μg IgG), H6(5 μg IgG) and R137(0.5 μserum) (lane 6). Rabbit Ig heavy chain is detected by goat anti-rabbit secondary Ab and is indicated on this blot with a white arrow. FIG. 19B illustrates prior to cosedimentation with HveCt, purified HSV-1 KOS virions ($10^7$ PFU) which were preincubated with 50 µg of monoclonal IgGs:. HD1 (group Ia), DL11(group Ib), DL6(group II), DL2(group VI) or 1D3(group VII) during 1 hour at 37° C. Untreated control is-shown in lane 1.

FIG. 20, comprising FIGS. 20A and 20B, is a series of images presented in panels depicting gel filtration chromatography of the HveC-gD) complex. Purified HveCt and gD(Δ290–299t) were loaded independently or mixed at the indicated ratio on a Superdex 200 column. Elution was performed with PBS and monitored by measuring UV absorption at 280 nm. Fractions of 0.5 ml were collected and analyzed by SDS PAGE in denaturing and reducing conditions. After protein transfer, the blots were probed with R7 serum to detect gD (FIG. 20A) or R145 serum to detect HveC (FIG. 20B). The size of complexes were calculated according to elution of standards used to calibrate the column. Purified HveCt (FIG. 20B, panel 1) or gD(Δ290–299t) (FIG. 20A, panel 1) were diluted in PBS to 20 mM in PBS and loaded on the column. Panel 2 of FIGS. 20A and 20B depict protein elution from a column loaded with gD(Δ290–299t) (20 mM) and HveCt (20 mM) premixed overnight at 4° C. in PBS. The initial molar ratio of gDt monomer to HveCt monomer is 1:1. Panel :3 of FIGS. 20A and 20B depict protein elution from a column loaded with gD(Δ290–299t) (20 mM) and HveCt (10 mM) mixed overnight at 4° C. in PBS. The initial molar ratio of gD to HveC is 2:1. Panel 4 of FIGS. 20A and 20B depict protein elution from a column loaded with gD(Δ290–299t) (30 µM) and HveCt (10 µM) mixed overnight at 4° C. in PBS. The initial molar ratio of gD to HveC was 3:1.

FIG. 21, comprising

FIG. 22, comprising FIG. 22A depicts purified proteins which were electrophoresed on a 12% polyacrylamide gel under reducing and denaturing conditions and visualized by silver staining. The molecular weight markers are indicated in kilodaitons (kDa). FIG. 22B illustrates endoglycosidase digestions: HveC(245t) (lanes 1–4) and HveC(143t) (lanes 5–8) were subjected to digestion with PNGase F (F) or endoglycosidase H (H) or were mock treated (−) prior to electrophoresis on a 16% acrylamide gel under reducing and denaturing conditions. After Western blotting, proteins were detected with the anti tetra-His MAb. FIG. 22C depicts a native western blot. Proteins were run under non-denaturing and non-reducing condition on a 12% polyacrylamide gel and detected with MAb R1.302.

FIG. 23, comprising FIG. 23A) or R1.302 Ig (Beckman/Coulter; FIG. 23B). Bound immunoglobulins were detected with HRP-conjugated anti-mouse IgG secondary Ab and substrate. Absorbance was read at 405 nm.

FIG. 24, comprising

FIG. 25, comprising

FIG. 26, comprising

FIG. 27, comprising

FIG. 29, comprising

FIG. 32, comprising

FIG. 33, comprising

DETAILED DESCRIPTION OF THE INVENTION

Figure 3:
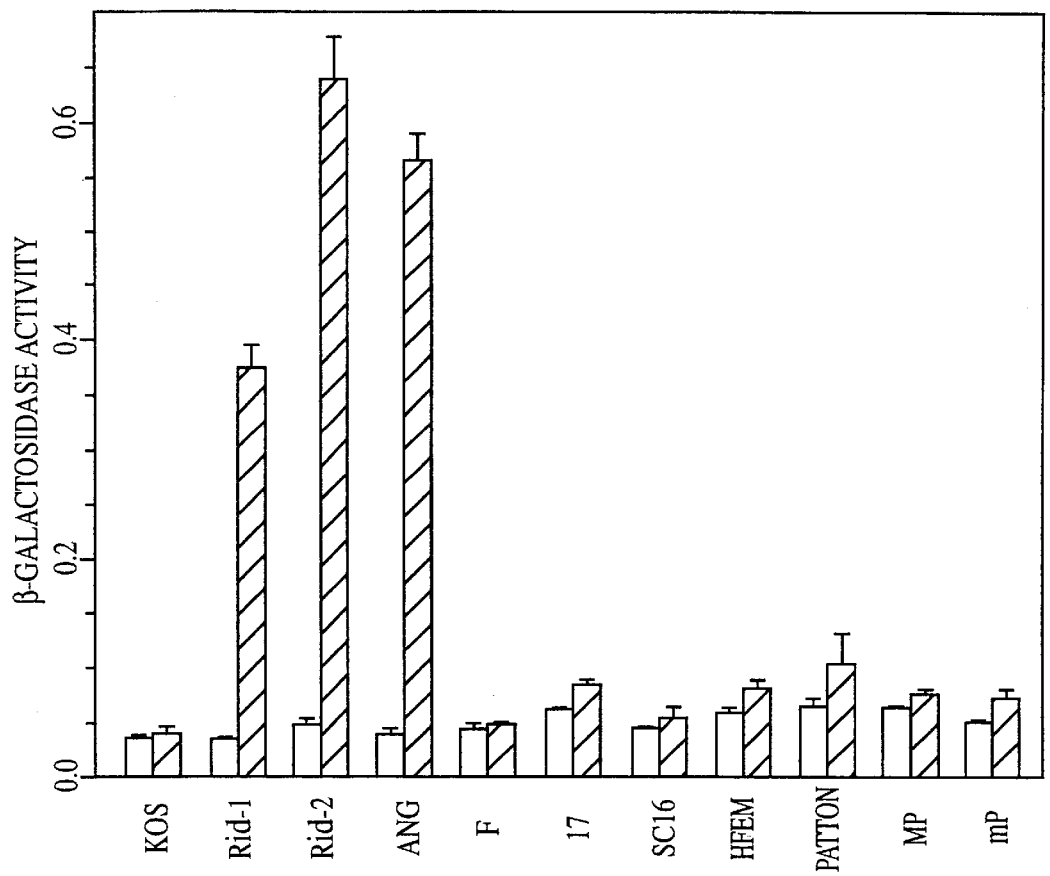
FIG. 3 is a histogram depicting the susceptibility of HveB-expressing CHO cells to entry of various HSV-1 strains. CHO-1EDβ8 cells which express β-galactosidase upon entry of HSV-1 or HSV-2, were transfected with HveB-expressing pMW347 (hatched bars) or empty vector pcDNA3 (open bars). The cells were then plated in 96-well plates and were inoculated with serial dilutions of the indicated viruses. After 6 hours, the cells were permeabilized and incubated with ONPG substrate for quantitation of β-galactosidase activity as described in the text. The results depicted show entry of virus at a single input dose of $7.5 \times 10^4$ PFU per well in the linear range of the dose-response curve for each virus. The error bars indicate standard deviation of triplicate determinations.

The present invention is based upon the discovery of two cellular proteins, HveB and HveC, which are cellular herpesvirus entry proteins and therefore mediate entry of HSV-1 and/or HSV-2 and other herpesviruses into cells. The identification of these proteins facilitates the identification of compounds which serve to inhibit entry of herpesviruses into cells.

HveB and HveC are collectively referred to herein as cellular herpesvirus entry proteins. The nucleotide and corresponding amino acid sequence of HveB and HveC are presented herein in FIGS. 1 and 2, respectively.

The present invention includes a method of screening compounds for their ability to inhibit HveB or HveC mediatedherpesvirus entry into cells. The present invention further includes a compound which is identified using the method of the invention, which compound inhibits herpesvirus entry into cells.

A compound which inhibits HveB or HveC mediated herpesvirus entry into a cell is referred to herein as an "anti-cellular herpesvims entry protein" compound.

In addition, the invention includes a method of inhibiting the entry of a herpesvirus into a cell. The invention further includes a method of treating a herpesvirus infection in a human by administering to the human a compound capable of inhibiting entry of a herpesvirus into a cell.

The cellular proteins, HveB and HveC, which have been discovered according to the present invention to inhibit entry of herpesviruses into cells, are human members of the immunoglobulin superfamily of proteins. HveC is a cellular protein which has been discovered in the present invention to mediate entry of HSV-1, HSV-2, porcine pseudorabiesvirus (PRV) and bovine herpesvirus I (BHV-1) into cells. HveC is a membrane glycoprotein which is highly homologous to the poliovirus receptor related protein 1 (Prr1). As the data presented herein establish, soluble forms of HveC interact directly with the herpesvirus. Further, HveC is expressed in human cells of epithelial and neuronal origin and therefore functions as a coreceptor that facilitates infection of epithelial cells on mucosal surfaces and spread to neuronal cells by both HSV-1 and HSV-2.

HveB is a cellular protein which does not exhibit the same versatility as HveC in binding to herpesviruses to facilitate their entry into cells. HveB is highly homologous to poliovirus receptor related protein 2 (Prr2). As the data presented herein establish, this protein mediates entry of certain HSV-1 mutants but does not mediate entry of wild type HSV-1 or BHV-1 into cells. However, entry of HSV-2 and PRV into cells is mediated by HveB. HveB is expressed in some human neuronal cell lines, fibroblastic cells, keratinocytes and primary activated T lymphocytes.

The differences in the ability of HveB and HveC to mediate entry of various herpesviruses into various cell types likely accounts for serotype and strain differences in tissue tropism and pathogenicity of the alphaherpesviruses. However, the discovery that these proteins serve as the gateway for entry of alphaherpesviruses into cells provides the art with heretofore unknown methods of identifying compounds useful for treating herpesvirus infection in both humans and animals.

The invention should not be construed to be limited solely to the use of the specific cellular HveB and HveC disclosed herein, or to the specific nucleotide sequences which encode them. Rather, the invention should be construed to include any and all mutants, homologs, variants and derivatives of HveB or HveC which serve to facilitate entry of a herpesvirus into a cells. An HveB or an HveC cellular protein which mediates entry of an alphaherpesvirus into a cell, as assessed in the cell entry assays described herein, is designated herein as a "biologically active" HveB or HveC protein. Biologically active forms of either HveB or HveC include any and all HveB and HveC proteins having substantial homology with the HveB and HveC proteins disclosed herein so as to facilitate entry of a herpesvirus into a cell.

In addition, the invention should be construed to include any and all mutants, homologs, variants and derivatives of polynucleotides encoding HveB or HveC which serve to facilitate entry of a herpesvirus into a cells. It is well within the skill of those in the art to clone, sequence and otherwise identify such mutants, homologs, variants and derivatives of polynucleotides encoding HveB or HveC, and to use such mutants, etc. to express useful HveB or HveC for use in the methods of the invention.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC5' and 3' TATGGC share 50% homology.

The invention should be construed to include any form of HveB or HveC having substantial homology to the HveB or HveC proteins disclosed herein. Preferably, a protein which is substantially homologous is about 50% homologous, more preferably about 70% homologous, even more preferably about 80% homologous and most preferably about 90% homologous to any one of the HveB or HveC proteins disclosed herein.

As used herein, "homology" is used synonymously with "identity." Percent identity of one polynucleotide or polypeptide with respect to another polynucleotide or polypeptide may be determined using any available algorithm, such as the BLAST program.

Mutants, derivatives and variants of HveB or HveC include any and all HveB and HveC molecules or polynucleotides encoding them, which although they may differ in their primary nucleotide or amino acid sequence from the HveB and HveC disclosed herein, retain the biological activity of HveB and HveC as defined herein. HveB and HveC are considered to be paralogs of each other, in that, although they are encoded by different genes, both exhibit entry activity for selected strains of HSV. When alignments are performed between HveB and HveC amino acid sequences, the percent identity in sequences ranges from about 33–37%. The percent similarity (allowing for conservative amino acid substitutions) between the two proteins is about 47%. Based upon these data, the invention should therefore be construed to include any HveB or HveC polynucleotide molecule which encodes an HveB or and HveC polypeptide having at least about 33–37% identity and at least about 47% similarity with the amino acid sequence of HveB and HveC shown in FIGS. 1 and 2 herein.

Further, the invention should be construed to include biologically active fragments of any homologs, mutants, derivatives or variants of the HveB and HveC proteins disclosed herein. Fragments of HveB or HveC typically may be about 50 amino acids in length in order to retain biological activity of either protein. More typically, biologically active fragments of HveB or HveC will be about 150 amino acids in length.

HveB and HveC proteins or peptide fragments thereof, may themselves be used as agents which block entry of herpesviruses into cells. As the data presented herein establish, these proteins interact directly with the virus. Thus, administration of either of these proteins to an animal, or a mutant, homolog, derivative or variant thereof, is likely to bind to virus thereby preventing virus entry into a cell. Particularly, administration of soluble forms of these proteins to an animal including a human, is a feasible method of treating alphaherpesvirus infection of the same. Soluble forms of HveB and HveC may be generated following the protocols disclosed herein wherein the membrane anchor domain of either protein is modified in some way or is deleted such that the protein is soluble. A preferred soluble form of HveB comprises a deletion in amino acids 357–385 from the full length protein. A preferred soluble form of HveC comprises a deletion in amino acids 349–378 from the full length protein.

It will be appreciated, of course, that the HveB or HveC peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the biological activity of HveB or HveC, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono-and di-alkylamino groups such as methylamino, ethylamino, dimethylamino, diethylamino, methyletijylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting virus binding activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamie, mandelic, methanesulfonic, ethariesulfonic, p-toluenesulfonic, salicyclic and the like, to provide a water soluble salt of the peptide is suitable for use as a virus binding agent.

The present invention therefore also provides for analogs of proteins or peptides of HveB and HveC. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

As noted above, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Thus, the invention should be construed to include substantially pure HveB or HveC, or mutants, homologs, variants or derivatives or modifications thereof, which are useful for inhibiting entry of an alphaherpesvirus into a cell.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

The term "substantially pure" as used herein, describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest: Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The invention should also be construed to include an isolated nucleic acid encoding HveB or HveC, or any mutants, homologs, derivatives or variants thereof.

As used herein, a "coding region" of a nucleic acid (i.e., that portion of the nucleic acid which encodes a protein) consists of the nucleotide residues of the coding strand of the nucleic acid and the nucleotides of the non-coding strand of the nucleic acid which are homologous with or complementary to, respectively, the coding region of an mRNA molecule which is produced by transcription of the nucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the MRNA coding region of a gene comprises separate regions in a genome, "mRNA-coding region" refers both individually and collectively to each of these regions.

In addition, a "coding region" of an mRNA molecule consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

As used herein, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which i part of a hybrid gene encoding additional polypeptide sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about five sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

Isolated nucleic acids encoding HveB or HveC may be transfected into cells for the purpose of producing large quantities of these protein, or for the purpose of generating cells which express HveB or HveC for use in drug screening assays. Production of large quantities of HveB or HveC may be accomplished by cloning an isolated nucleic acid encoding either protein into a baculovirus, yeast or bacterial expression vector system and then transfecting the appropriate cells with the vector to facilitate expression of either protein therein. Such technology is described herein and is well known in the art, being described in Sambrook et al. (1989, Molecular Cloning: A Laboratory Manual, Cold Spring Harbor Laboratory, N.Y.) and in Ausubel et al. (1993, Current Protocols in Molecular Biology, Green & Wiley, New York).

Expression of an isolated nucleic acid encoding either HveB or HveC in a cell is accomplished by placing the nucleic acid under the control of a suitable promoter/regulatory sequence such that the nucleic acid encoding the protein is operably linked thereto.

As used herein, the term "promoter/regulatory sequence" means a nucleic acid sequence which is required for constitutive expression or for tissue-specific, organ specific, or other specific (such as inducible, etc) expression of a nucleic acid operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the nucleic acid in a tissue specific manner.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Based upon the present discovery, compounds which are useful for inhibiting entry of an alphaherpesvirus into a cell include soluble forms of HveB and HveC as disclosed herein. In addition, compounds useful for inhibiting entry of a hirpesvirus into a cell include polynucleotides which are complementary, i.e., are in an antisense orientation with respect to the coding sequences of HveB or HveC.

"Complementary" as used herein, refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecule, are occupied by nucleotides which normally base pair with each other (e.g., A:T and G:C nucleotide pairs).

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of the coding strand of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

Antisense HveB or HveC polynucleotides include oligonucleotides which are from about five to about one hundred nucleotides in length. The antisense oligonucleotides of the invention preferably comprise between about fourteen and about fifty nucleotides in length. More preferably, the antisense oligonucleotides comprise between about twelve and about thirty nucleotides in length. Most preferably, the antisense oligonucleotides comprise between about sixteen and about twenty-one nucleotides in length. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No: 5,034,506; Nielsen et al., 1991, Science 254: 1497). Oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No: 5,034,506) or polyamide backbone structures (Nielsen et al., 1991, Science 254: 1497) may also be used.

The examples of oligonucleotide modifications described herein are not exhaustive and it is understood that the invention includes additional modifications of the antisense oligonucleotides of the invention which modifications serve to enhance the therapeutic properties of the antisense oligonucleotide without appreciable alteration of the basic sequence of the antisense oligonucleotide.

Antisense oligonucleotides may also be synthesized and expressed in any expression system suitable for this purpose, and may also be contained within a viral delivery vehicle or other vector delivery system suitable for administration to a mammal. Such systems are described herein with respect to antibodies and are equally applicable to the delivery and expression of antisense oligonucleotides.

Antibodies directed against HveB or HveC are also useful compounds for the inhibition of herpesvirus entry into cells. The types of antibodies which may be used include polyclonal antibodies, monoclonal antibodies, phage-derived antibodies, synthetic antibodies, humanized antibodies, and the like. Antibody technology is described in Harlow et al. (1988, In: Antibodies, A Laboratory Manual, Cold Spring Harbor, N.Y.). Polyclonal antibodies directed against a herpesvirus entry protein may be made by immunizing any suitable animal and obtaining immune serum from the animal at selected intervals following immunization.

Monoclonal antibodies directed against full length or peptide fragments of a cellular herpesvirus entry protein may be prepared using any well known monoclonal antibody preparation procedures, such as those described, for example, in Harlow et al. (1988, In: Antibodies, A Laboratory Manual, Cold Spring Harbor, N.Y.). Quantities of the desired peptide may also be synthesized using chemical synthesis technology. Alternatively, DNA encoding the desired peptide may be cloned and expressed from an appropriate promoter/regulatory sequence in cells which are suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125–168) and the references cited therein. Further, the antibody may be "humanized" using the technology described in Wright et al., (supra) and in the references cited therein.

To generate a phage antibody library, a cDNA library is first obtained from mRNA which is isolated from cells, e.g., the hybridoma, which express the desired protein to be expressed on the phage surface, e.g., the desired antibody. cDNTA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989. Molecular Cloning. A Laboratory Manual, Cold Spring Harbor, N.Y. and in Ausubel et al. (Ausubel et al., 1993, Current Protocols in Molecular Biology, Green & Wiley, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CHl) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1 :837–839; de Kruif et al. 1995, J. Mol. Biol. 248:97–105).

By-the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The invention thus includes an isolated DNA encoding an anti-cellular herpesvirus entry protein antibody or DNA encoding a portion of the antibody.

To isolate DNA encoding an antibody, for example, DNA is extracted from antibody expressing phage obtained as described herein. Such extraction techniques are well known in the art and are described, for example, in Sambrook et al. (supra) and in Ausubel et al. (supra).

By the term "scFv/phage" are used herein, is meant a phage particle which expresses the Fv portion of an antibody as a single chain.

Another form of antibody includes a nucleic acid sequence which -encodes the antibody and which is operably linked to promoter/regulatory sequences which can direct expression of the antibody in vivo. For a discussion of this technology, see, for example, Cohen (1993, Science 259: 1691–1692), Fynan et al. (1993, Proc. Natl. Acad. Sci. 90:11478–11482) and Wolff et al. (1991, Biotechniques 11:474–485) which describe similar the use of naked DNA as antibody/vaccine. For example, a plasmid containing suitable promoter/regulatory sequences operably linked to a DNA sequence encoding an antibody may be directly administered to a patient using the technology described in the aforementioned references.

Alternatively, the promoter/enhancer sequence operably linked to DNA encoding the antibody may be contained within a vector, which vector is administered to the patient. The vector may be a viral vector which is suitable as a delivery vehicle for delivery of the DNA encoding the antibody to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. USA 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. W094/17810, published Aug. 18, 1994; International Patent Application No. W094/23 744, published Oct. 27, 1994). Examples of non-viral vectors include, but are not limited to, liposomes, polyamine derivatives of DNA, and the like.

The identity, selection and means for obtaining a desired antibody useful for treatment or prevention of a herpesvirus infection may be performed by the skilled artisan using conventional technology when in possession of the present invention.

The invention should also be construed to include small molecules and/or peptidomimetics which bind HveB or HveC, thereby preventing attachment of HSV thereto and preventing entry of HSV into a cell. The amino acid sequences of HveB and HveC disclosed herein are useful for the generation of peptidomirnetics and other small molecules useful for treatment of herpesvirus infections. Peptidomimetics may be generated using techniques described in PCT/US93/01201 and in U.S. Pat. No. 5,334,702.

Also included in the invention are cells which have been transfected such that they express the cellular herpesvirus entry protein of the invention. Such cells may be transiently or more permanently transfected with DNA encoding biologically active HveB or HveC. Cells transfected are generated using the procedures presented herein in the Examples. Essentially, a plasmid or other vector encoding HveB, HveC or biologically active mutants, homologs, variants or derivatives thereof, is used to transfect cells, usually in conjunction with DNA encoding a selectable marker the expression of which facilitates selection of the desired transfected cells. Transfected cells are selected, cloned and the presence and expression of the desired cellular herpesvirus entry protein is assessed using ordinary molecular biology technology and suitable probes and antibodies and the like. Preferred cells include any cell type which lacks the natural form of the desired herpesvirus entry protein and include, but are not limited to, Chinese hamster ovary cells, murine melanoma cells, and swine testes cells and any mutants thereof.

Cells which express an isolated nucleic acid encoding an herpesvirus entry protein are referred to herein as "recombinant cells." Such cells may be either prokaryotic cells or eukaryotic cells. Typically, prokaryotic cells include those which are useful for propagation of DNA encoding HveB or HveC, and for expression of the protein in a form which is useful in the methods of the invention. For example, a typical prokaryotic cell is *E. coli*, which is well known in the art as a bacterium useful for the propagation of nucleic acid and expression of the same. The use of such prokaryotic cells is well known in the art and is; described, for example, in Sambrook et al. (1989, Molecular Cloning: A Laboratory Manual, Cold Spring Harbor Laboratory, N.Y.); in Ausubel et al. (1997, Current Protocols in Molecular Biology, John Wiley & Sons, New York); and in (Gerhardt et al., eds. (1994, Methods for General and Molecular Bacteriology, American Society for Microbiology, Washington, D.C.).

Useful eukaryotic cells are those which are documented in the Examples presented herein, and further include any cell type into which HveB or HveC DNA can be introduced, wherein the cell is then useful in the methods of the invention recited herein.

Cells which express HveB or HveC are useful for the identification of additional molecules capable of inhibiting HveB or HveC mediated herpesvirus entry into cells. For example, a simple screening assay may be used to identify such molecules as follows. Essentially, a population of cells which express the desired cellular herpesvirus entry protein is provided. A test compound is administered to an aliquot of the cells either before, after, or concomitantly with infection of the cells with an alphaherpesvirus. Another aliquot of identical cells is not administered the test compound. The ability of the virus to enter the cells in the presence or absence of the test compound is assessed, wherein a lower level of entry of virus into the cells in the presence of the test compound compared with the level of entry of virus into the cells in the absence of the test compound is an indication that the test compound inhibits entry of the virus into the cells. Additional viral replication assays and assays for the initiation and maintenance of or reactivation of the virus from the latent state may also be performed to determine whether the test compound is capable of inhibiting virus infection in a pathologically meaningful manner, i.e., in a manner which either reduces or ablates the pathogenicity of the virus in its natural host.

Test compounds which are identified using the screening methods just described may be any type of molecule, including but not limited to, HveB, HveC, or any homologs, mutants, variants, derivatives or biologically active fragments thereof, antisense oligonucleotides which are complementary to portions of the coding strand of the double stranded encoding HveB or HveC, antibodies which specifically bind to HveB or HveC, small molecules, peptides, a peptidomimetics, and the like which are predicted in any way to inhibit virus entry into a cell. Peptidomimetic compounds whose structure is based upon the known amino acid sequence of HveB or HveC may be designed and produced as described in PCT/US93/01201 and in U.S. Pat. No. 5,334,702.

The anti-cellular herpesvirus entry protein compound of the invention may be formulated in a pharmaceutical composition which is suitable for administration of the compound to an animal or a human patient. It will be appreciated that the precise formulation and dosage amounts will vary depending upon any number of factors, including, but not limited to, the type and severity of the viral disease to be treated, the route of administration, the age and overall health of the animal or human, the nature of the anti-cellular herpesvirus entry protein compound, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (Genaro ed., 1985, Mack Publishing Co., Easton, Pa.).

As used herein, the term "pharmaceutically-acceptable carrier" means a chemical composition with which an appropriate anti-cellular herpesvirus entry protein compound may be combined and which, following the combination, can be used to administer the anti-cellular herpesvirus entry protein compound to a patient.

The amount of the anti-cellular herpesvirus entry protein compound administered, whether it is administered as protein or as nucleic acid, is sufficient to prevent, diminish or alleviate the disease state. The pharmaceutical compositions useful for practicing the invention may be administered to deliver a dose of between about 1 ng/kg and about 100 mg/kg of patient body-weight. Suitable amounts of the anti-cellular herpesvirus entry protein compound for administration include doses which are high enough to have the desired effect without concomitant adverse effects. When the anti-cellular herpesvirus entry protein compound is a protein or peptide, a preferred dosage range is from about 10 to about 1000 $\mu$g of protein or peptide per kg of patient body weight. When the anti-cellular herpesvirus entry protein compound is administered in the form of DNA encoding the same contained within a recombinant virus vector, a dosage of between about $10^2$ and about $10^{11}$ plaque forming units of virus per kg of patient body weight may be used. When naked DNA encoding the anti-cellular herpesvirus entry protein compound is to be administered as the pharmaceutical composition, a dosage of between about 10 $\mu$g about several mg of DNA per kg of patient body weight may be used.

In the practice of the methods of the invention, a composition containing an anti-cellular herpesvirus entry protein compound is administered to a patient in a sufficient amount to prevent, diminish or alleviate a herpesvirus infection in the animal, preferably, a human.

The frequency of administration of an anti-cellular herpesvirus entry protein compound to an animal or a human patient will also vary depending on several factors including, but not limited to, the type and severity of the infection to be treated, the route of administration, the age and overall health of the animal or human patient, the nature of the anti-cellular herpesvirus entry protein compound, etc. It is contemplated that the frequency of administration of the anti-cellular herpesvirus entry protein compound to the animal or human patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate anti-cellular herpesvirus entry protein compound, these pharmaceutical compositions may contain pharmaceutically acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate anti-cellular herpesvirus entry protein compound to a patient according to the methods of the invention. Oral delivery of antibodies is described in Reilly et al. (1997, Clin. Pharmacol. 32:313–323).

Compounds which are identified using any of the methods described herein may be formulated and administered to a mammal for treatment of herpesvirus infection are now described.

The invention encompasses the preparation and use of pharmaceutical compositions comprising a compound useful for treatment of a herpesvirus infection as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient.

Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are riot limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are riot limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for ex,ample, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitan monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gain tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic: materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may (constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalinalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from 1 μg to about 100 g per killogram of body weight of the animal. While the precise dosage administered will vary depending upon any number of factors, including but not limited to, the type of animal and type of disease state being treated, the age of the animal and the route of administration. Preferably, the dosage of the compound will vary from about 10 mg to about 10 g per killogram of body weight of the animal. More preferably, the dosage will vary from about 10 mg to about 1 g per killogram of body weight of the animal.

The compound may be administered to an animal as frequently as several times daily, or it may be administered less frequently, such as once a (lay, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising a composition of the invention and an instructional material which describes adventitially administering the composition to a cell or a tissue of a mammal. In another embodiment, the kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

Entry Activity (HveB) Confers Susceptibility to Infection by Mutants of Herpes Simplex Virus Type I, Herpes Simplex Virus Type 2 and Pseudorabies Virus The data presented in this Example is summarized as follows. Certain mutant strains of herpes simplex virus type I (HSV-1) are unable to infect cells in which entry is dependent on HveA (also known as HVEM), the previously described herpesvirus entry mediator, but can infect other cells where entry is apparently dependent on other co-receptors. The mutant virus HSV-1(KOS)Rid1 was used to screen a human cDNA expression library for the ability of transfected plasmids to convert resistant Chinese hamster ovary cells to susceptibility to virus entry. A plasmid expressing the previously described poliovirus receptor-related protein 2(Prr2) was isolated on the basis of this activity. This protein, designated herein as HveB, was shown to mediate the entry of three mutant HSV-1 strains that cannot use HVEM as co-receptor, but not wild-type HSV-1 strains. HveB also mediated the entry of HSV-2 and pseudorabies virus but not bovine herpesvirus type I. HveB was expressed in some human neuronal cell lines, fibroblastic cells, keratinocytes and primary activated T lymphocytes. Antibodies specific for HveB blocked infection of HveB-expressing CHO cells and a human fibroblastic cell strain HEL299. Differences in the ability of HSV-1 and HSV-2 strains to use HveB for entry should influence the types of cells that can be infected and thereby account in part for serotype and strain differences in tissue tropism and pathogenicity.

The aims of the studies described in this Example were to isolate a human co-receptor that is functional for entry of KOS-Rid1 into resistant CHO cells and to explore the types of cells and herpesvirus strains for which entry via the new co-receptor can occur. It was found that poliovirus receptor-related protein 2(Eberle et al., 1995, Gene 159:267–272), designated herein as herpesvinis entry protein B or HveB, was capable of mediating entry into CHO cells of all three mutant HSV-1 strains, wild-type HSV-2 strains and pseudorabies virus (PRV) but had only minimal ability to mediate entry of wild-typec HSV-1 strains and bovine herpesvirus 1 (BHV-1). HveB is widely expressed in human tissues and cells, including neuronal cells and keratinocytes. In addition, it may be the only co-receptor expressed in certain human fibroblasts such as HEL299 cells, inasmuch as anti-HveB antibodies could protect these cells from infection.

The Materials and Methods used in the experiments presented in this Example are now described.

Cells and Viruses

Cell lines used included CHO-K1, HEp-2, Vero, HTI 080, NT2(Andrews et al., 1984, Lab. Invest. 50:147–162), SH-SY5Y (Ross et al., 1983, J. Nat. Cancer Inst. 71:741–747), IMR-5(Gilbert and Balaban-Malenbaum, 1980, Adv. in Neuroblastoma Res., 59–72) and HL60. Human cells passaged only a limited number of times from primary isolation included diploid lung fibroblasts HEL299 obtained from the American Type Culture collection (Peterson et al., 1968, Proc. Soc. Exper. Biol. & Med.128 :772–776), diploid fibroblasts, foreskin keratinocytes (Thomas and Laimins, I 998, J. Virol. 72: 1131–1137) and T lymphoblasts (Montgomery et al., 1996, Cell 87:427). Stable transfectants of CHO-K1 cells express;ed HveA (CHO-HVEM-12) (Montgomery et al., 1996, Cell 87:427), HveB (CHO-HveB-1and CHO-HveB-4) or HveC (CHO-HveC-1) (described herein in Example 2) or maintained the empty vector pcDNA3 (CHO-C8) (Montgomery et al., 1996, Cell 87:427). CHO-HveB-1 and -4 cell clones were transfected with pMW20 as described herein. Mother stable CHO-K1 transfectant (CHO-IEβ8) maintained a plasmid with the lacZ gene under control of the HSV-1 ICP4 promoter; expression of β-galactosidase was not constitutive but was induced by entry of the tegument transactivator VPI6 upon infection by HSV (Montgomery et al., 1996, Cell 87 :427) Using methods described previously (Terry-Allison et al., 1998, J. Virol. in press, July), CHO-IEβ8 cells were stably transfected with HveB-expressing pMW20 to yield CHO-IEβ/HveB cells, which were susceptible to infection by some HSV strains through constitutive expression of HveB and remained inducible for expression of β-galactosidase upon HSV infection. Stable transfectants of Vero cells, designated Vero15-D1 and Vero14-Rid1, were inducible for KOS gD or KOS-Rid1 gD expression, respectively, following infection with HSV. The plasmids used to produce these complementing cell lines carried the HSV-1 genes for gJ, gD (wild-type or mutant versions) and gI and the puromycin-resistance marker. For wild-type gD, the insert of pHD15(Dean et al., 1994, Virology 199:67–80) was excised by digestion with SapI and NdeI and was cloned between the same sites in pPUR (Invitrogen). In the case of Rid1 gD, the construction was similar except the insert used was from pHD31(Dean et al., 1994, Virology 199:67–80).

Wild-type HSV-1 strains used included KOS, F, 17, SC16, HFEM and Patton. Wild-type HSV-2 strains were 333 and WTW1A. HSV-1(F) (Ejercito et al., 1968, J. Gen. Virol. 2:357–364) and HSV-2(WTW1A) (Terhune et al., 1998, J. Infect. Disease, July) have been passaged only a limited number of times in HEp-2 cells since isolation. HSV-1strains MP and mP are syncytialand non-syncytial strains, respectively, selected as plaque variants under an antibody overlay (Hoggan and Roizman, 1959, Amer. J. Hyg. 70:208–219). HSV-1 mutant strains included KOS10 Rid1 and KOS-Rid2, both selected for their ability to infect gD-expressing HEp-2 cells and thus for resistance to gD-mediated interference (Dean et al., 1994, Virology 199:67–80). Recombinants of KOS, KOS-Rid1 and KOS-Rid2 were engineered to express β-galactosidase under the control of the HSV-1 ICP4 promoter; they had the appropriate SaiI to BamHI fragment of pON105(Ho and Mocarski, 1988, Virology 167:279–283) inserted between the SacI and SphI sites (changed to BamHI and SaII sits) of the viral thymidine kinase gene, replacing base pairs 47, 359 to 47, 412, and were designated KOS/tk12, KOS-Rid1/tk12 and KOS-Rid2/tk12, respectively. A gDnegative KOS recombinant, designated KOS-gD6, was engineered to contain the lacZ gene under control of the CMV promoter inserted between the HindIII site just upstream of the gD ORF and the gD stop codon, replacing base pairs 138, 349 to 139, 600. KOS-gD6 was propagated on Verol 5-D1 cells for complementation with KOS gD and on Vero14-Rid1 cells for complementation with KOS-Rid1 gD. HSV-1(ANG) was isolated from a lesion on the thigh by plating under an agar overlay (Munk and Dormer, 1963, Arch. Gesamte Virusforsch. 13:529–540).

Animal herpesviruses used were gH-negative PRV (Kaplan) (Babic et al., 1996, J. Gen. Virol. 77:2277–2285), and BHV-1(Cooper)v4a (Miller et al., 1995, Am. J. Vet .Res. 56:870–874). The PRV recombinant expresses β-galactosidase under the control of the PRV gG promoter from an insert within the gH gene and was propagated and titered on complementing gH-expressing VeroSW78 cells (Babic et al., 1996, J. Gen. Virol. 77:2277–2285). BHV-1 (Cooper)v4a, which expresses β-galactosidase under the control of the BHV-1 gB promoter from an insert within the viral thymidine kinase gene, was propagated and titered on MDBK cells (Miller et al., 1995, Am. J .Vet .Res. 56:870–874).

Except as noted otherwise, virus strains were propagated on HEp-2 cells and were titered on Vero cells.

Screening assay for plasmids encoding HSV entry proteins

Bacteria containing a HeLa cell cDNA expression library (Invitrogen Corp., Catalog no. A950-10) had previously been divided into 100 pools and frozen as glycerol stocks as described (Montgomery et al., 1996, Cell 87:427). Samples of each pool were combined into groups of 10, grown in LB medium with ampicillin and tetracycline and plasmids were prepared using standard methods. The plasmid preparations and pcDNA3 as a control empty vector were transfected into CHO-K1 cells using LipofectAMINE® reagent (Gibco-BRL, Grand Island, N.Y.) according to the manufacturer's instructions. At 24–36 hours after transfection, the cells were inoculated with KOS-Rid1/tk12 virus at 5 PFU per cell and, 6 hours later, the cells were fixed and stained with X-gal as described (Montgomery et al., 1996, Cell 87:427). The number of blue cells per 35 mm well was counted for each transfection and averaged for duplicate samples. Individual stocks in the plasmid group with the greatest activity were tested to identify the stock having the highest activity. This stock was subdivided by plating samples on one hundred 100 mm plates at about 1000 colonies per plate. The colonies on each plate were pooled and the process described above was repeated until a single plasmid, designated pMW347, was obtained. The insert of pMW347 was excised with HindIII and XbaI and was transferred to pcDNA3 to obtain pMW20, which contained both the insert and a Neo selectable marker. The nucleotide sequence of the insert was determined by the University of Chicago Cancer Research Center Sequencing Facility, using a UBI Prism 377 DNA sequencer. GenBank accession number is AF058448.

Virus Entry Assays

Cells were plated in 96-well plates and, after overnight incubation, were inoculated with virus which was serially diluted in phosphate-buffered saline containing 0.1% glucose and 1% calfserum (PBS-G-CS) and the mixture was incubated at 37° C. When antibodies were tested for the ability to protect cells from infection, serial dilutions of antiserum prepared in PBS-G-CS were incubated with the cells for 30 minutes at 37° C. followed by the addition of virus. After 2 hours of incubation with the virus-antiserum mixtures, the mixtures were removed and the cells were treated with 0.1 M citrate buffer (pH 3.0) to inactivate unpenetrated virus and the cells were then washed. PBS-G-CS was added for continued incubation. Recombinant viruses expressing β-galactosidase were used for all cell types except CHO-IEβ. Because CHO-IEpcells express β-galactosidase from a cell-associated reporter gene upon entry of HSV, viruses without reporter genes could be used on these cells. Six hours after the addition of virus, the cells were washed and incubated with the β-galactosidase substrate, O-nitrophenyl β-D galactopyranoside (ONPG), dissolved at a concentration of 3 mg/ml in phosphate-buffered saline containing 0.5% NP40. At various times after adding substrate, the plates were read at 410 nm in a Spectra Max 250 ELISA reader.

Detection of mRNAs by RT-PCR

Total RNA was isolated from 1–5×10$^6$ cells using the RNeasy kit (Qiagen, Valencia, Calif.). The 3' RACE kit (Gibco/BRL, Grand Island, N.Y.) was used for reverse transcription. PCR-amplification of cDNAs was done using primers PRR2A8(5' AGAAGCAGCAGCACCAGCAG) (SEQ ID NO:5) and PRR2A9(5' AAGGT-CACGTTCAGCCAGGA) (SEQ ID NO:6) for HveB and HVEM228(5' ATCATATGTGTGAAAAGAAGA) (SEQ ID NO:7) and HHVENT03(5' CAGGTTATCGT-GTGAAGGAG) (SEQ ID NO:8) for HveA. The β-actin control primers and thermocycling conditions have been described (Willey et al., 1996, Am. J. Respir. Cell. Mol. Biol. 14:262–271). The PCR products were analyzed by electrophoresis on a 1% agarose gel and visualized by ethidium bromide staining.

Construction of the baculovirus recombinant expressing HveB(360t)

The general strategy was as described for construction of a baculovirus recombinant expressing a secreted form of HSV-1 gD (Sisk et al., 1994, J. Virol. 68:766–775). The ectodomain of HveB minus its signal peptide was obtained by PCR amplification using primers 5'-GCGAGATCTGCGAGTTCAAGTGCTA (SEQ ID NO:9) and 5'-GCGTGATCAGTGGTGATGATGGTGAT-GCACCAGCGGACCCACATCTC (SEQ ID NO:10). The PCR product was digested with BgII and BcII (sites indicated by bold letters) and was inserted into the BamHI site of pVT-Bac to generate pCW284. pVT-Bac fuses a mellitin signal sequence to the N-terminus of an inserted coding region and a histidine hexamer to the C-terminus. The plasmid pCW284 was co-transfected with baculovirus DNA (Baculogold, Pharmingen, San Diego, Calif.) into Sf9 cells growing in monolayer culture. Viral progeny were screened for expression of the secreted recombinant protein HveB (360t) by Western blot using R143 antiserum and positive clones were plaque-purified. Bac-HveB(360t) was the viral recombinant used routinely for the preparation of purified HveB(360t). This recombinant protein comprising 360 amino acids of the HveB ectodomain was purified from the medium of infected Sf9 cells by chromatography on nickel-NTA resin (Qiagen Inc., Valencia, Calif.), dialyzed against PBS and concentrated as described previously (Sisk et al.,1994, J. Virol. 68 :766–775).

Antibodies and flow cytometry

Antiserum R143 was generated by immunizing a rabbit with Key Hole Limpet Hemocyanin (KLH) coupled to a 22-amino-acid peptide DVRVQVLPEVRGQLGGTVELPC (SEQ ID NO:11) representing a hydrophilic portion of the HveB ectodomain. This antiserum recognized the peptide used for immunization by dot blot assay and HveB(360t) by Western blot. Antiserum R146 was generated by immunization of a rabbit with purified HveB(360t) as previously described for HVEM(200t) (Terry-Allison et al., 1998, J. Virol. In press, July). Specific binding of antibodies (antiserum R146) to HveB on cell surfaces was assessed by flow cytometry. The antiserum and pre-immune serum were diluted 1:100 and incubated with the cells. After washing the cells were incubated with a 1:200 dilution of fluoresceinated goat anti-rabbit antibodies and analyzed on a Becton-Dickenson FACScan.

The Results of the experiments presented herein are now described.

Failure of KOS-Rid1 to infect CHO cells expressing HveA

The form of gD expressed is the sole determinant of the difference in ability of KOS and KOS-Rid1 to enter cells via HveA, consistent with the finding that KOS gD binds to HveA whereas binding of KOS-Rid1 gD to HveA could not be detected (Wlitbeck et al., 1997, J. Virol. 71:6083–6093). Because KOS gD differs from KOS-Rid1 and KOS-Rid2 gDs only at amino acid 27, substitutions at this site must account for the mutant phenotypes. Virus expressing the KOS-Rid1 form of gD had reduced ability, compared with virus expressing KOS gD, to infect human T lymphocytes as well as CHO-FIVEM-12 cells (Montgomery et al., 1996, Cell 87:427) whereas viruses expressing either form of gD have nearly equivalent ability to infect HeLa cells. Thus, the mutant viruses offered the opportunity to screen a HeLa cell cDNA library for plasmids expressing herpesvirus entry proteins other than HveA.

Cloning and identification of a co-receptor for KOS-Rid1 entry

The HeLa cell cDNA expression library used previously to clone HveA (Montgomery et al., 1996, Cell 87:427) was screened again by transfecting CHO-K1 cells with plasmid mixtures from the library and then challenging the cells with KOS-Rid1/tk12 to identify susceptible cells by (μ-galactosidase expression. The transfected/inoculated cells were incubated with X-gal and the monolayers were scored for the number of blue cells present. The number of cells susceptible to KOS-Rid1/tk12 infection in monolayers transfected with the control plasmid was about 8–13 per 35 mm dish. In contrast, one of the mixtures of plasmid pools from the cDNA library converted about 95 cells in the monolayer to susceptibility to KOS-Rid1/tk12 infection. The pools in this mixture were individually screened to identify the one having the highest entry activity. This pool was further subdivided into 100 pools and the process of screening for virus entry activity was repeated until a single plasmid with activity was isolated. This plasmid, designated pMW347, had a cDNA insert of 1901 base pairs excluding the poly A tail.

Sequencing of pMW347 revealed that it encoded a protein nearly identical to poliovirus receptor-related protein 2α (Prr2α) which was previously cloned on the basis of its homology to members of the poliovirus receptor subfamily of the immunoglobulin superfamily. Prr2α and Prr2δ are two membrane glycoproteins which are expressed from the same locus and transcript by differential splicing after codon number 347(Eberle et al., 1995, Gene 159:267–272). The main features of the protein encoded by pMW347, which is designated herein as HveB, are an N-terminal cleavable signal sequence, three Ig-fold domains in the ectodomain, a hydrophobic membrane-spanning region near the C-terminus, and a short cytoplasmic tail. The sequence of the HveB (Prr2α open reading frame (479 amino acids) is identical to that which has been published for Prr2α (478 amino acids) except for the presence of three additional bases following codon 351 such that codons 352 and 353 of Prrα(CCT CGC encoding ProArg) become codons 352, 353 and 354 of HveB (GCC TCG CCC encoding AlaSerPro).

Susceptibility of Cells Expressing HveB to Entry of Various Alphaherpesviruses

CHO-K1 cells which were either transiently or stably transfected with an HveB-expressing or control plasmid were inoculated with recombinant viruses containing lacZ cassettes such that susceptibility of the cells to infection could be assessed by β-galactosidase expression. Alternatively, CHO-IEβ8 cells were transfected with an HveB-expressing or control plasmid and were inoculated with non-recombinant viruses. CHO-IEβ8 cells contain the lacZ gene placed under the control of the HSV-1ICP4 promoter, so that expression of β-galactosidase is turned on by entry of an HSV strain that releases the regulatory protein VP16 from its tegument into the cell. FIG. 3 depicts the results obtained after inoculation of transfected CHO-β8 cells with a variety of HSV-1 strains. The FiveB-expressing cells (hatched bars) were susceptible to entry of the mutant strains KOS-Rid1 and KOS-Rid2 and strain ANG, but remained almost as resistant as the control-transfected cells (open bars) to entry of the other HSV-1 strains tested. Results similar to those shown in FIG. 3 have also been obtained using transiently or stably transfected HveB-expressing CHO cells and β-galactosidase-expressing recombinants of KOS and KOS-Rid1.

Figure 4A:
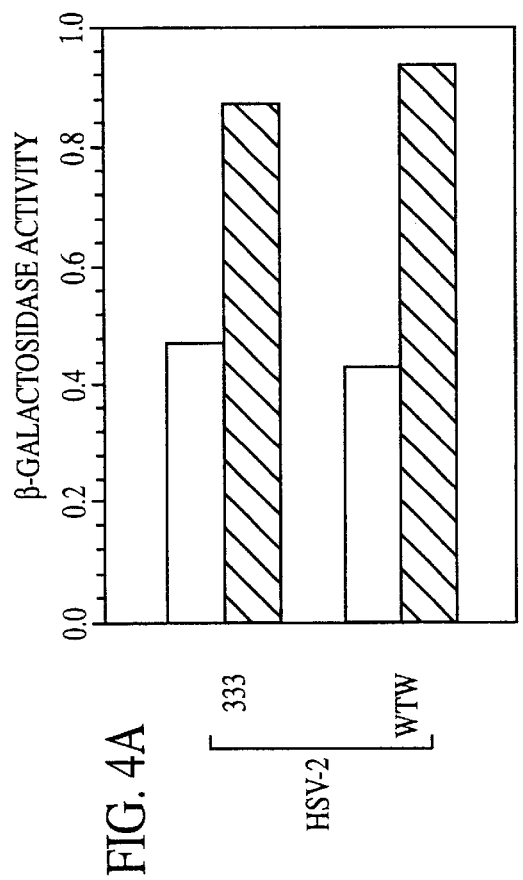
FIGS. 4A and 4B, is a pair of histograms depicting the susceptibility of HveB-expressing CHO cells to HSV-2, BHV-1 and PRV. Cells in 96-well plates were inoculated with serial dilutions of HSV-2(333), HSV-2(WTW1A) or (β-galactosidase-expressing recombinants of BHV-1or PRV.
Figure 4B:
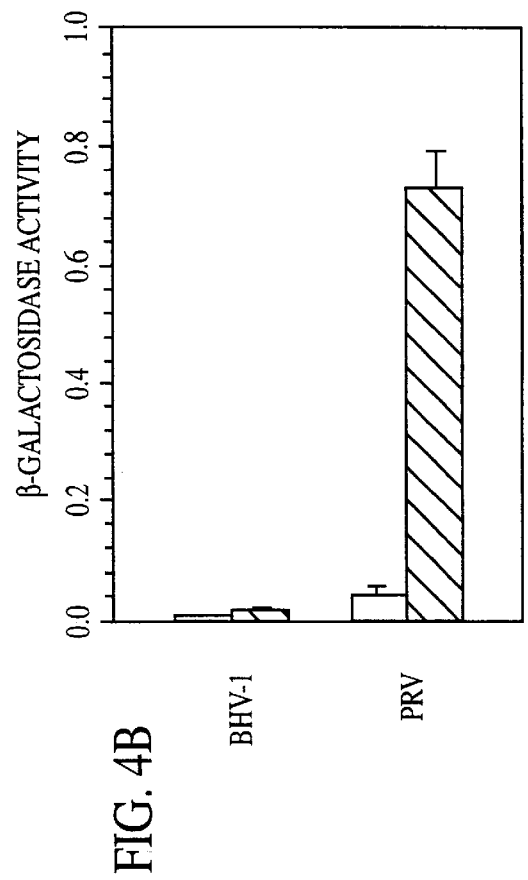

To determine whether HveB could mediate infection by other alphaherpesviruses, HveB-expressing or control CHO-IEβ8 cells were inoculated with HSV-2 strains 333 and WTW1A and HveB-expressing or control CHO-K1 cells were inoculated with β-galactosidase-expressing recombinants of BHV-1 and PRV. The results shown in FIG. 4 demonstrate that HveB expression enhanced the entry of HSV-2 and PRV but had little effect on BHV-1 entry. Similar results were obtained over a range of input doses of virus, one of which within the linear range of the dose response for each virus is shown in FIG. 4. Although control CHO cells are partially susceptible to HSV-2 entry (Shieh et al., 1992, J. Cell. Biol. 116: 1273–1281), as is evident from the results presented in FIG. 4, enhancement of viral entry was readily observed in HveB-expressing cells for some, but not all, HSV-2 strains tested. Lack of enhancement correlated with very high levels of infection of the control CHO cells, suggesting that HveB could not contribute appreciably when entry activity was already very high in its absence. Whether HveB can independently mediate HSV-2 entry or merely facilitates entry via natural co-receptors for HSV-2 expressed by CHO cells remains to be determined. The former alternative seems most likely given the results obtained with HSV-1 mutants and PRV.

Previous results (Montgomery et al., 1996, Cell 87:427) and those presented herein, establish that both HveA and HveB enhanced HSV-2 infection of CHO cells. However, HveA mediated entry of wild-type HSV-1 strains but not the mutants having amino acid substitutions at amino acid 27 in gD, while the converse was true for HveB. HveA had no demonstrable activity in promoting entry of PRV or BHV-1(data presented herein in Example 2), whereas HveB can mediate PRV entry. In Example 2, data are presented which establish that poliovirus receptor-related protein 1, designated HveC, mediated entry of all the alphaherpesviruses mentioned above and poliovirus receptor (Pvr), also designated Pvr-HveD, mediated entry of PRV and BHV-1.

Expression of HveB in Various Cell Types

To detect HveB mRNA in total RNA extracted from various cultured 5 cell types, reverse transcription followed by PCR was performed using primers that spanned three exons of the HveB gene that would generate a product specific for spliced transcripts from the HveB locus. A product of the predicted size for the amplified HveB mRNA sequence was detected in HveB-expressing CHO cells, but not in HveA- or HveC-expressing CHO cells, as expected (FIG. 5C). This product which was indicative of HveB expression was detected in several human cell lines, including NT2(teratocarcinoma), SH-SY5Y (neuroblastoma), human diploid fibroblasts, HEL299, HL60, human foreskin keratinocytes and phytohemagglutinin-stimulated human T lymphoblasts (FIG. 5A). HveC MRNA expression was detected in all of these cells except for the T lymphoblasts and HEL299 cells (Example 2). Neither HveC nor HveA mRNA could be detected in HEL299 cells, whereas HveB MRNA was detected suggesting that these cells might be resistant to KOS entry and susceptible to KOS-Rid1 entry via HveB.

Figure 6A:
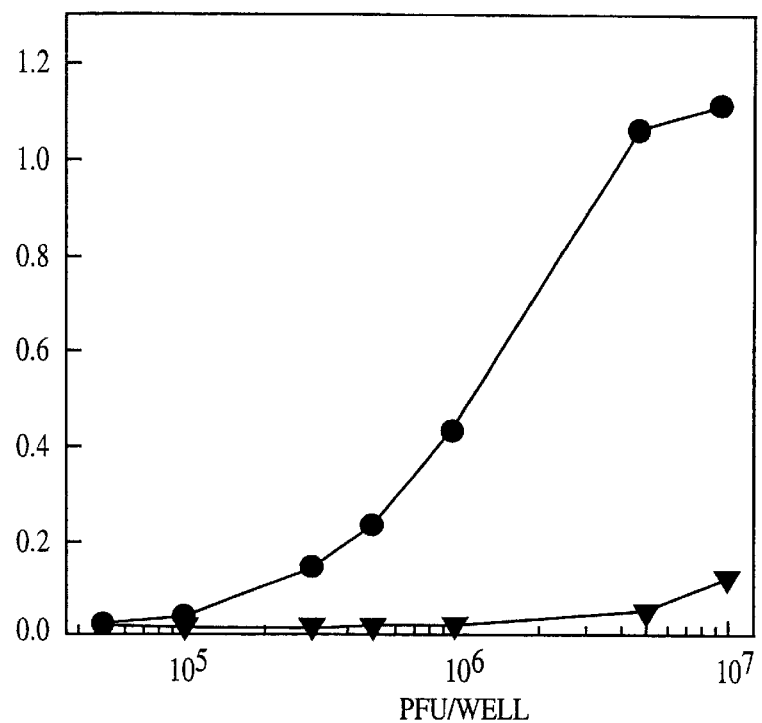
Figure 6B:
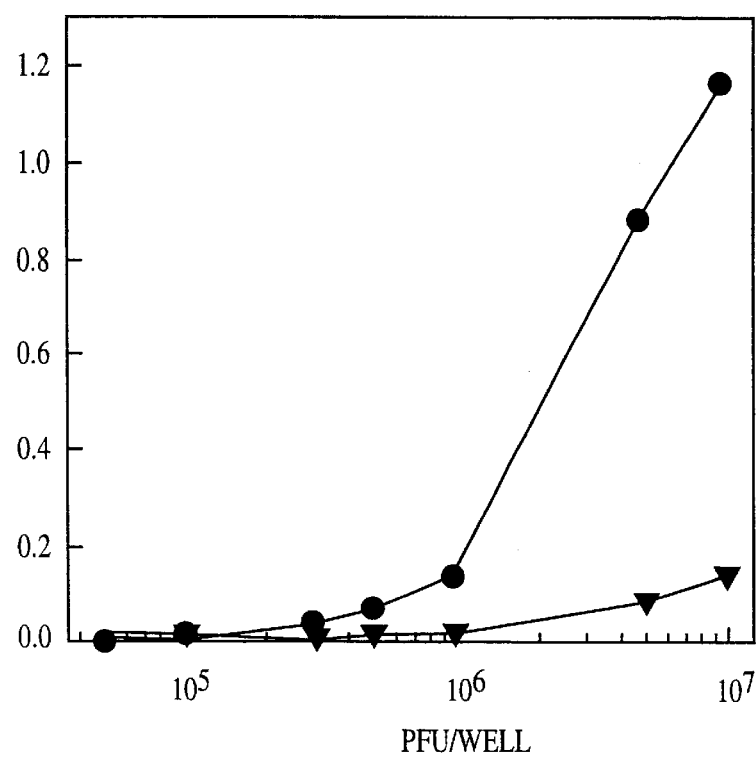
Figure 7A:
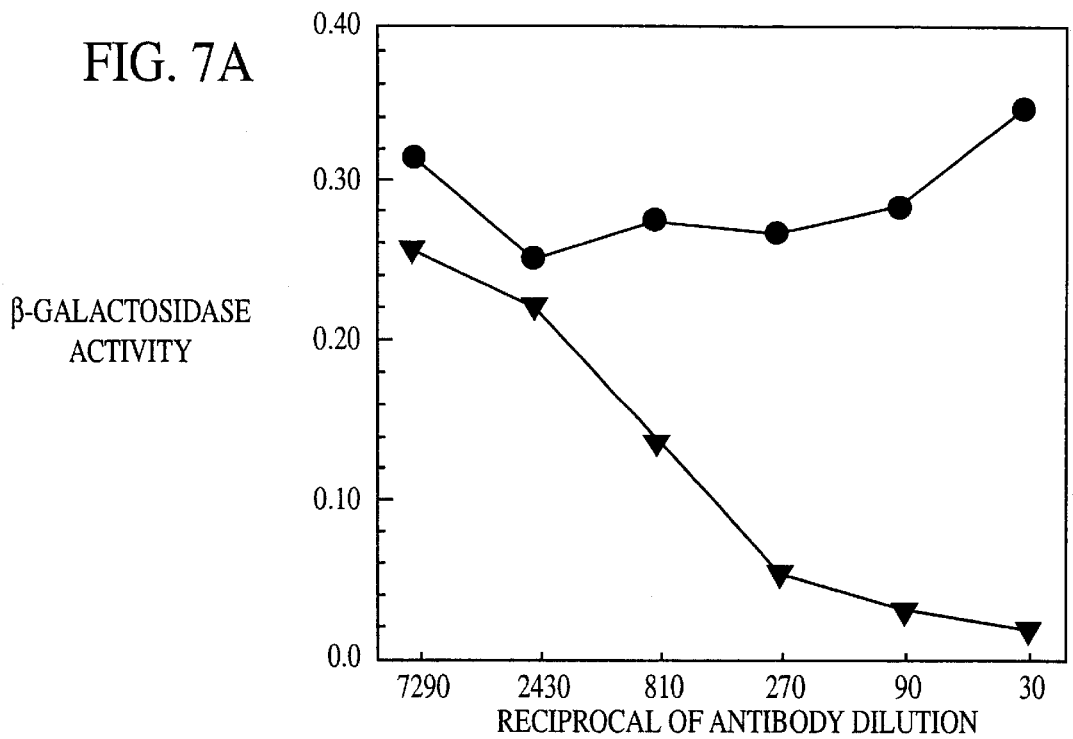
FIGS. 7A and 7B, is a pair of graphs depicting the fact that anti-HveB antibodies blocked entry of virus into CHO-HveB-1 cells (FIG. 7A) and HEL299 cells (FIG. 7B). The cells in 96-well plates were incubated for 30 minutes with serial dilutions of antiserum R146 (triangles) or per-immune serum (circles) and then a constant amount of KOS-Rid1/tk12 virus was added ($5 \times 10^5$ PFU/well in the case of: CHO-HveB-1 cells and $5 \times 10^6$ PFU/well in the case of HEL299 cells). After 2 hours of incubation, the virus-serum mixtures were removed, unpenetrated virus was inactivated by brief treatment with low pH buffer and incubation was continued for an additional 4 hours. The cells were permeabilized and ONPG substrate was added for quantitation of β-galactosidase activity.
Figure 7B:
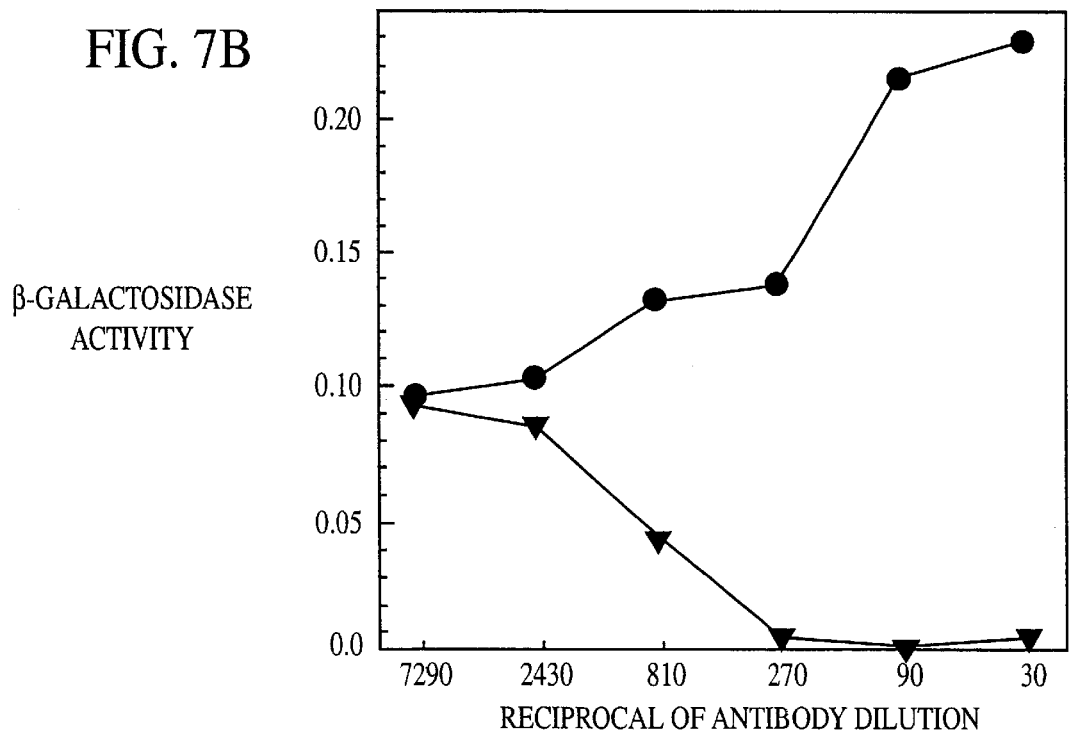

Infection of HEL299 Cells by KOS-Rid1 and Blocking of Infection by Anti-HveB Antibodies An HveB-expressing CHO cell line (CHO-HveB-1) and HEL299 cells were inoculated with serial dilutions of KOSgD6 complemented with KOS gD or KOS-Rid1 gD and viral entry was assessed by quantitation of β-galactosidase expression. As expected, the HveB-expressing CHO cells were susceptible to KOSgD6 which was complemented with KOS-Rid1 gD but were not susceptible to KOS25 gD6 which was complemented with KOS gD. Similar results were obtained using HEL299 cells (FIG. 6) whereas other cells, including HEp-2, HT1080 and HveC-expressing CHO cells were susceptible to KOS-gD6 complemented with either form of gD. A rabbit antiserum was raised against a truncated form of HveB secreted from baculovirus vector-infected insect cells. Antibodies derived from the immune serum, but not pre-immune serum, specifically bound to HveB-expressing CHO cells but did not bind to control CHO cells or HveC-expressing CHO cells as determnined by flow cytometry. Because HveB and HveC are related in structure, it was important to determine whether the anti-HveB antibodies cross-reacted with HveC. No evidence for cross-reaction was observed. Serial dilutions of the antiserum and control serum were incubated with CHO-HveB-1 cells and HEL299 cells followed by the addition of KOSRid1/tk12 virus. Viral entry into both cell types was almost completely inhibited by the antiserum in a dose-dependent fashion whereas the pre-immune serum had no effect or actually enhanced entry or events leading to β-galactosidase expression (FIG. 7).

It is unexpected that a member of the TNF receptor family (HveA) as well as members of the immunoglobulin superfamily (HveB and HveC) can mediate entry of HSV strains into cells, especially because it appears that gD may be the viral ligand for all these receptors. Evidence has been reported which suggests a direct physical interaction between the ectodomains of HveA and gD (Whitbeck et al., 1997, J. Virol. 71:6083–6093) and for binding of soluble HveA to virions via interaction with gD (Nicola et al., 199)8, J. Virol. 72:3595–3601). Similar evidence for an interaction between the ectodomains of HveC and gD has also been obtained in the present invention.

In addition, the type of allele of gD expressed determines whether HSV2-1 can enter cells via HveA or HveB. Viruses containing the wild-type form of gD can infect HveA-expressing cells, but not HveB-expressing cells, whereas the converse is true for viruses which contain the Rid mutant forms (Table 1). In the case of HveA, the fact that HveA can bind to wild-type gD but not to Rid forms of gD provides the basis for the observed specificity.

Although the PRV and BHV-1 ligands for HveB and HveC have not been identified, according to the data presented herein, these ligands are likely to be members of the gD family expressed by these viruses. The forms of gD expressed by PRV and BHV-1 exhibit only 10 to 15% sequence identity with HSV-1or HSV-2 gD. Nevertheless, a gD domain capable of interacting with HveB may be conserved among the HSV-1 Rid mutants, HSV-2 strains and PRV and another distinct gD domain capable of interacting with HveC may be conserved among HSV-1, HSV-2, PRV and BHV-1. The data presented herein identify human cell surface proteins by which these human and animal viruses could penetrate specific human cells but do not speak to other post-entry requirements for productive or latent infection.

The fact that PRV can use HveB, HveC and Pvr-HveD, and BHV-1 can use HveC and Pvr-HveD for entry into CHO cells strongly suggests that porcine and bovine homologs of these human cell surface proteins may be functional entry proteins for these animal viruses in cells of the natural host. Homologs of this human subfamily of the immunoglobulin superfamily have been identified in monkeys, mice and rats (Chadeneau et al., 1994, J. Biol. Chem. 269:15601–15605; Koike et al., 1992, J. Virol. 66:7059–7066; Morrison and Racaniello, 1992, J. Virol. 66:2807–2813). Work in progress has established that the mouse homolog of HveB, also known as the murine poliovirus receptor homolog (Mph) (Morrison and Racaniello, 1992, J. Virol. 66:2807–2813), can mediate the entry of PRV, suggesting that alphaherpesviruses have evolved to interact with highly conserved domains and/or multiple domains of proteins in this receptor subfamily.

Based upon the data presented herein, it seems likely that the variable ability of different HSV-1 and HSV-2 strains to utilize HveA, HveB and HveC (and other unidentified proteins) for entry and variable expression of these entry proteins in different cell types will govern in large part any strain-specific and serotype-specific patterns of viral spread in infected persons. Any polymorphisms in the genes encoding these proteins might also contribute to human differences in susceptibility to infection and disease.

TABLE 1

Alphaherpesvirus entry proteins and activity for mediating entry of animal and human viruses

| | Alphaherpesvirus entry protein (protein family) | | | |
|---|---|---|---|---|
| Virus | HveA(TNF-R)[a] | HveB(1g) | HveC(1g)[b] | Pvr-HveD(1g)[b] |
| HSV-1 | ++ | -- | +++ | -- |
| HSV-1Rid[c] | -- | ++ | +++ | -- |
| HSV-2[d] | ++ | + | ++ | -- |
| PRV | -- | ++ | ++ | ++ |
| BHV-1 | -- | -- | ++ | ++ |

[a]From results published by Montgomery et al. (1996) and Geraghty et al. (1998).
[b]From results published by Geraghty et al. (1998).
[c]Mutants of HSV-1 with amino acid substitutions at position 27 in gD (Q27P or Q27R).

EXAMPLE 2

Alphaherpesvirus Entry Mediated by Poliovirus Receptor Related Protein and Poliovirus Receptor This Example relates to the discovery that a human member of the immunoglobulin superfamily mediates entry of several alphaherpesviruses, including herpes simplex viruses (HSV) type 1 and type 2, porcine pseudorabies virus (PRV), and bovine herpesvirus 1 (BHV-1). This membrane glycoprotein is poliovirus receptor-related protein 1 (Prr1), designated herein as HveC. Incubation of HSV-1 with a secreted form of HveC inhibited subsequent infection of a variety of cell lines suggesting that HveC interacts directly with the virus. Poliovirus receptor (Pvr) itself mediated entry of PRV and BHV-1 but not the HSV strains tested. HveC was expressed in human cells of epithelial and neuronal origin and is the prime candidate for the co-receptor that allows both HSV-1and HSV-2 to infect epithelial cells on mucosal surfaces and spread to cells of the nervous system.

Alphaherpesviruses, including HSV-1, HSV-2, PRV, and BHV-1, infect a variety of cell types in culture, resulting in efficient virus production in a short replicative cycle. Infection in the natural host is characterized by lesions in the epidermis, usually on mucosal surfaces, with spread of virus to the nervous system and establishment of latent infections in neurons. Binding of alphaherpesviruses to cells occurs primarily through an interaction of virion glycoprotein C (gC) with cell-surface heparan sulfate whereas fusion between the virion envelope and cell membrane requires gB, gD, gH, and gL (Spear, 1993, Semin. Virol.4:167; Mettenleiter, 1995, in Viral Vectors, Academic Press, Inc., Chapter 20, pp367–393).

Several lines of evidence suggest that alphaherpesvirus gD interacts with a cell surface receptor in addition to heparan sulfate to mediate viral entry and that, in certain cell types, HSV-1, PRV, and BHV-1 can use a common gD receptor for entry (Spear, 1993, Semin. Virol.4: 167; Mettenleiter, 1995, in Viral Vectors, Academic Press, Inc., Chapter 20, pp367–393; Campadelli-Fiume et al., 1988, J. Virol. 62:159; Petrovskis et al., 1988, J Virol. 62:2196; Johnson et al., 1988, J. Virol. 62:4605; Johnson et a., 1990, J Virol.64:2569; Karger et al., 1993, Virology 194:654 (1993); Chase et al., 1993. Virology 194:365; Lee et al., 1993, J. Virol. 67:5088). Recently, a gD receptor for entry of HSV-1 and HSV-2 was identified as a new member of the TNF receptor family, called herpesvirus entry mediator (HVEM) (Montgomery et al, 1996, Cell 87:427; Whitbeck et al., 1997, J. Virol.71:6083; Nicola et al., 1998, J. Virol. 72:3595–3601), and was designated as herpesvirus entry mediator A (HveA). HveA is the principal receptor for entry of HSV into human lymphoid cells but not other cell types (Montgomery et al., 1996, Cell 87:427). Also, HveA failed to mediate the entry of PRV (Montgomery et al., 1996, Cell 87:427). A second mediator of HSV entry is identified herein as being poliovirus receptor-related protein 2 (Eberle et al., 1995, Gene 159:267). No function and no poliovirus receptor activity have been reported for this protein and it was therefore designated herpesvirus entry mediator B (HveB). As disclosed herein, HveB mediates the entry of HSV-2 strains, PRV, and certain viable mutants of HSV-1 but does not mediate the entry of wild-type HSV-1 strains or BHV-1.

These data demonstrate that there are multiple alphaherpesvirus coreceptors with differing specificities for individual viruses in the subfamily. Neither HveA nor HveB fits the specifications for a co-receptor that can mediate entry of both HSV-1 and HSV-2 into epithelial cells at the initial site of infection and into neuronal cells for the establishment of latent infection. Also, neither HveA nor HveB serves as a co-receptor for all these viruses, HSV-1, PRV, and BHV-1, and therefore these receptors do not represent common (co-receptors for these human and animal alphaherpesviruses. Because HveB is closely related to the poliovirus receptor (Pvr) (Mendelsohn et al., 1989, Cell 56:855) and to poliovirus receptor-related protein 1 (Prr1) (Lopez et al., 1995, Gene 155:261), the possibility that one or both of those proteins might mediate the entry of HSV-1 and -2 as well as PRV and BHV-1 was explored in the present Example.

Chinese hamster ovary (CHO) cells express heparan sulfate chains to which alphaherpesviruses can bind. However, CHO cells are resistant to the entry of HSV-1, PRV, and BHV-1 because of the absence of co-receptors required for virion cell fusion (Montgomery et al., 1996, Cell 87:427; Shieh et al., 1992, J. Cell Biol. 116:1273).

Transfection of CHO cells and infection of cells with virus is now described. Essentially, CHO cells were transfected with plasmids expressing Pvr or Prr1 as follows. The 5' half of the Prr1 cDNA insert in pBG38 consisted of the HindIII to BstEII fragment of the I.M.A.G.E. Consortium Clone ID# 140737, obtained from a placenta cDNA library (Lennon et al., 1996, Genomics 33:151). The 3' half of the Prr1 cDNA extended from the BstEII site to the stop codon and was obtained by two rounds of PCR-amplification of a placenta cDNA library (Clonetech, Palo Alto, Calif.) using primers int1 (5' TCCTTCACCGATGGCACTATCC) (SEQ ID NO:12) and 108(5' ACACGTACCACTCCTTCTTG) (SEQ ID NO:13) for the first round and primers int1 and 104(5' GCTCTAGAGCGGCTACACGTACCACTCCTT) (SEQ ID NO;14) for the second round. The initial thermocycling conditions were 94° C. for 1 minute, 70° C. for 1 minute, and 72° C. for 1.5 minutes. After every three cycles, the annealing temperature was decreased 3° C. until the temperature reached 55° C. and then was cycling continued to 35 total cycles. Two percent of the first PCR reaction volume was used as a template with the second primer set under the cycling conditions. The Prr1 cDNA was ligated into pcDNA3 (Invitrogen, Carlsbad, Calif.) via HinduIII and XbaI sites. The Pvr cDNA (a form) was PCR-amplified from a HeLa cDNA library (Invitrogen, Carlsbad, Calif.) as described (Koike et al., 1990, EMBO J. 9:3217) using primers pyr01 (5 ' TCTGGAGCTTGAAGAAGTGGG) (SEQ ID NO:15) and pvr07 (5' ACCTTGTGCCCTCTGTCTG) (SEQ ID NO:16) for the first round and pvr01 plus pvr08 (5' CTCTCAGTCCCGACGCTGT) (SEQ ID NO:17) for subsequent rounds of amplification. The Pvr eDNA was inserted into pcDNA3 via the EcoRV site to yield pBG42.16.

Infectivity assays were performed in 96-well plates as described (Montgomery et al., 1996, Cell 87:427) to determine whether expression of the cell proteins could provide the necessary co-receptors for viral entry. Subconfluent CHO-IEβ8 cells were transfected using Lipofectamine (GIBCO/BRL, Grand Island, N.Y.). CHO-IEβ8 cells contain an immediate-early promoter of HSV-1 upstream of the *Escherichia coli* lac Z gene and express β-galactosidase upon HSV entry due to transactivation by VP16 (Montgomery et al., 1996, Cell 87:427). The viruses used for the infectivity assays in FIG. 9 were HSV-1(KOS)tlc12 (described herein), HSV1(KOS)Rid1-tk12(described herein), PRV(Kaplan)gH-(Babic et al., 1996, J. Gen. Virol. 77:2277), and BHV-1(Cooper)v4a (Miller et al., 1995, Am. J. Vet. Res. 56:870). These viruses express β-galactosidase from a lac Z cassette inserted within their genomes. PRV (Kaplan)gH virus was propagated on SW78 cells to obtain infectious virus. The description and references for the virus strains used in FIG. 8 were as described (Montgomery et al., 1996, Cell 87:427) except for HSV-1(mP) (Hoggan and Roizman, 1959, Am. J. Hyg. 70:208) and HSV-2(G) (Ejercito et al., 1968, J. Gen. Virol. 2:357).

Figure 8:
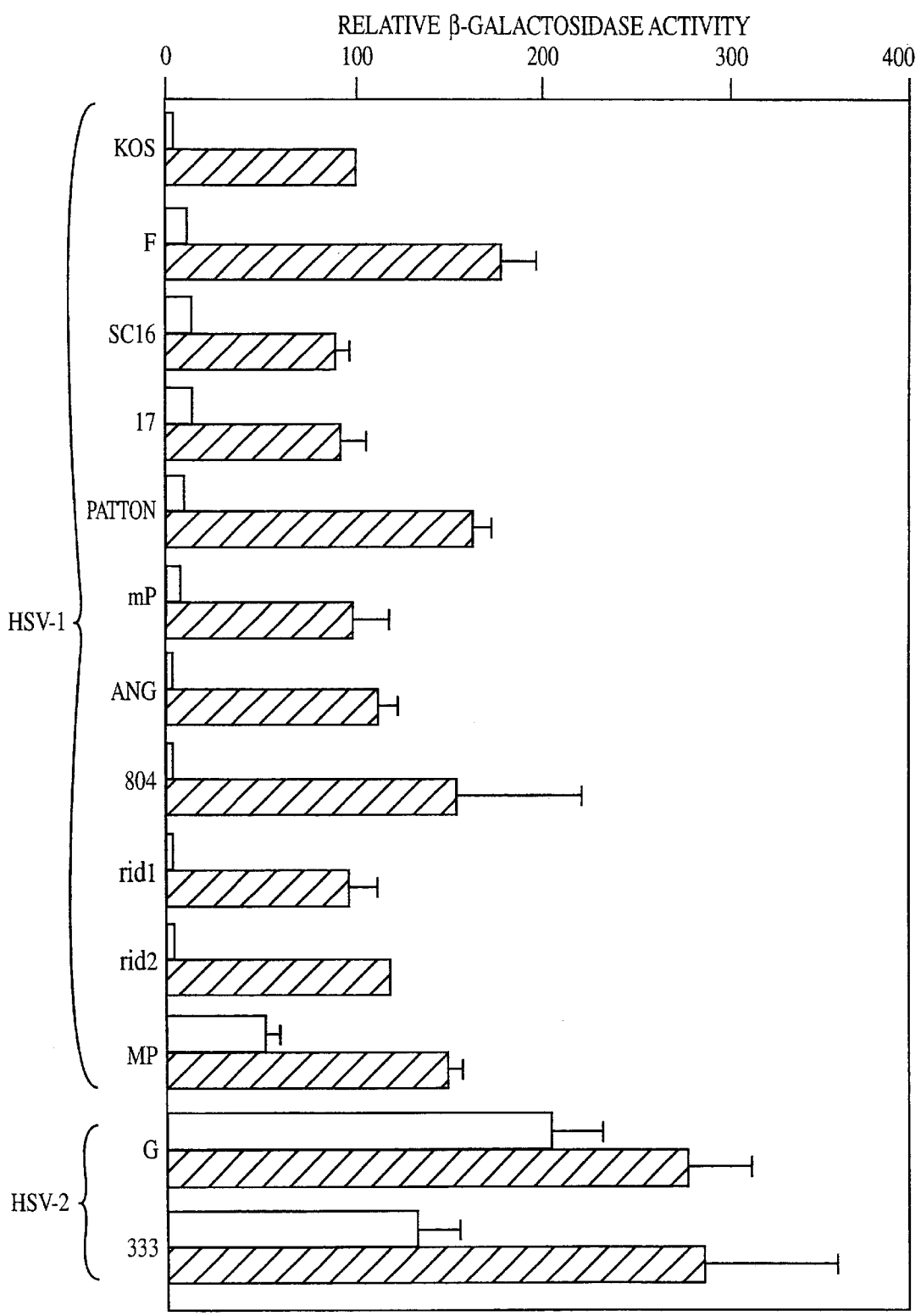
FIG. 8 is a bar graph depicting enhanced entry of HSV-1 and -2 strains into CHO cells expressing HveC. Subconfluent CHO-IEβ8 cells were transfected with a plasmid expressing HveC (pBG38-hatched bars) or a control plasmid (pcDNA3-open bars) and 24 hours later the cells were replated in 96-well plates (approx. $2-4 \times 10^4$ cells per well). Twenty four hours later, the cells were incubated with virus at a 10 range of concentrations and $\mu$-galactosidase activity was quantitated as a measure of viral entry as described (Montgomery et al., 1996, Cell 87:427). The results depicted were obtained using 50,000 of virus pfu/well and were in the linear range when virus dose was plotted against β-galactosidase activity. Each experiment was performed using a subset of the viruses that always included HSV-1 (KOS). Within each experiment, all values were made relative to the value obtained for the HSV-1(KOS)/HveC infection. Each virus was inoculated in triplicate and the mean values plus standard deviations for at least two separate experiments are shown.
Figure 9A:
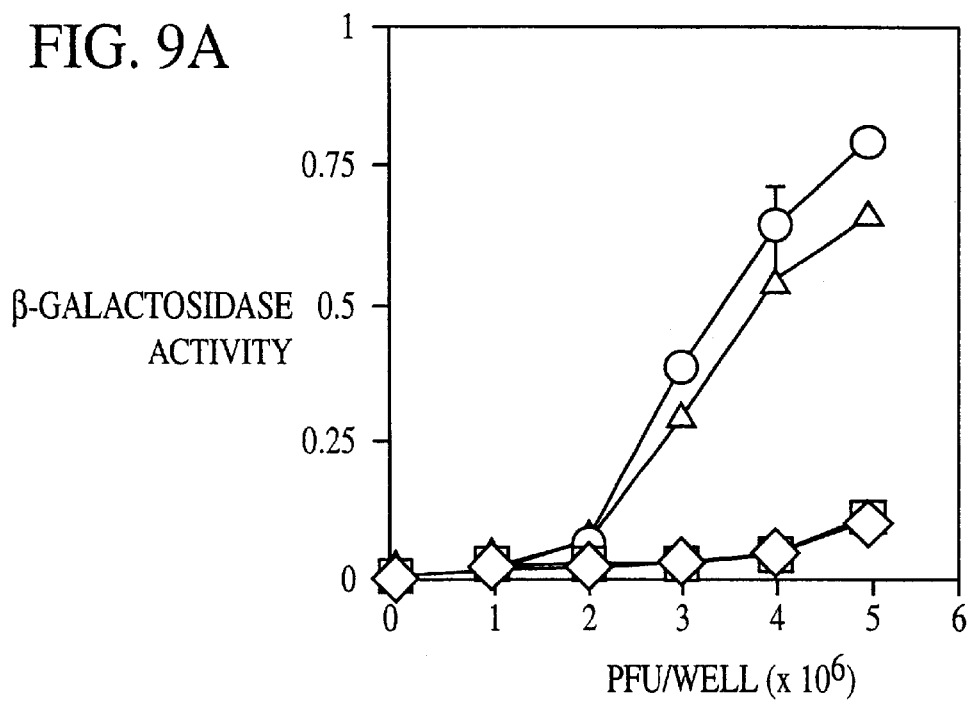
Figure 9B:
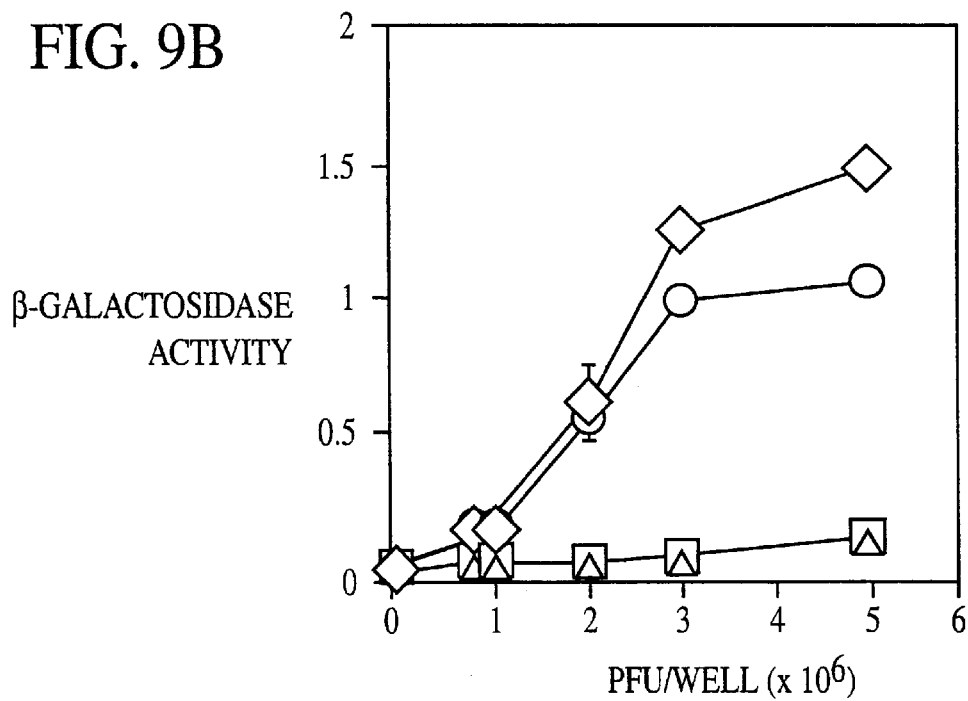
Figure 9C:
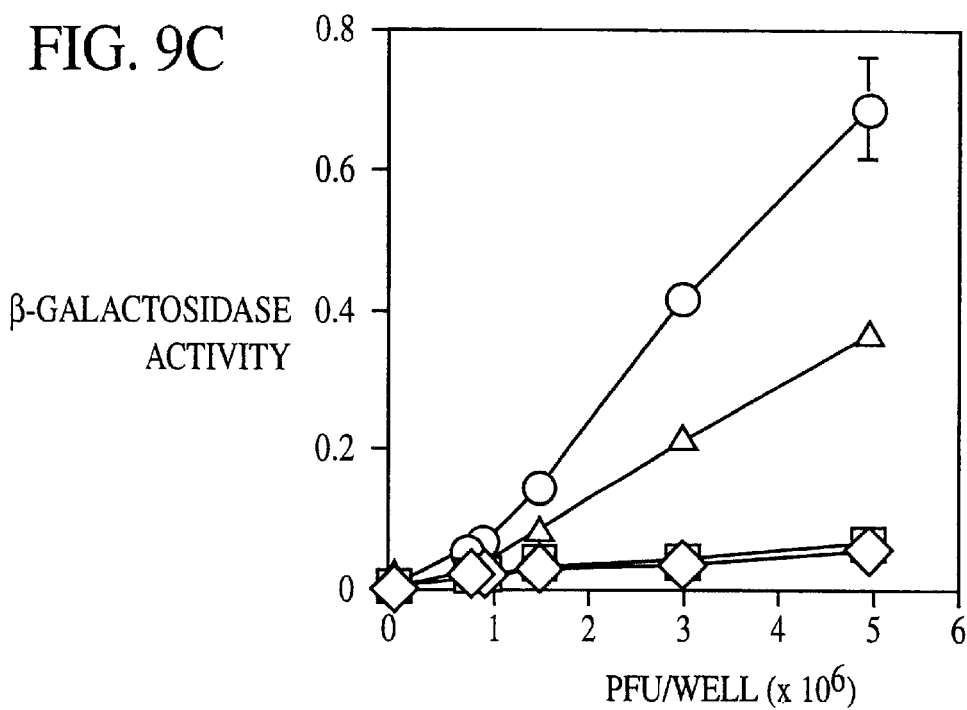
Figure 9D:
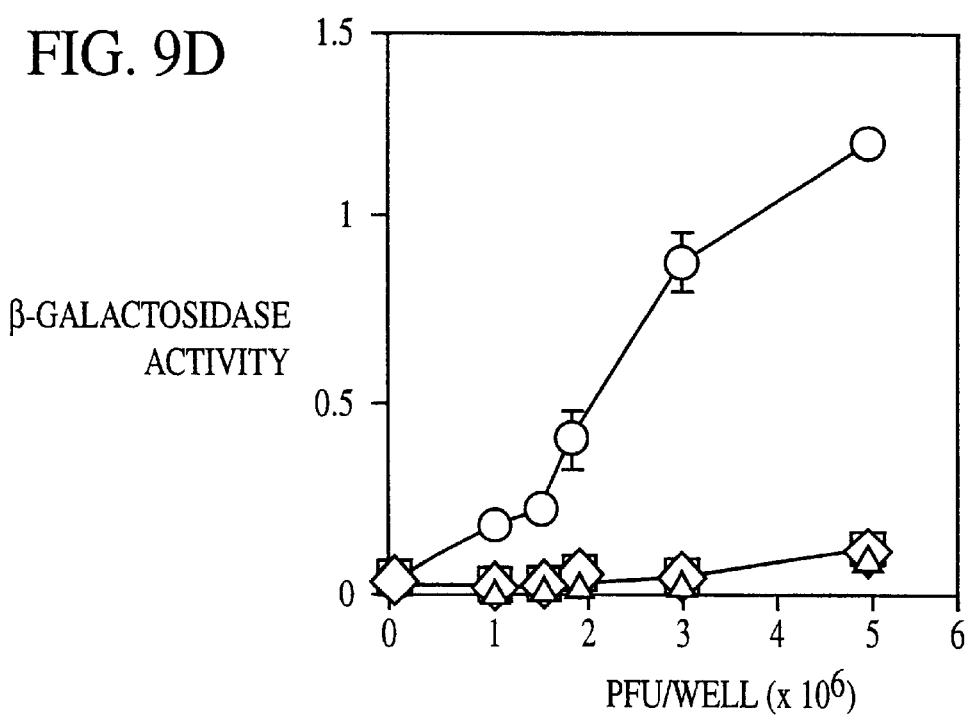

Prr1 mediated the entry of a number of HSV-1 strains and three HSV-1 mutants (ANG, Rid1, Rid2) with amino acid substitutions in gD that preclude use of HveA for entry (Montgomery et al., 1996, Cell 87:427) (FIG. 8). Prr1, designated herein as HveC, also enhanced infection by HSV-2 strains (FIG. 8) although the enhancement was not as marked in the case of this virus because control CHO cells are partially susceptible to HSV-2 infection (Shieh et al. 1992, J. Biol. 116:1273). HveC expression rendered CHO cells susceptible to infection with PRV and BHV-1, as well as HSV, with entry being a function of virus dose (FIG. 9). Three independently isolated cell lines (CHO-HveC-1, -2, and -3) stably expressing HveC were also capable of being infected by PRV, BHV-1, and HSV-1. Pvr mediated the entry of PRV and BHV-1 into cells but not the entry of HSV-1 strains (FIG. 9). The fact that HveC and Pvr, designated Pvr-HveD, can mediate entry of PRV and BHV-1 does not strictly imply that human cells could support the replication of those viruses, but does suggest that the animal homologs of HveC and Pvr-HveD could mediate entry of those viruses into cells of the natural hosts.

The nucleotide sequence of the isolate of HveC cDNA (GenBank # AF060231), as well as I.M.A.G.E. Consortium Clone ID#287663(a fragment of HveC cDNA isolated from brain tissue) (Lennon et al., 1996, Genomics 33:151) differed from the originally published sequence (Lopez et al., 1995, Gene 155:261) in the absence of single bases at positions 582, 597, and 617. The differences affected the amino acid sequence over a short range but maintained the overall open reading frame.

Nucleotide sequence analysis of pBG38 was performed by the University of Chicago Cancer Research Center DNA Sequencing Facility. The sequence differences were absences of cytosines at base pairs 582, 597, and 617 numbered according to the published sequence (Lopez et al., 1995, Gene 155:261). These changes yield a deletion of one amino acid residue and the resulting sequence, EAEYQEIRNPNGTV (amino acids 192–205) (SEQ ID NO: 18) instead of EARVPGDSGTPMAPV (amino acids 192–206) (SEQ ID NO:19).

Diagnostic restriction enzyme analysis of the clone, as well as the corresponding region amplified by polymerase chain reaction (PCR) from a HeLa-cell cDNA library, confirmed the sequence as that described herein. The HveC gene is located on human chromosome 11 (Lopez et al., 1995, Gene 155:261), which is of special interest because a human gene capable of conferring susceptibility to HSV-1infection on Chinese hamster lung cells was previously mapped to human chromosome 11 (Francke and Francke, 1981, Somat. Cell. Genetics 7:171 (1981). The genes for HveB and Pvr-HveD are located on chromosome 19(Eberle et al., 1995, Gene 159:267; Koike et al., 1990, EMBO 9:3217) whereas that for HveA is on chromosome 1 (Kwon 10 et al., 1997, J. Biol. Chem. 272:14272).

To identify human cell types in which entry of HSV-1 might be mediated by HveC, reverse transcription and PCR (RT-PCR) analysis were performed using primers specific for HveC cDNA on total RNA isolated from human cell lines and primary cells. Essentially, SH-SYSY cells are described in Ross et al. (1983, J. Natl. Cancer Inst. 71:741) and were grown in DMEM with 10% fetal calf serum. IMR-5 cells are described in Gilbert and Balaban-Malenbaum (1980, Adv. Neuroblastoma Res. 59–72) and were grown in RPMI with 10% fetal bovine serum. CHO K1 and HEL299 were obtained from American Type Culture Collection (ATCC) and were grown as described herein. NT-2 and HL60 cells were obtained 20 from the ATCC and were grown in DMEM and 10% fetal bovine serum. The primary human diploid fibroblasts were obtained from human foreskin using standard methods and the primary human foreskin keratinocytes are described in Thomas and Laimins (1998, J Virol. 72: 1131). The activated T-cell blasts were prepared and CHO HveA-12 cells were isolated as described (Montgomery et al., 1996, Cell 87:427). CHO-HveB-1cells are described herein. Total RNA was isolated from 1–5×10⁶ cells using the RNeasy kit (Qiagen, Inc., Valencia, Calif.). The 3' RACE kit (GIBCO/BRL, Grand Island, N.Y.) was used for reverse transcription. PCR amplification of HveC sequences was performed using int1 and 105(5' TCAACACCAGCAGGATGCTC) (SEQ ID NO:20) primers and one round of thermocycling conditions as described herein. The primers int1 and 105 spanned three predicted exons, therefore amplification of contaminating genomic DNA should result in a band of greater in size than the HveC-cDNA-specific (738 bp) band which was detected herein. The β-actin control primers and thermocycling conditions have been described (Willey et al., 1986, Am. J. Respir. Cell Mol. Biol. 14:262). The samples were subjected to electrophoresis on a 1% agarose gel and visualized via ethidium bromide staining.

HveC mRNA expression was detected in NT2 cells (teratocarcinoma), SH-SYSY and MR-5 cells (neuroblastomas), HL-60 cells (promyelocytic leukemia), primary human diploid fibroblasts, primary human foreskin keratinocytes (FIG. 10), and HeLa cells, but not in HEL299 cells (embryonic lung fibroblasts), or phytohemagglutinin-activated T-cell blasts (FIG. 10). As expected, expression of HveC mRNA was also detected in CHO cells stably expressing HveC cDNA but not in control CHO cells or CHO cells stably expressing HveA or HveB (FIG. 10). RT-PCR performed with primers specific for HveA cDNA yielded the expected product in keratinocytes and T lymphoblasts, but not in NT2, SH-SYSY or IMR-5 cells. NT2, SH-SYSY and IMR-5 cells are susceptible to HSV-1(KOS) infection (FIG. 11). HveC is the best candidate for the entry protein used by HSV-1(KOS) in these cells because HveC expression, but not HveA expression, was detected and neither HveB nor Pvr-HveD mediate HSV-1(KOS) entry. Although all four of the herpesvirus entry proteins are expressed in many human tissues and organs, expression of HveA is detected principally in lymphoid organs (Kwon et al., 1997, J. Biol. Chem. 272:14272); Hsu et al., 1997, J. Biol. Chem. 272:13471; Marsters et al., 1997, J. Biol. Chem. 272: 14029) whereas HveB. HveC and Pvr-HveD can be expressed in cells of the nervous system (Mendelsohn et al., 1989, Cell 56:855, and as described herein) or in cells cultured from the nervous system (FIG. 10).

A secreted form of HveA, HveA(200t), binds to virus via an interaction with HSV-1 gD and blocks infection by HSV-1(Whitbeck et al., 1997, J Virol. 71:6083; Nicola et al., 1988, J. Virol. 72:3595–3601). To begin to ascertain whether HYeC interacts with virion proteins to mediate entry, HSV-1 was incubated with HveA(200t) or a secreted form of HveC, HveC(346t), both of which are truncated forms of the protein, prior to infection.

Truncation of the protein was achieved as follows. HveC (346t) was truncated after amino acid 346, yielding a protein consisting of the predicted ectodomain of HveC, mellitin signal sequence at the amino-terminus to facilitate secretion from insect cells, and a his-tag at the carboxy terminus to facilitate purification from culture medium. Methods for construction of recombinant baculovirus expressing HveC (346t) and purification of the secreted protein were similar to those described for HveA(200t) (Whittbeck et al., 1997, J. Virol. 71:6083; Nicola et al., 1998, J. Virol. 72:3595–3601; data presented herein). Blocking experiments were carried out in 96-well plates (approx. 4×10⁴ cells per well). Serial dilutions of HveA(200t), HveC(346t), or bovine serum albumin (BSA) were mixed with virus solution (4×10⁵ pfu/ml of HSV-1(KOS)tk12), 30 mM Hepes, DMEM, and 10% fetal calf serum). The protein/virus mixtures were incubated at 37° C. for 1 hour and were then chilled on ice. The cells were chilled at 4° C. for 10 minutes prior to infection. One hundred microliters of proteinlvirus mixture was added to each well, incubated at 4° C. for one hour, and the plates were transferred to 37° C. for 6 hours. Cells were lysed by the addition of 100 gl per well of 1% NP40-containing culture medium. Fifty microliters of cell lysate was transferred to a new 96-well dish, 50 μl of chlorophenol red-P-D-galactopyranoside (CPRG) added, and the kinetics of (βgalactosidase activity was measured at 570 nm.

Figure 11A:
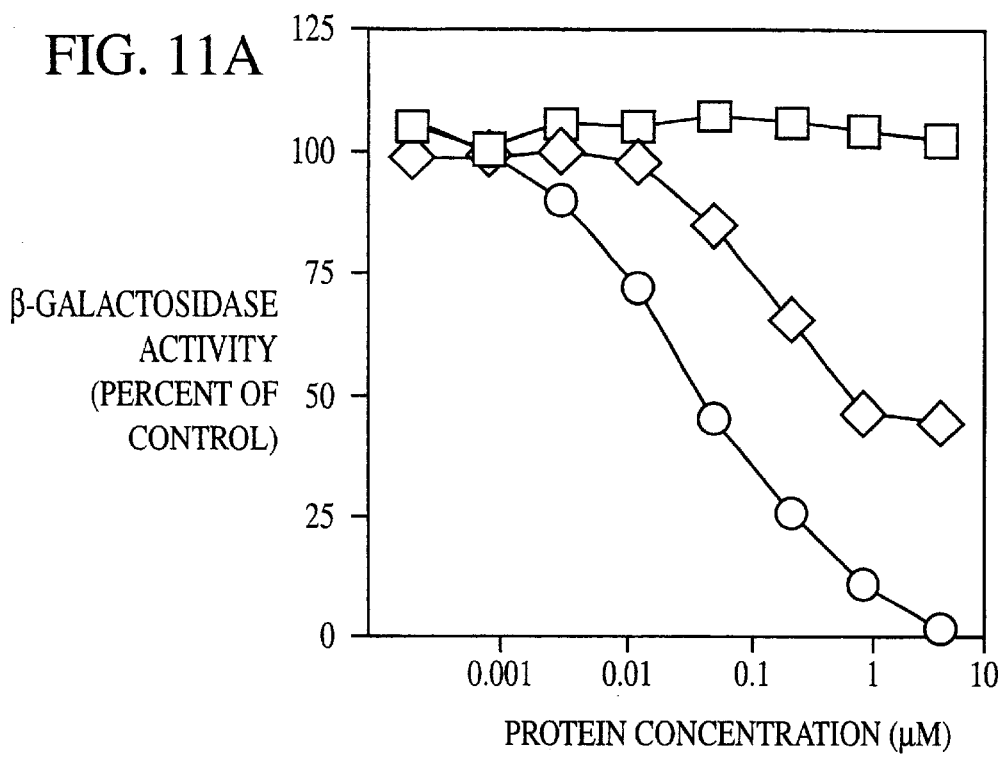
FIGS. 11A, 11B, 11C, and 11D, is a series of graphs which depict 15 blocking of HSV-1 infection by secreted HveA and HveC. HSV-1(KOS)tk12 was pre-incubated with bovine serum albumin (BSA), HveA(200t), or HveC(346t) for 1 hour at 37° C. The cell lines (IMR-5 in FIG. 11A; NT2 in FIG. 11B; CHO-HveA in FIG. 11C, CHO-HveC in FIG. 11D; approximately $4 \times 10^4$ cells/well) were then exposed to the virus/protein mixtures in 96-well plates for one hour at 4° C before transfer to 37° C. for six hours. CHO-IEβ38/HveA (CHO-HveA) cells and CHO-IEβ38/HveC (CHO-HveC) cells were generated by transfection of CHO-IEβ8 cells (Montgomery et al., 1996, Cell 87:427) as described herein. Cells were lysed and β-galactosidase activity was quantitated as a measure of infection by HSV-1(KOS)tk12 described herein. The values obtained for infections in the presence of added protein were compared to infection in the absence of added protein to determine percent of control. All values represent the average oh at least two experiments performed in triplicate. In these figures, squares correspond to data relating to BSA, diamonds correspond to data relating to HveA, and circles correspond to data relating to HveC.
Figure 11B:
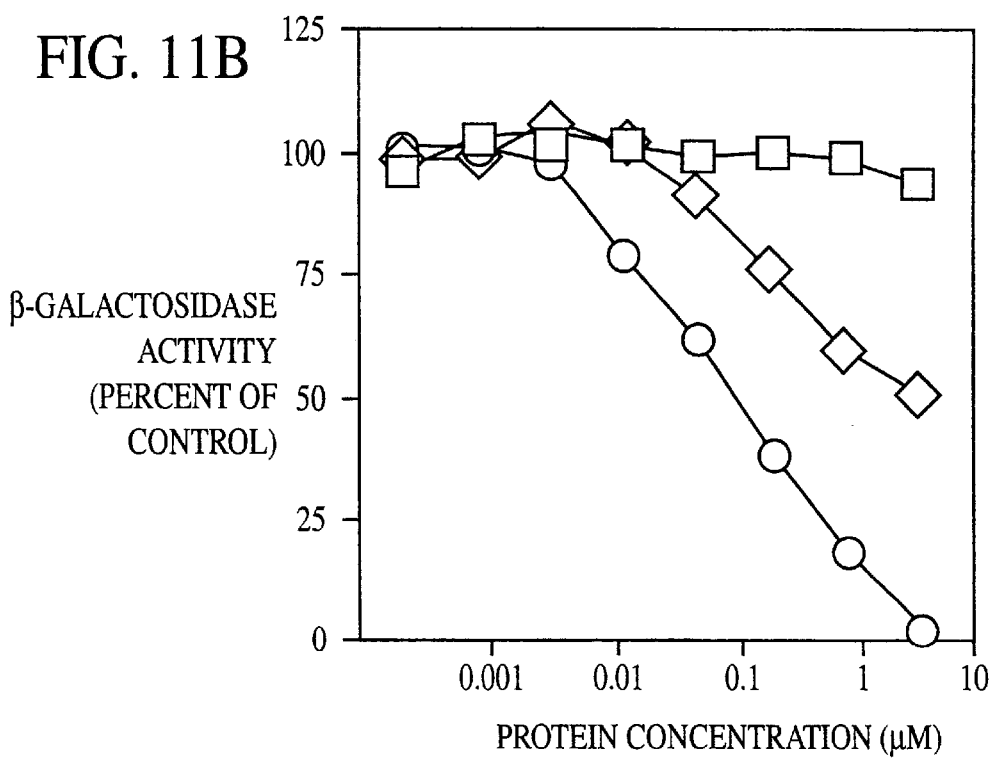
Figure 11C:
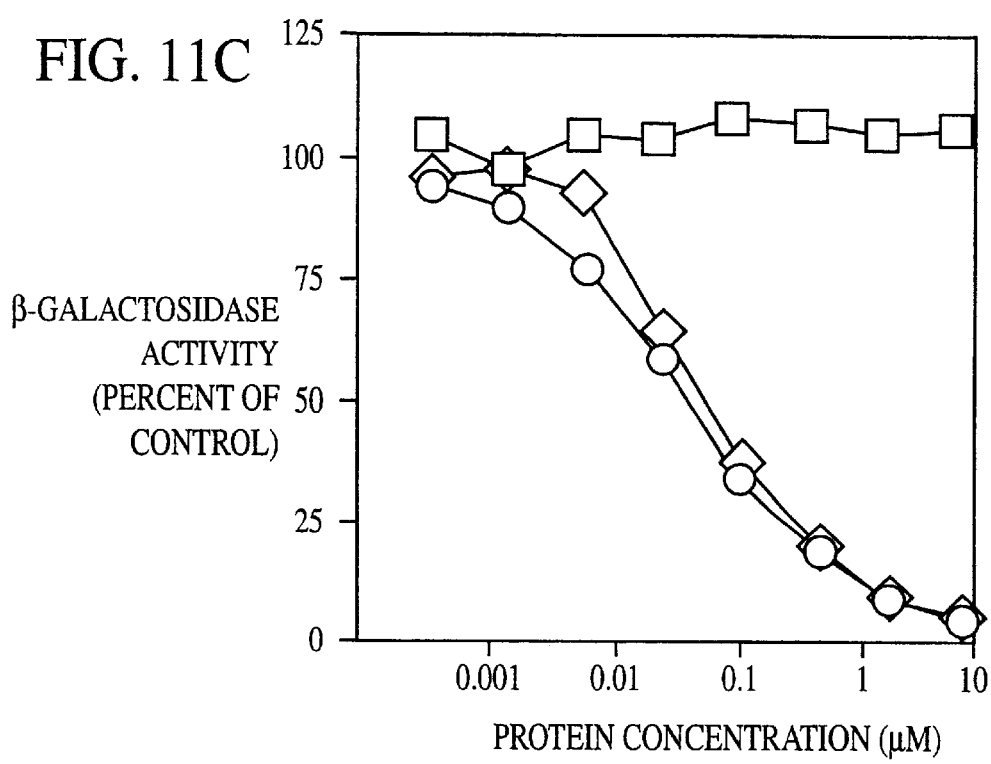
Figure 11D:
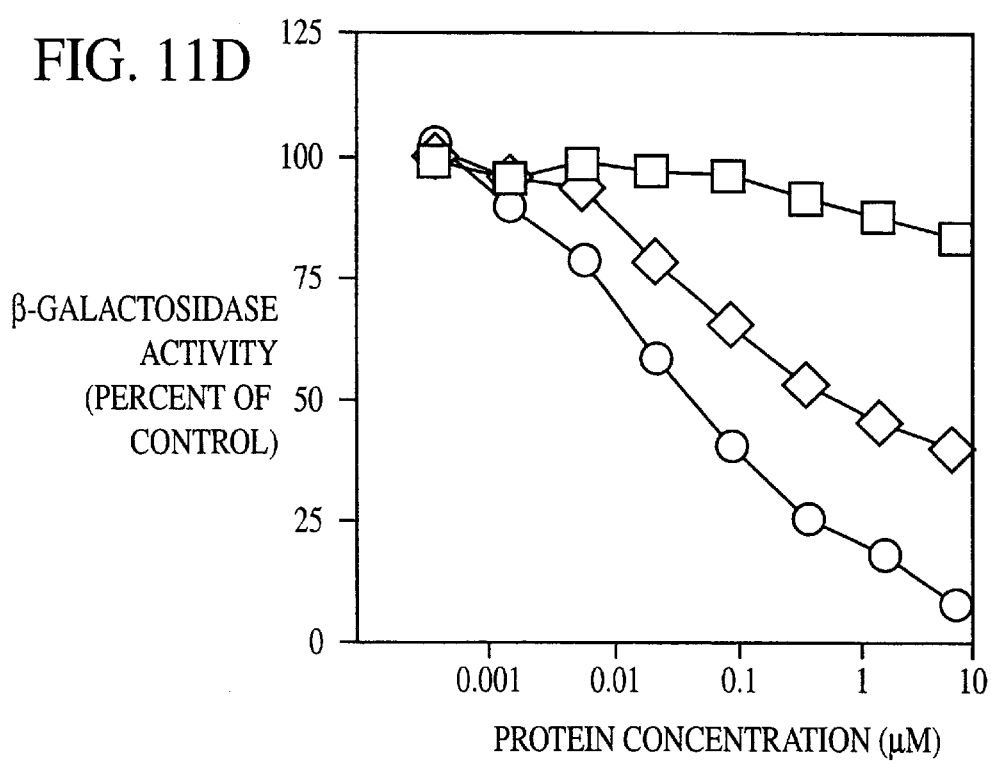

Incubation of HSV-1 with either truncated protein inhibited infection of IMP-5 cells (FIG. 11A), NT2 cells (FIG. 11B), CHO cell lines stably expressing HveA (FIG. 11C; Terry-Allison et al., 1998, J. Virol., in press, July) or HveC (FIG. 11D, data presented herein) and SHSYSY cells in a dose-dependent manner. Either protein was able to compete with membrane bound forms of HveA or HveC for interaction with virus to inhibit infection. As expected, HveA and HveC were expressed on the surface of CHO-HveA-12 and CHO-HveC-1 cells, respectively, based on flow cytometric analysis (Montgomery et al., 1996, Cell 87:427). Recent results demonstrate that HveC(346t) bound purified gD from HSV-1 and HSV-2 in vitro (data presented herein). Therefore, HveC(346t) may bind gD present on the HSV-1 virion to inhibit infection and HveC may be a receptor for virion gD.

Whereas HveA, HveB and Pvr-HveD are active for entry of subsets of the alphaherpesviruses tested herein, HveC mediated entry of all these viruses. Although there is only 10–15% amino acid sequence identity among the gD-family members of the alphaherpesviruses, there is general conservation of the positions of six cysteine residues and probably conservation of a domain recognized by HveC.

Substitutions at position 27 in HSV-1 gD abrogate entry via HveA (Montgomery et al., 1996, Cell 87:427) and enable entry via HveB (the data presented herein), while having no effect on entry via HveC. These findings, coupled with the ability of HveA and HveC to compete for critical sites on virions to block infection, indicate that each entry protein may recognize overlapping but distinct structural domains of gD. It seems likely that animal homologs of HveB, HveC, and Pvr-HveD are principal co-receptors for entry of animal alphaherpesviruses and may be active for HSV strains, as predicted by experiments which identified gD co-receptors recognized by both animal and human alphaherpesviruses (Campadelli-Fiume et al., 1988, J. Virol. 62:159; Petrovskis et al., 1988, J Virol. 62:2196; Johnson et al., 1988, J. Virol. 62:4605; Johnson et a., 1990, J Virol. 64:2569; Karger et al., 1993, Virology 194:654(1993); Chase et al., 1993. Virology 194:365; Lee et al., 1993; J. Virol. 67:5088).

Among HSV-1 and HSV-2 strains there are differences in pathogenesis, some of which may be attributable to preferences for different entry receptors and therefore, targeting of different cell types. However, a common feature of all HSV-1 and HSV-2 strains, and of most alphaherpesviruses, is their ability to replicate in mucosal epithelial and to invade adjacent nerve endings, resulting in the establishment of latent infection in nerve cell bodies. The results presented here implicate HveC as the prime receptor which facilitates HSV-1 and HSV-2 infection of mucosal surfaces and spread to the nervous system and as a prime target for novel prophylactic or therapeutic interventions. Moreover, HveC homologs may serve a similar role for infection by animal alphaherpesviruses of their natural hosts and may account for the cross-interference patterns observed for human and animal alphaherpesviruses.

EXAMPLE 3

Herpes Simplex Virus Glycoprotein D Can Bind to Poliovirus

Receptor Related Protein 1 (Prr1/HveC) or Herpes Virus Entry Mediator (HVEM/HveA). Two Structurally Unrelated Mediators of Virus Entry As described herein several cell membrane proteins have been identified as HSV entry mediators i.e., the Hve protein. HveA (formerly HVEM) is a member of the TNFR family whereas the poliovirus receptor related protein 1 and 2 (Prr1/HvieC and Prr2/HveB) belong to the immunoglobulin superfamily. The data presented in this example establish that a truncated form of HveC directly binds to HSV glycoprotein D (gD) in solution and at the surface of virioris. This interaction is dependent on the native conformation of gD but is independent of its N-linked glycosylation. Complex formation between soluble gD and HveC appears to involve one or two gD molecules for one HveC protein. Since HveA also mediates HSV entry by interacting with gD, both structurally unrelated receptors were compared with respect to their binding to gD. Analyses of several gD variants indicated that structure and accessibility of the N-terminal domain of gD, essential for HveA binding, was not necessary for HveC interaction. Mutations in functional regions II, III and IV of gD had similar effects on binding to either HveC or HveA. Competition assays with neutralizing anti-gD monoclonal antibodies (MAb) established that MAb from group 1b prevented HveC and HveA binding to virions. However, group Ia MAb blocked HveC binding but not HveA, and conversely group VII MAb blocked HveA but not HveC. Thus, without wishing to be bound by theory, it is proposed that HSV entry can be mediated by two structurally unrelated gD receptors through related but not identical binding with gD.

The Materials and Methods used in this Example are now presented.

Cells

Sf9(Spodoptera frugiperda) cells (GIBCO/BRL) were maintained in suspension in Sf90011 medium (GIBCO/BRL) or as a monolayer in supplemented Grace's medium (GIBCO/BRL).

Baculovirus Construction

The plasmid pBG38 containing the complete human HveC open reading frame was used as the template in the polymerase chain reaction(PCR). A fragment of HveC corresponding to amino acids Gln31 to His346 was amplified. The upstream primer, 5'-GCGTGATCAGGTG-GTCCAGGTGAACGACTCCATGTAT-3' (SEQ ID NO:21), added a BclI restriction site overlapping the codon for Gln31. The downstream primer 5'-CGGTGATCAATGATGATGATGATGATGTTCGGGA-GGA(3ACGGGGTGTA-3' (SEQ ID NO:22) added five histidine codons following His346, a stop codon, and a BclI site. The 979 bp fragment was digested with BclI, gel purified and ligated into the vector pVT-Bac (Tessier et al., 1991, Gene. 98:177–183) which had been previously digested with BamHI and dephosphorylated. In that construct the HveC signal peptide was replaced by a mellitin signal sequence. Due to the cloning strategy, an extra aspartic acid residue was added to the N-terminus of HveC. The generation of recombinant baculovirus has been published previously (Sisk et al., 1994, J. Virol. 68 :766–775; Willis et al., 1997, Expression and purification of secreted forms of herpes simplex virus glycoproteins from bagulovirus-infected insect cells, p. 131 –156. In M. S. Brown and A. R. MacLean (ed.), Methods in Molecular Medicine: Herpes simplex virus protocols, vol. 10. Humana Press). Briefly, the resulting plasmid pCK285 was cotransfected with Baculogold DNA (Pharmingen) into Sf9 cells. Recombinant baculoviruses were purified through two rounds of plaque selection on Sf9 cell monolayers. Plaques were tested for HveCt expression by Western blotting using the anti-HveC peptide antibody R145(see below) and amplified. The recombinant baculovirus was named Bac-HveC (346t) and the recombinant protein was designated HveC (346t) or HveCtt.

Purification of HveCt

Sf9 cells in 3-liter suspension cultures (New Brunswick Celligen Plus Bioreactor) were infected with bac-HveC (346t) at a multiplicity of infection of 4 PFU per cell. After 48 hour cells were removed by centrifugation at 2000×g for 30 minutes at 4° C. The supernatant fluid was filtered through a 0.22 μm membrane, concentrated to 1 liter and the medium was exchanged against PBS using tangential flow filtration with a 10 kDa cut-offmembrane (Millipore, Bedford, Mass.). Five ml of Ni-NTA resin (Qiagen Inc., Valencia, Calif.) pre-equilibrated with PBS were added per 3-liter culture and incubated overnight at 4° C. on a rotary shaker. The resin was pelleted at 500 rpm, for 10 minutes at 4° C., transferred to a column and washed with PBS. The bound protein was eluted with increasing concentrations of imidazole (10 mM, 25 mM, 50 mM, 250 mM and 500 mM) in 0.02 M phosphate buffer pH 7.5, 0.5 M NaCl. The 250 mM imidazole fraction was dialyzed against PBS and concentrated (10 kDa molecular weight cut-off centrifugation membrane, Millipore, Bedford, Mass.). Typically 6 to 7 mg were purified from each liter of culture.

Antibodies

A synthetic peptide, AVLRAK.KGQDDKVLVATC (SEQ ID NO:23), corresponding to amino acids 155–172 of HveC was coupled to K:LH (keyhole limpet hemocyanin) as previously described (Cohen et al., 1984, J. Virol. 49: 102–108.) and was used to immunize two rabbits. The anti-HveC peptide antiserum used here is referred to as R145. R154 polyclonal antiserum was generated by immunizing a rabbit with HveCt purified from culture supernatant of recombinant baculovirus infected cells as described herein. The R7 polyclonal antibody was raised against HSV-2 gD isolated from infected mammalian cells (Isola et al., 1989, J. Virol. 63:2325–2334). Generation of rabbit polyclonal sera R46 and R47 directed against gC, R69 directed against gB and R137 anti gH/gL has been described (Eisenberg et al., 1987, Microb. Pathd1. 3:423–435; Peng et al., 1998, J. Virol. 72:65–72). In the cosedimentation assay, a panel of antibodies were used: against gB: MAbs 5510, DL16, DL21(Samanta et al., 1994, Studies of monomeric and 6ligomeric forms of HSV gB. 19th International Herpesvirus Workshop, Vancouver, British Columbia, Abst. #29) and polyclonal serum R69(Eisenberg et al, 1987, Microb. Patho. 3:423–435); against gC: MAbs MP1, MP5(Seidel-Dugan et al., 1988, J. Virol. 62:4027–4036), 1C8(Friedman et al., 1984, Nature (London) 309:633–635) and rabbit polyclonal serum R46(Eisenberg et al., 1987, Microb. Pathog. 3:423–435); against gD: MAbs ID3(Friedman et al., 1984, Nature (London) 309:633–635), DL2(Cohen et al., 1986, J. Virol. 60: 157–166), DL11 (Cohen et al., 1986, J. Virol. 60:157–166); NMuggeridge et al., 1988, J. Virol. 62:3274–3280) and polyclonal serum R7(Isola et al., 1989, J. Virol. 63:2325–2334); against gH/gL: MAbs LP 11 (Buckmaster et al., 1984, Virology 139:408–13), 535 (Showalter et al., 1981, Infect. Immun. 34:684–692), H6(Dubin and Jiang, 1995, J. Virol. 69:4564–4568) and polyclonal serum R137(Peng et al., 1998, J. Virol. 72:65–72). Anti-capsid protein VP5 MAb (NC1) (Cohen et al., 1980, J. Virol. 34:521–531) was used in Western blots.

Glycoproteins

The production and purification of gD-1(306t) KC)S, gD-2(306t) 333, 15 gD-1(QAAt), gD-1(34t), gD-1(126t), gD-1(243t), gD-1(A290–299t), gD-1(306t) rid1, gD-1(303) ANG, gC-1(457t) and HVEM(200t)/HveA(200t) have been described (Nicola et al., 1997, J. Virol. 71:2940–2946; Nicola et al., 1996, J. Virol. 70:38 15–3822–46, 50, 53). Construction and purification of gD-1(234t), gD-1(275t) and gD1(285t) was accomplished using similar technology. The gH(792t)/gL complex was isolated from a mouse L cell line (HL7) stably transfected with plasmids pCMV3 gH(792) and pCMVgL-1 as described (Peng et al., 1998, J. Virol. 72:65–72). gB(724t) is a truncated form of gB-1 lacking the transmembrane domain and cytoplasmic tail produced in the baculovirus expression system.

SDS-PAGE and Enzymatic Digestion

Precast Tris-glycine gels (Novex) were used to separate purified glycoproteins under denaturing and reducing conditions as described previously (Whitbeck et al., 1997, J. Virol. 71 :6083–6093). Enzymatic digestion of purified protein with PNGase F (New England Biolabs, Beverly, Mass.) or endoglycosidase H (Boehringer Mannheim) prior to SDS-PAGE was performed according to the manufacturer's instructions. Mass spectrometry Matrix-assisted laser desorption ionization mass spectrometry was performed as previously described (Rux et al., 1996, J. Virol. 70: 5455–5465) on a sample of HveCt dissolved in 50% acetonitrile containing 1% trifluoroacetic acid and diluted with 2-(4-hydroxyphenylazo)benzoic acid (Aldrich Chemical Co.).

Enzyme-linked Immunosorbent Assay (ELISA)

Soluble receptor proteins, HveA(200t) or HveC(346t) in PBS were bound to microtiter plates overnight at 4° C. Plates were washed with 0.1% Tween 20 in PBS (PBS-Tween) and incubated in PBS with 5% milk and 0.2% Tween 20(blocking solution) for 30 minutes at room temperature (RT). Plates were washed with PBS-Tween and incubated with various concentrations of the soluble HSV glycoproteins to be tested in blocking solution for 2 hours at RT. Plates were washed with PBS-Tween and incubated in blocking solution containing the appropriate antiserum for 30 minutes at RT. After being washed with PBS-Tween the plates 30 were incubated with HRP-conjugated secondary antibody diluted 1000× in blocking solution for minutes at RT. Plates were then washed with PBS-Tween and with 20 mM citrate buffer pH 4.5. The HRP substrate (ABTS; Moss, Inc., Hanover, Md.) in citrate buffer pH 4.5 was added and the A405 was read with a microtiter plate reader (Bio-Tek, Winooski, Vt.). The results are presented after subtracting background signal obtained from parallel mock-coated well.

Gel-filtration

Purified soluble proteins, HveC(346t) or gD-1 (A290–299t) or combinations of both, were diluted in PBS and were incubated overnight at 4° C. A volume of 200 μl was applied to a calibrated Superdex 200 column (Pharmacia, HR 25 10/30). Fractions of 500 μl were collected and analyzed by Western blot using rabbit polyclonal sera R7 to detect gD-1(Δ290–299t) and R145 to visualize HveCt.

Binding of HveCt to Virions

Sucrose-gradient purified KOS virions ($10^7$ PFU corresponding to an estimate of S ×$10^8$ particles) were incubated with 150 μg of HveCt at 4° C. for 2 hours. Samples were loaded on top of a 10–30–60% sucrose discontinuous gradient and centrifuged for 4.5 hours at 16000×g using a SW41 swinging bucket rotor (Beckman). The virus band at the 30–60% interface was collected and concentrated by centrifugation for 1 hour at 35000×g in a SW50.1 rotor (Beckman). Viral pellets were dissolved in SDS-sample buffer, boiled and subjected to SDS PAGE and Western blotting. Membranes were probed with NC1 antibody to detect capsid protein VP5 together with R154 serum to detect HveCt. In competition assays adapted from Nicola et al. (Nicola et al., 1998, J. Virol. 72:3595–3601), viruses were first incubated with a cocktail of anti-glycoproteins antibodies or with anti-gD MAbs for 1 hour at 37° C. prior to incubation with soluble HveCt.

The Results of the experiments presented in this Example are now described.

Production and characterization of baculovirus-expressed HveC(346t)

Figure 12:
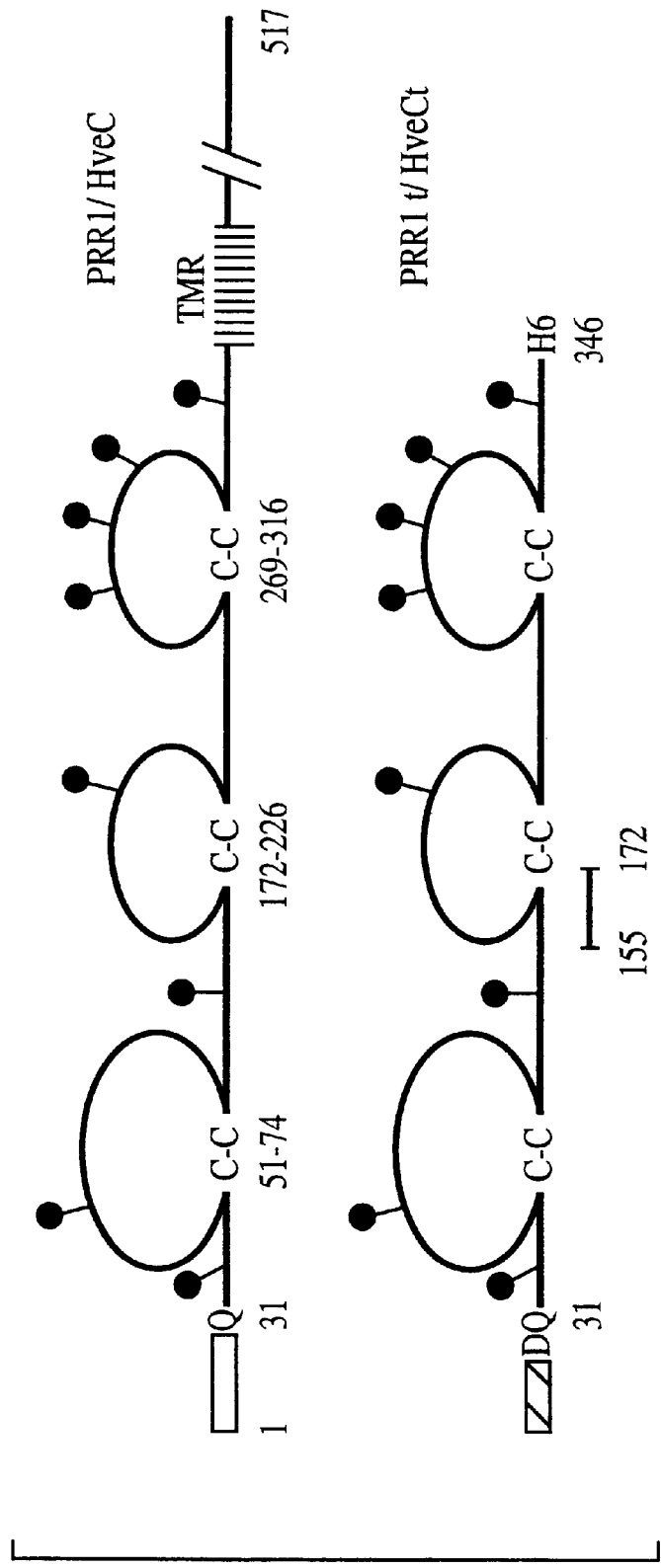
FIG. 12 is a schematic representation of Prr1/HveC proteins. The 17 amino acid human Prr1/HveC is represented with residues numbered from methionine 1. The open box indicates the HveC signal peptide and the transmembrane region is abbreviated TMR. The putative N-1 inked carbohydrates are shown as black lollipops. HveC sequence Genebank accession number is AF060231(HVEM/HveA sequence Genebank accession number is U70321). In the baculovirus construct, the mellitin signal peptide (hatched box) replaced the natural signal peptide (aa 1–30) from HveC. An additional N-terminal aspartic acid residue was inserted due to the cloning strategy. HveCt was truncated after His346 and 5 histidine residues were added to generate a six-His tag at the C-terminus of HveCt. The synthetic peptide (amino acids 155–172) was used to generate rabbit antiserum R145.
Figures 13A, 13B:
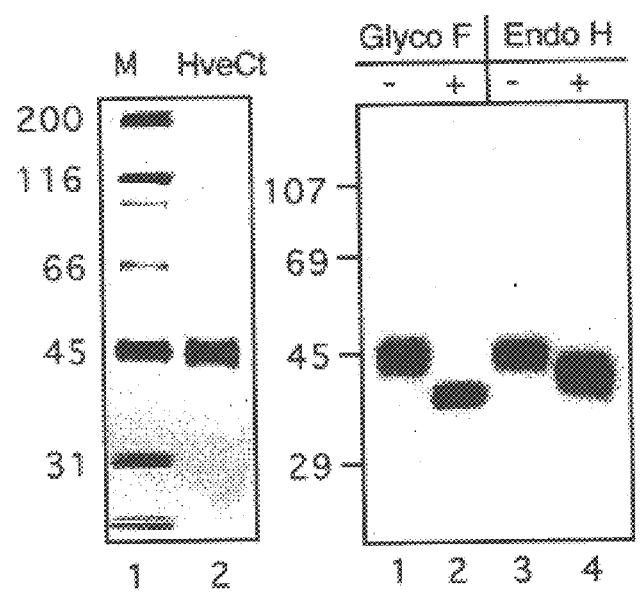
FIGS. 13A, 13B, 13C, and 13D, illustrates the results of a biochemical characterization of HveCt.
Figure 13C:
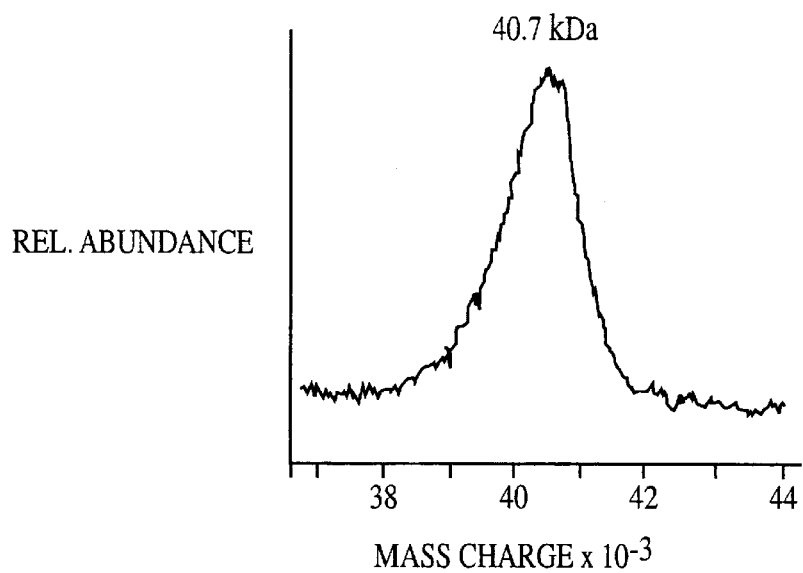
Figure 13D:
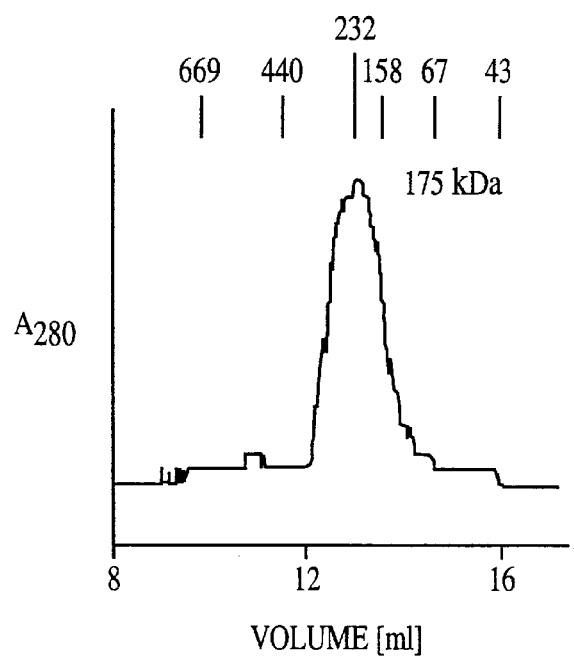

A large quantity of the soluble human HveC ectodomain bearing a C-terminal six-histidine tag, named HveC(346t), or HveCt for short, was produced in the baculovirus expression system (FIG. 12). It was possible to consistently obtain 6 to 7 mg of purified HveCt per liter of cell supernatant. After purification by nickel chlromatography, HveCt was analyzed by SDS PAGE under denaturing and reducing conditions (FIGS. 13A and 13B). The purified protein as revealed by silver stain migrated as a thick band with a size of 45 kDa (FIG. 13A). On Western blot, the same band reacted with anti-peptide rabbit serum R145(FIG. 1313, lanes 1 and 3). The primary amino acid sequence of HveC contains 8 consensus sites for N-linked glycosylation in the extracellular domain (FIG. 12) (Example 2 herein; Lopez et al., 1995, Gene. 155:261–265). Purified HveCt was treated with glycopeptidase F or endoglycosidase H to determine the presence and structure of the N-linked carbohydrates. Treatment with glycopeptidase F yielded a sharper and faster migrating band on a Western blot (FIG. 13B, lane 2). The apparent size of the protein core (36 kDa) was consistent with the calculated molecular weight of HveCt. Endoglycosidase H digestion resulted in the appearance of a broad band between 45 kDa to 38 kDa (FIG. 13B, lane 4). An increased amount of enzyme in the reaction did not alter this pattern suggesting that digestion was complete tinder these conditions. This indicated that several glycosylation sites of HveCt generated in insect cells were used; however, the number of complex or high-mannose type carbohydrates on each protein was variable. The isoelectric point (pI) of HveCt was determined to be 6.6 by isoelectric focusing gel analysis and this correlates with the theoretical value of 6.39. By mass spectrometry analysis the molecular weight of the HveCt glycoprotein was 40.7 kDa but the broadness,; of the peak suggested considerable heterogeneity (FIG. 13C), probably reflecting the variability of HveCt glycosylation. The same variability was observed when HveCt was separated on a size exclusion column (FIG. 13D). In such experiments the size of the eluted protein was 176 kDa suggesting that it can oligomerize in solution. The observed molecular size was consistent with the presence of an oligomer made up of four HveCt molecules.

Interaction Between Purified gD and HveC in Vitro

In Example 2 herein, it has been established that HveC expression by CHO cells allowed HSV entry into these otherwise non-permissive cells. This observation is reminiscent of the role played by HveA in the same system (Montgomery et al., 1996, Cell. 87:427–436). Since HveC allowed entry into CHO cells in the absence of coexpression of HveA, it was hypothesized to play a similar role as a gD-binding cellular receptor. To more precisely analyze the molecular interaction underlying the biological activity of HveCt ELISA was performed to study the direct binding between HveCt and virion glycoproteins, and in particular gD. In a preliminary experiment ninety-six-well plates were coated with increasing amounts of HveCt and then incubated with varying concentrations of soluble gD(306t) (in this study gD(306t) refers to the truncated protein derived from the HSV-1 KOS strain unless stated otherwise). Saturation of the plate, based on maximal gD binding, was achieved at a concentration of HveCt of 200 nM. This concentration was used in subsequent experiments described below.

Specificity of gD for Different Viral Receptors

Figure 14:
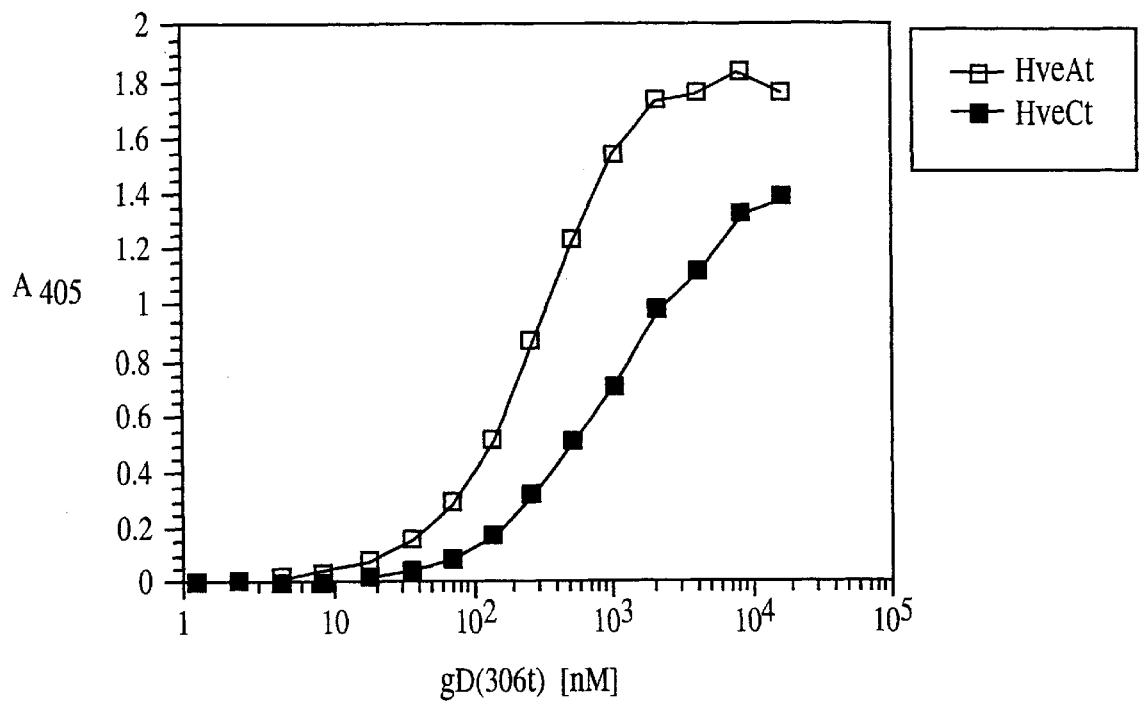
FIG. 14 is a graph depicting a comparison of gD binding to HveCt and HveAt. ELISA plates coated with HveCt or HveAt at 200 nM in PBS were incubated with increasing concentrations of gD(306t). Bound gD was detected with R7 antiserum followed by peroxidase conjugated secondary antibody and substrate. Absorbance was read at 405 nm.

It is known that HveA binds to gD in vitro (ELISA) and to viral particles (Nicola et al., 1998, J. Virol. 72:3595–3601; Whitbeck et at, 1998, J. Virol. 71:6083–6093). This interaction was specific since neither soluble forms of the human immunodeficiency virus (HIV) receptor CD4, nor the Rous Sarcoma Virus (RSV) receptor Tva, nor the mannose-6-phosphate receptor bound to gD (53). Here, it was found that gD directly interacted with HveC in vitro (FIG. 14). In this experiment, ELISA plates were saturated with HveCt or HveAtand incubated with gD at concentrations ranging from 1 $\mu$M to 20$\mu$M. Binding of HveCt with gD was saturable at a concentration of 10–20 RM gD whereas in the case of HveA saturation was achieved at a lower gD concentration (2–3 $\mu$M) as reported previously (Whitbeck et al, 1997, J. Virol. 71:6083–6093). The apparent affinity, based on half-maximal binding, seemed to be slightly higher for gD(306t) binding to HveAt (KD =0.3 $\mu$M) than to HveCt ($K_D$=1 $\mu$M). In addition, the slopes of these two curves were different which might reflect differences in complex formation. These observations led to the following experiments to further delineate the differences as well as the similar aspects of binding of HveC and HveA to gD.

Characterization of the Interaction Between gD and HveC in Vitro (i) Specificity for gD.

Figure 15A:
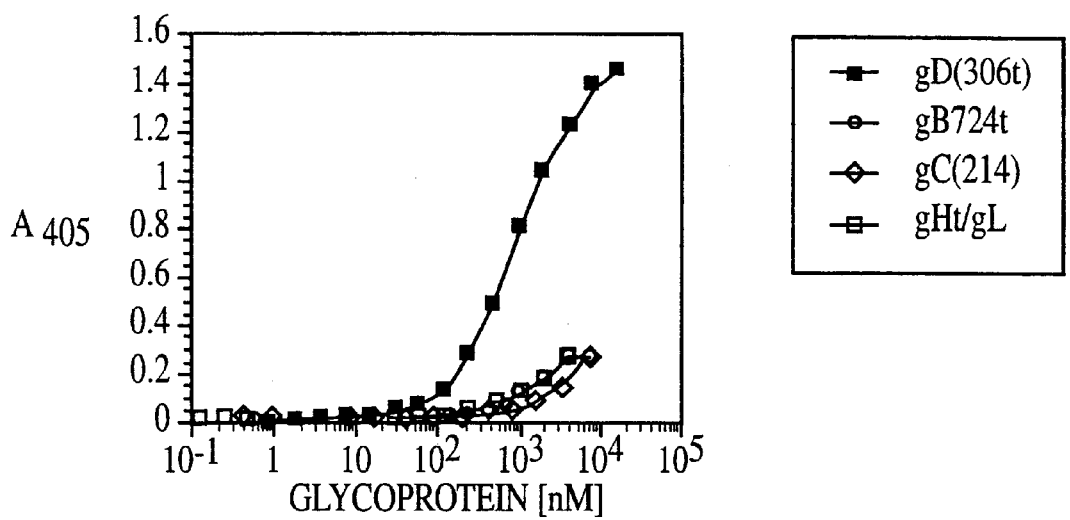
FIGS. 15A, 15B, 15C and 15D, is a series of graphs depicting an analysis of binding of gD to HveCt by ELISA. Ninety-six well plates were saturated with 50 μl of 200 nM HveCt in PBS and were incubated with variable concentrations of purified HSV glycoproteins.

Several HSV glycoproteins are involved in virion entry into cells. To explore the possibility that HveCt could bind to other HSV-1 glycoproteins, LISA was performed using soluble forms of several other envelope glycoproteins (i.e. gB, gC, gHIgL). These imniunoaffinity purified proteins display native immunoreactivity when tested with several monoclonal antibodies which recognize conformational epitopes (Dubin and Jiang, 1995, J. Virol. 69:4564–4568; Nicola et al., 1996, J. Virol. 70:3815–3822; Peng et al, 1998, J. Virol. 72:65–72). HveCt coated plates were incubated with increasing concentrations of gD-1(306t), gC-1(457t), gB-1(724t) or gH(792t)/gL and bound glycoproteins were detected with specific antibodies. Only gD displayed significant binding to HveCt (FIG. 15A).

(ii) gD-1 Versus gD-2.

Figure 15B:
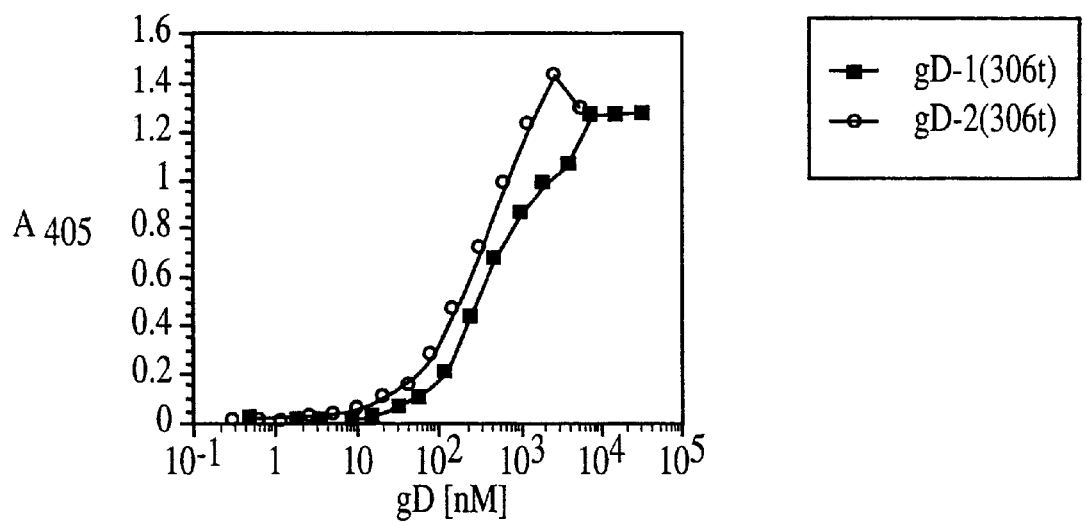

The external domain of gD from HSV-1strain KOS and HSV-2 strain 333 share 88% identity with 35 differences in amino acid sequence scattered throughout the gD ectodomain. Binding of baculovirus-produced gD-2(306t) to HveCt was compared to binding of gD4(306t) by ELISA (FIG. 15B). Despite considerable sequence difference both glycoproteins bound to FiveCt equally well, consistent with the ability of both HSV type 1 and 2 to utilize ilveC to enter cells (Example 2 herein).

(iii) Glycosylation.

Figure 15C:
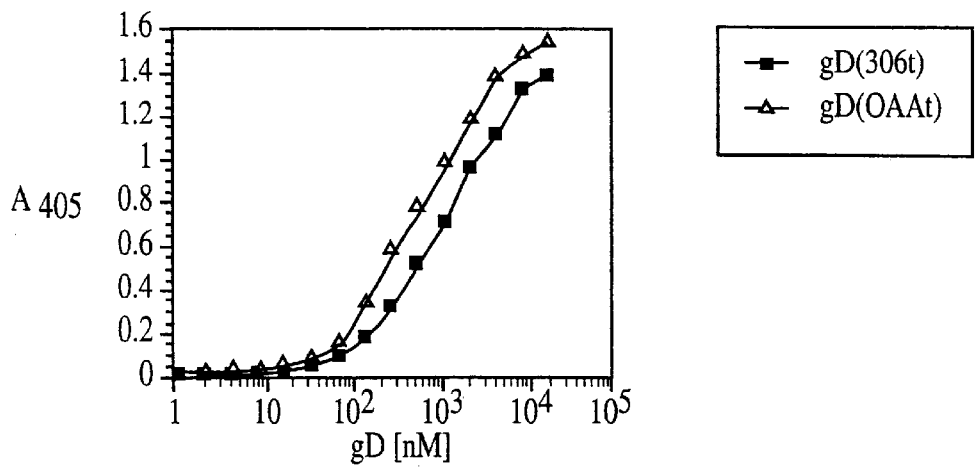

Sodora et al. (1991, J. Virol. 65 :4424–443 1) constructed a triple mutant of gD-1 KOS, named gD(QAA), in which the three signals for addition of N-C11O were eliminated. Virus comprising this mutated gD displayed normal infectivity in vitro and in vivo (Sodora et al., 1991, J. Virol. 65:4432–4441; Tal-Singer et al, 1994, Virology. 202:

1050–1053). In addition the truncated form gD(QAAt) expressed in baculovirus interacted with HveA as well as the glycosylated gD(306t) (Whitbeck et al., 1997, J. Virol. 71:6083–6093). Here, gD(QAAt) was used to assess the implication of N-1 inked carbohydrates in gD binding to HveCt (FIG. 15C). The interaction of N-CHO free protein gD(QAAt) to HveCt was not significantly altered as compared to the glycosylated counterpart gD(306t).

(iv) Native Structure.

Figure 15D:
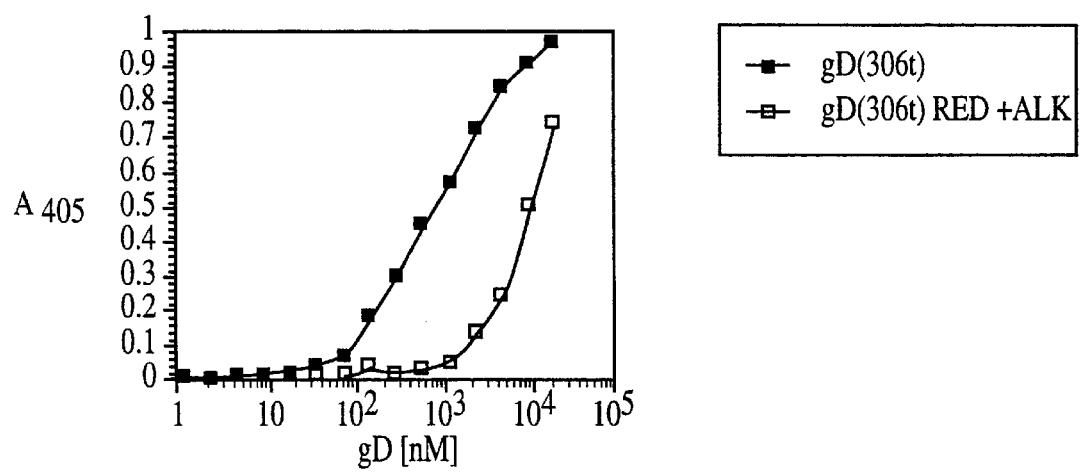

When gD(306t) was denatured by heating in the presence of a reducing agent and alkylated to prevent refolding, its binding to HveCt was significantly reduced (FIG. 15D). The denatured gD binding curve suggested a different kind of interaction, presumably less specific or possibly restricted to a linear portion of HveC resulting in a lower affinity binding. This result correlates with the observations that maintenance of the gD structure is necessary for biological activity (Long et al., 1992, J. Virol. 66:6668–6685; Nicola et al., 1.996, J. Virol. 70:3815–3822). These data highlighted several similarities in the binding of HveCt and HveAt to gD. Both receptors interacted with gD-1 and gD-2; in both cases binding was not affected by N-glycosylation of gD and in both cases the native structure of gD was required for efficient binding.

Comparison of Variant gDs Binding to HveC and HveA (i) ANG and rid1 Mutants.

Figure 16A:
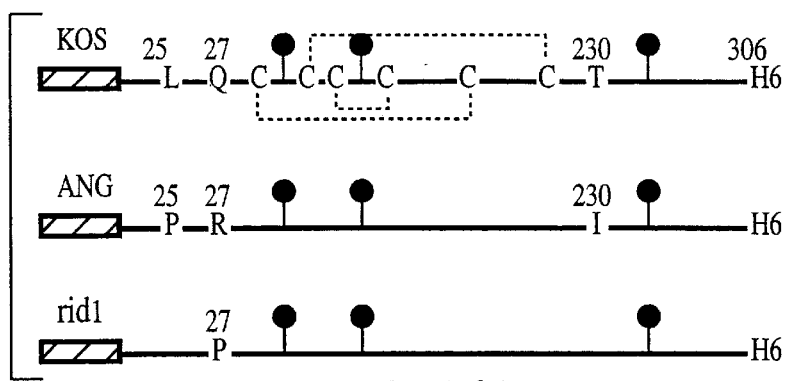
FIGS. 16A, 16B and 16C, depicts binding of gD(306t) from HSV strains KOS, ANG and rid1 to, HveAt (FIG. 16B) and HveCt (FIG. 16C).
Figure 16B:
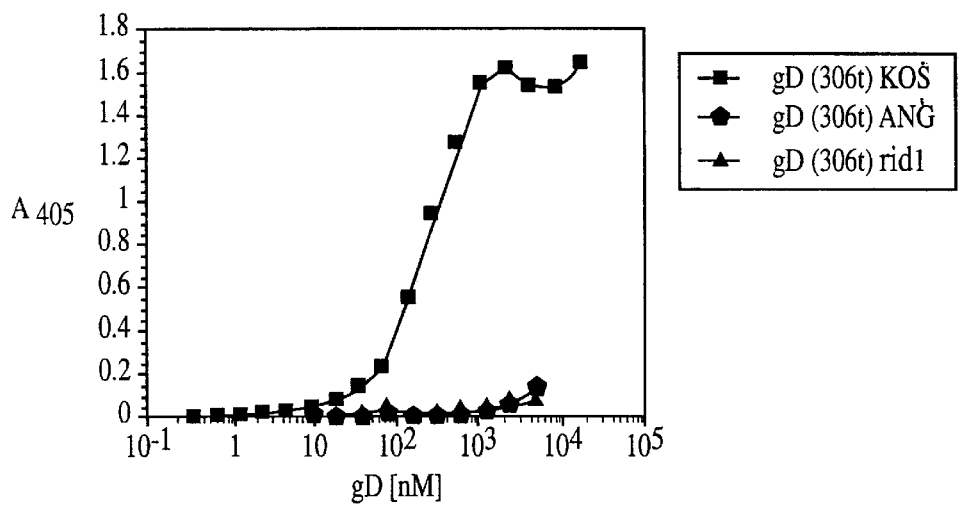
Figure 16C:
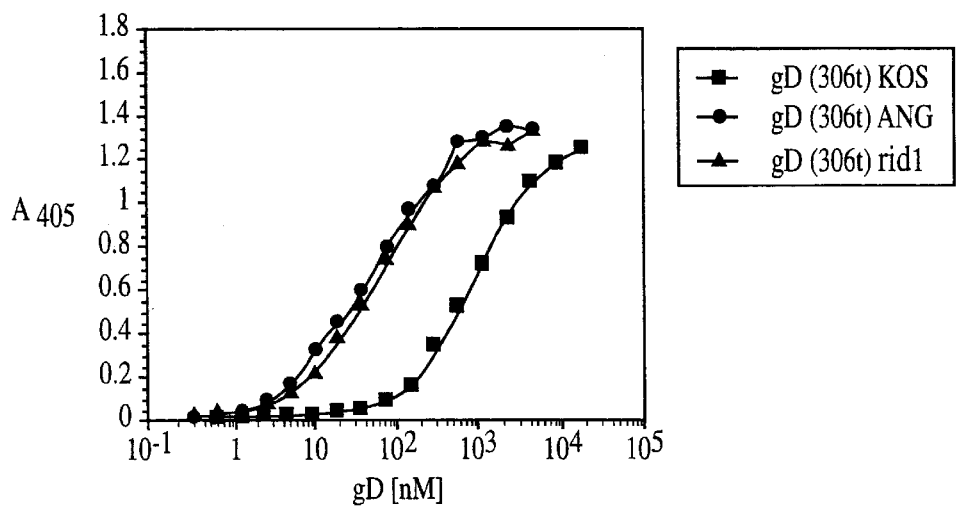

HSV-1 entry into CHO cells was enhanced by expression of HveC regardless of the HSV strain tested (Example 2 herein). In contrast, HveA expression did not render CHO cells permissive to infection with HSV strains such as rid1, rid2 and ANG (Montgomery et al., 1996, Cell. 87:427–436). The first two strains comprise a single mutation at amino acid 27 of gD (Q27P or Q27R respectively) allowing these viruses to escape from gD KOS-mediated interference (Dean et al., 1994, Virology 199:67–80). HSV-1(ANG) gD has three mutations in its ectodomain (L2SP, Q27R and T230I) as well as several in the cytoplasmic tail (Izumi et al., 1990, J. Exp. Med. 172:487–496). Truncated forms of gD(rid1t) and gD(ANGt) were produced in the baculovirus expression system and were antigenically characterized (Nicola et al., 1996, J. Virol. 70:3815–3822). These forms of gD, renamed gD(306t)rid1 and gD(306t)ANG for coherence, were tested for their binding to HveA and HveC in comparison with gD(306t)KOS (FIG. 16). Consistent with the infection data neither form of gD) interacted with HveA as shown previously (Whitbeck et al., 1997, J. Virol. 71:6083–6093; and FIG. 16B). In striking contrast, these two proteins exhibited an enhanced ability to bind HveCt as compared with binding of the control gD(306t)KOS (FIG. 16C). The shapes of the two curves were similar suggesting that all three forms of gD interacted similarly with HveC.

(ii) gD Mutated in Functional Regions.

Figures 1, 17A:
Figures 2, 17A:
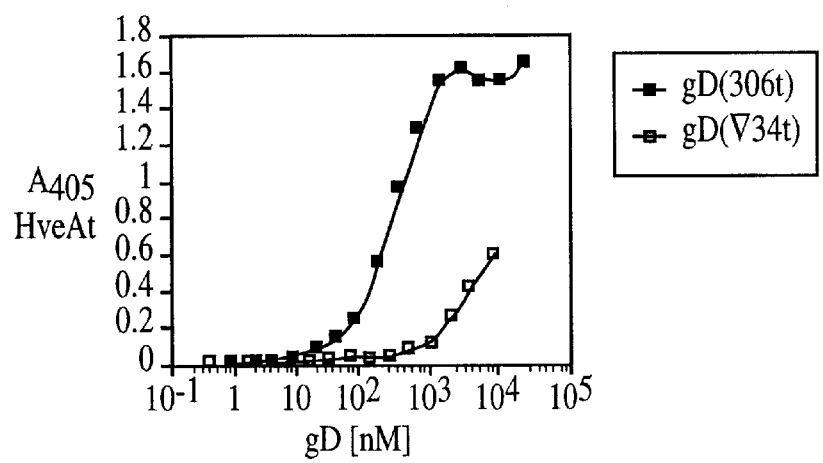
Figures 3, 17A:
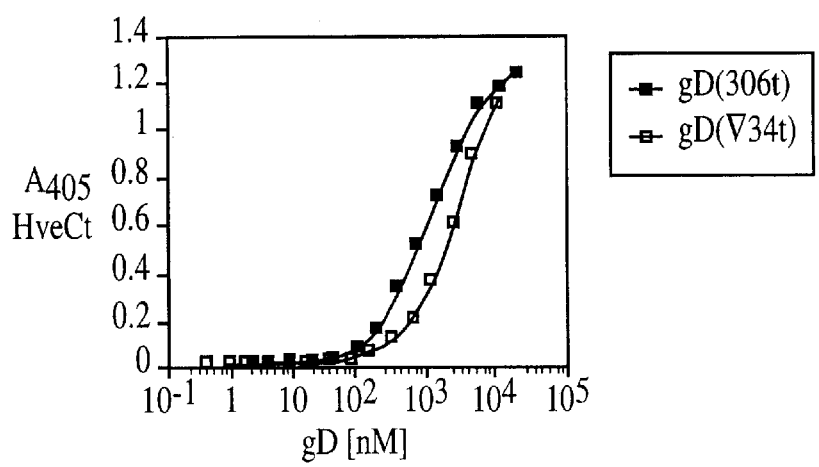
Figures 1, 17B:
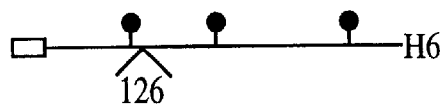
Figures 2, 17B:
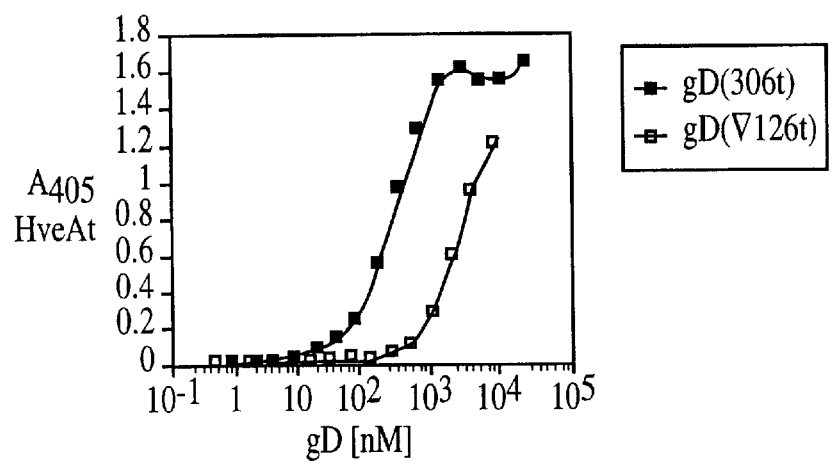
Figures 3, 17B:
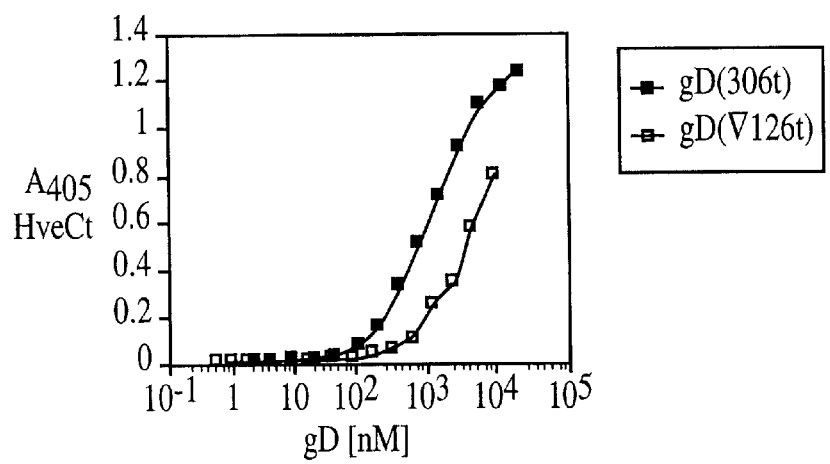
Figures 1, 17C:
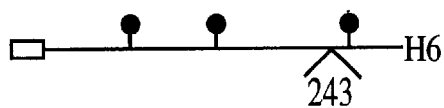
Figures 2, 17C:
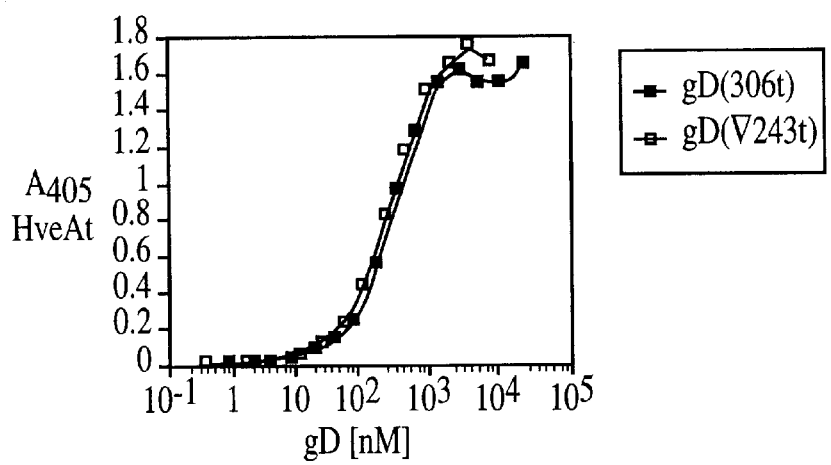
Figures 3, 17C:
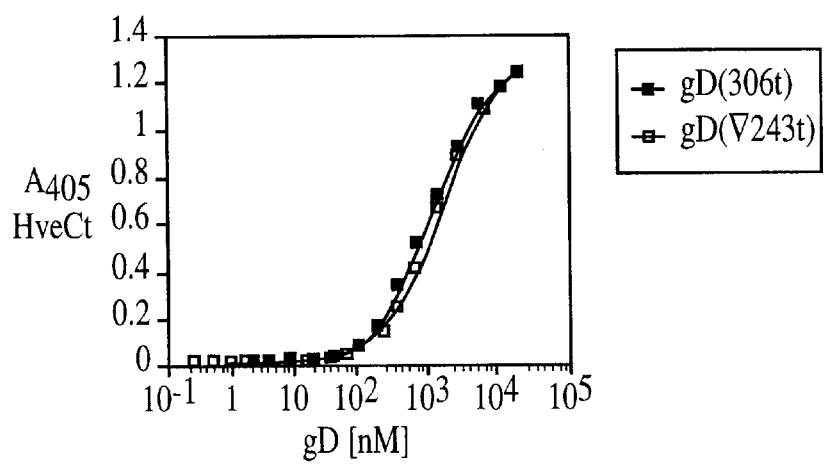
Figures 1, 17D:
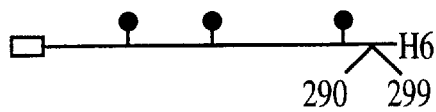
Figures 2, 17D:
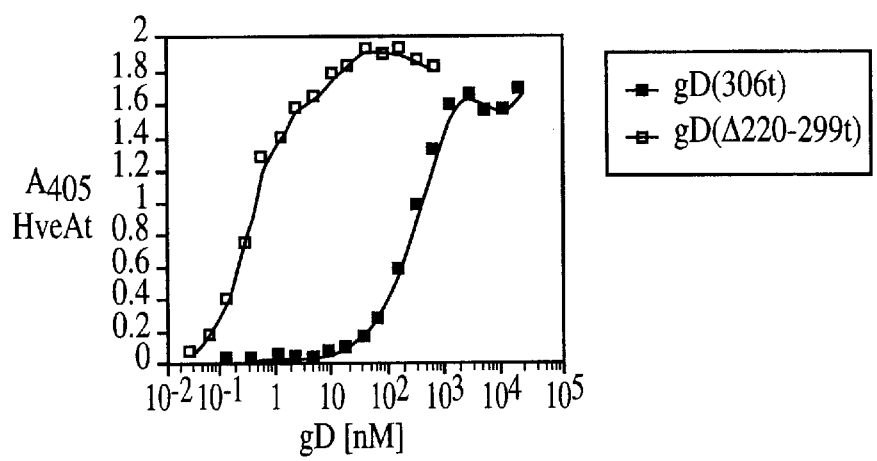
Figures 3, 17D:
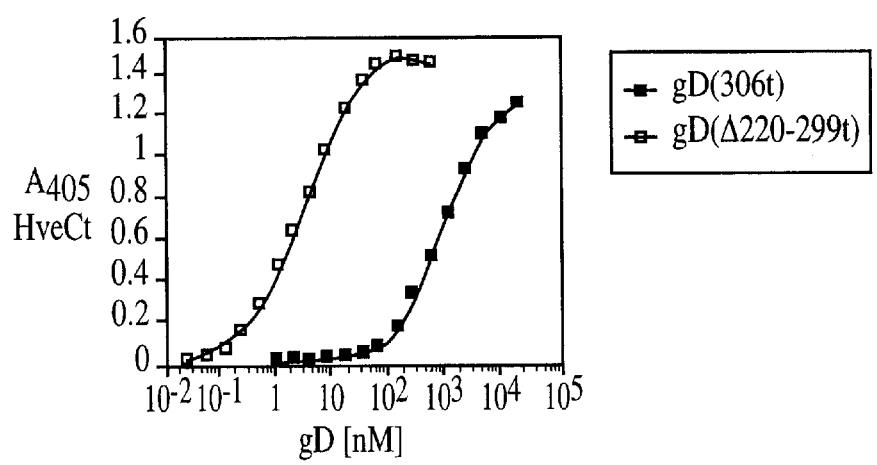

Four functional regions on gD have been identified by linker insertion mutagenesis based on the inability of the mutated full length glycoprotein to restore infectivity of a gD-null virus (Chiang et al., 1994, J. Virol. 68:2529–2543). Linker insertions after amino acids 34, 126 and 243 disrupted functional regions I, II and III respectively. Functional region IV was altered by the substitution of amino acids 290–299 with the linker. These mutated gDs were expressed by recombinant baculoviruses (Nicola et al., 1996, J. Virol. 70:3815–3822) and were tested for binding to HveCt (Willis et al., 1998, J. Virol. in press, July) and HveCt. Disruption of functional region I in gD(34t) very significantly reduced gD binding to HveAt whereas this mutation marginally affected binding to HveCt (FIGS. 17Ai and 17Aiii). The mutation in functional region II harbored by gD(-126t) induced a ten-fold decrease in binding to either HveCt or HveAt (FIGS. 17Bii and 17Biii). The gD(-243t) mutant (functional region III) displayed normal binding to both receptors (FIGS. 17Cii and 17Ciii). Thus, the inability of gD(-243) to perform its role during infection does not correlate with a defect in interaction with either receptor. gD(A290–299t), altered in functional region IV, was previously shown to exhibit enhanced binding to HveAt (Whitbeck et al., 1997, J. Virol. 71:6083–6093). Here, it was found that gD(A290–299t) was similarly enhanced in its binding to HveC (FIGS. 17Dii and 17Diii). For both receptors, binding was increased by approximately hundred-fold as compared to wild type gD(306t). Taken together, three of the four changes in gD had similar effects on binding to both cellular proteins. In contrast, the mutation in functional region 1 had very different effects on binding to HveA vs HveC confirming that integrity of this region is crucial for HveA binding (Montgomery et al., 1996, Cell 87:427–436; Nicola et al., 1998, J. Virol. 72:3595–3601; Whitbeck et al., 1997, J. Virol. 71 :6083–6093) but is not necessary for HveC binding.

(iii) C-terminal gD Truncations.

Figure 18A:
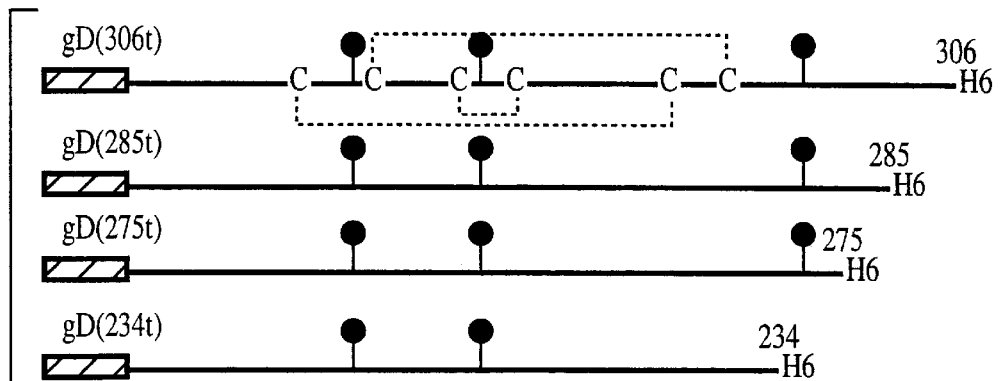
FIGS. 18A and 18B, depicts the effect of C-terminal truncation on binding to HveC.
Figure 18B:
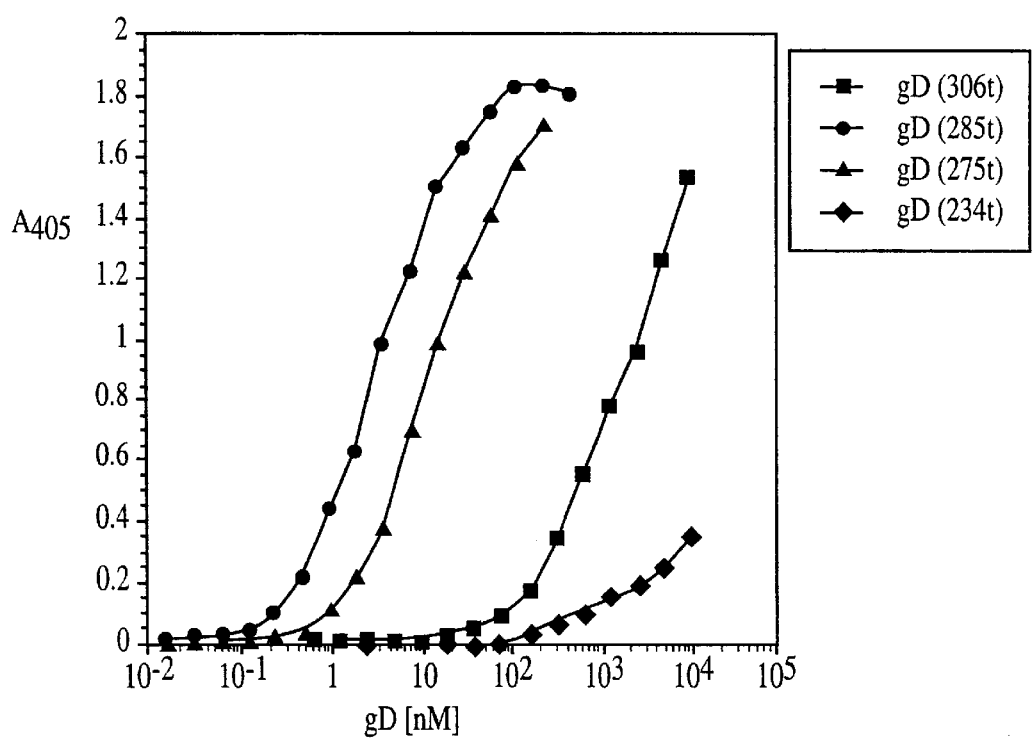

To further map the sites on gD involved in binding to HveCt, larger C-terminal truncations of HSV-1 gD (FIG. 18A) were generated (Mizukarni et al., 1998, Proc. Natl. Acad. Sci. USA 85:9273–9277) and were tested for HveCt binding by ELISA. Mutant gD(285t) lacking part of functional region IV showed an enhanced binding capacity as compared to gD(306t) (FIG. 18B). Similarly, the shorter version gD(275t) bound HveCt better than gD(306t) (FIG. 18B). In contrast, truncation after amino-acid 234 significantly decreased the ability of the shorter gD(234t) to bind HveCt (FIG. 18B). These data indicated that the region between amino acids 234 and 275 was crucial for binding to HveC whereas the region downstream of amino acid 285 altered binding with HveC and affected the affinity of the interaction. Similar observations have been made concerning the ability of HveA to bind with these truncated forms of gD.

Interaction of Soluble HveCt With gD at the Surface of Viral Particles

Figure 19A:
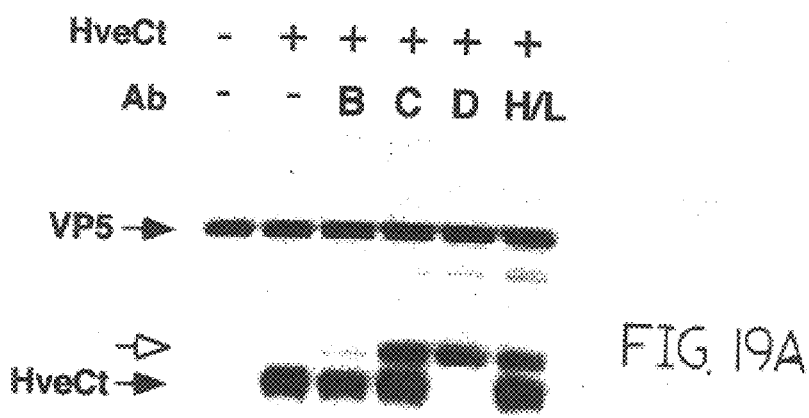
FIGS. 19A and 19B, is a pair of images depicting binding of HveCt to HSV particles is blocked by anti-gD antibodies.

After demonstrating binding of HveCt with truncated gD by ELISA, the interaction of HveCt with gD on the surface of viral particles was, analyzed. It has been established herein in Example 2 that incubation of purified HSV-1KOS virions with soluble HveCt block virus entry. To assess direct binding of soluble HveCt to viral particles, the cosedimentation assay developed by Nicola et al. (1998, J. Virol. 72:3595–3601) was used to study the HveAt-HSV interaction. Here, HveCt was cosedimented with purified virions through a sucrose step gradient. The virus band at the 30–60% sucrose boundary was collected and analyzed by Western blot (FIG. 19). The presence of the virus in this fraction was demonstrated by probing the blot for the major capsid protein VP5. HveCt was also detected in this fraction when incubated with the virus prior to centrifugation (FIG. 19A, lane 2) indicating that HveCt bound directly to virions. To confirm that gD is the target for HveC binding to virions, the blocking of the HveCt-virion interaction was attempted using antibodies directed against several HSV-1 glycoproteins. Identical aliquots of purified virions were pretreated separately with cocktails of monoclonal and polyclonal antibodies directed against gB, gC, gD or gH/gL (FIG. 19A, lanes 3–6). Only anti-gD antibodies prevented cosedimentation of HveC with virus, as revealed by the absence of HveC in the virus fraction (FIG. 19A, lane 5). Antibodies directed against gB, gC or the gH/gL complex did not compete with HveCt. Thus, gD is the target for HveCt binding on the viral envelope.

Figure 19B:
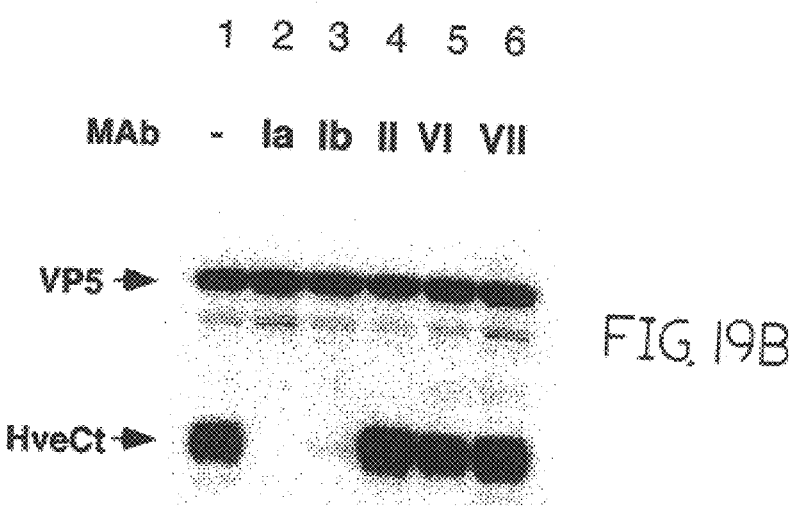

The same cosedimentation assay was used to define which regions of gD were important for HveC binding. MAb IgGs that recognize distinct antigenic sites of the gD molecule were used to pretreat virions before incubation with HveCt (FIG. 19B). MAbs HD1 and DL11, from antigenic groups Ia and Ib respectively, prevented attachment of HveCt to viral particles (FIG. 19B, lanes 2 and 3). In contrast, MAbs DL6, DL2 and 1D3 mapping to antigenic sites II, VI and VII, respectively, did not affect HveCt binding to purified virions (FIG. 19B, lanes 4–6). This suggests that antigenic sites Ia and Ib on gD overlap regions important for HveC binding. The pattern of blocking by this panel of MAbs is different from that observed previously for HveAt in that HveAt binding to virion was blocked by MAbs in groups Ib and VII but not Ia (Nicola et al., 1998, J. Virol. 72:3 595–3601).

gD-HveCt Complex Formation in Solution

The capacity of purified gDt and HveCt to form a complex in solution was investigated. In this assay, the high affinity gD(A290–299t) and HveCt were incubated together in PBS overnight at 4° C. prior to loading on a gel filtration column (Superdex 200). Eluted fractions were collected and were subjected to Western blot analysis. Membranes were probed for gD (FIG. 20A) or HveC (FIG. 20B). Since R7 anti-gD polyclonal serum is much more sensitive than R145 anti HveC-peptide serum, direct quantitative comparison of band intensities between panels A and B is not possible. When gD(A290–299t) was run alone on the Superdex column it eluted with an apparent size of 61 kDa (FIG. 20A, panel 1) confirming the formation of a dimer in solution (Eisenberg et al., 1982, J. Virol. 41:1099–1104). When equimolar amounts of HveC and gD were mixed, gD eluted at a higher molecular weight (176 kDa) and coeluted with HveC (FIGS. 20A and 20B, panel 2). This shift in gD elution probably reflected the formation of a gD-HveC complex in solution as reported for other protein-protein interactions (Cunningham et al., 1991, Science 254:821–825). To begin to address the question of stoichiometry of both components in this complex, the same approach used to analyze the gD-HveA soluble complex was followed (Whitbeck et al., 1997, J. Virol. 71 :6083–6093). Here, HveCt and gD(Δ290–299t) were mixed at various molar ratios prior to gel filtration and column fractions were analyzed by Western blot. When gD(Δ290–299t) was mixed with HveCt at a 2:1 molar ratio (FIG. 20 panel A3 and B3 FIGS. 20A and 20B, panel 3), the majority of the gD again co-eluted with HveC at a higher molecular weight. A limited amount of free gDt (dimer) was also detected by Western blotting but no gD peak (A280) was visible on the elution profile. In contrast, when the molar ratio of gDt:HveCt was 3:1(FIGS. 20A and 20B, panel 4), a significant excess of free gD dimers was detected in fractions 30 to 33(FIG. 20A, panel 4) corresponding to a now visible A280 peak of free gDt. While not wishing to be bound by theory, a simple interpretation of the data is that, at an initial ratio of 2 gDt: 1 HveCt, the maximal amount of gD that could be incorporated in the complex was present, leading to a nominal amount of free gDt (Cunningham et al., 1991, Science 254:821–825). This would suggest a stoichiometry close to 2 gDt: 1 HveCt in the complex formed in solution. Quantification of silver stained proteins in the complex (fractions 26, FIGS. 20A and 20B, panels 3 and 4) after SDS-PAGE indicated a gD:HveCt ratio of 1.6 to 1. This indicated that as many as two gD might bind on each HveC, although saturation of the receptor in solution was difficult to achieve under these conditions. In any case, this ratio was very different from the 1 gD:2 HveA ratio determined previously for the interaction of gD with HveA under similar conditions (Whitbeck et al., 1997, J. Virol. 71 :6083–6093). One observation was that the apparent size of the gD-HveCt complex was not significantly larger than HveC alone unless gD was in excess. One possibility is that HveCt conformation and/or oligomerization was altered by gD binding such that its elution properties changed. For instance a two-dimer complex of HveCt (176 kDa, FIG. 20B, panel 1) could be disrupted upon binding to gD to form a complex of one HveCt dimer and 2 gD dimers with a calculated size of 210 kDa (212 kDa observed)(FIGS. 20A and 20B, panel 4). Since HveC is highly glycosylated it could also be possible that these posttranslational modifications have different effects on HveC elution in the presence or absence of gD.

EXAMPLE 4

Data Which Establishes that the First Ig-like Domain of HveC is Sufficient to Bind HSV gD With Fullaffinity while the Third Domain is Involved in Oligomerization of Hvec As stated herein, the human herpesvirus entry mediator C (HveC/PRRI) is a member of the immunoglobulin family used as a cellular receptor by the alpha herpesviruses HSV, PRV, BHV-1. The data presented elsewhere herein demonstrate direct binding of the purified HveC ectodomain to purified HSV-1and HSV-2 glycoprotein D (gD). Here, using a baculovirus expression system, truncated forms of the receptor containing 1 [HveC(143t)], 2 [HveC(245t)] or all 3 Ig-1 ike domains [HveC(346t)] of the extracellular region have been constructed and purified. All three constructs were equally able to compete with HveC(346t) for gD binding. The V-domain bound to virions and blocked HSV infection as well as HveC(346t). Thus, all of the binding to the receptor occurs within the first Ig-1 ike domain, or V-domain, of HveC. Using biosensor analysis, the affinity of binding of gD from HSV strains KOS and rid1 to two forms of HveC was analyzed. Soluble gDs from the KOS strain of HSV-1 had the same affinity for HveC(346t) and HveC (143t). The mutant gD(rid1t) had an increased affinity for HveC(346t) and HveC(143t) due to a faster on rate of complex formation. Interestingly, it was discovered that HveC(346t) was a tetrameter in solution whereas FveC (143t) and HveC(245t) formed dimers, suggesting a role for the third Ig-like domain of HveC in oligomerization. In addition, the stoichiometry between gD and HveC appeared to be influenced by the level of HveC oligomerization.

The data presented in the present Example demonstrate that a protein containing just the single V-domain of HveC and a protein containing the two distal domains of HveC are each able to bind to soluble gD as efficiently as the whole HveC ectodomain. The HveC V-domain protein bound to virus and was also able to block HSV infection of several human neuron-like cell lines as efficiently as the full ectodomain. Surface plasmon resonance (SPR) technology was used to determine that both soluble receptors display similar affinity to several forms of HSV-1 gD. Moreover both the on rates and of f rates of gD:HveC complex formation were very similar. Interestingly the single V-domain protein and the two-domain protein were dimers in solution whereas the complete ectodomain was a tetrameter under the same conditions. This indicated the possibility of several levels of oligomerization of HveC involving at least the first and the third domains.

The Materials and Methods used in this Example are now described.

Cells and viruses: Spodoptera frugiperda Sf9) cells (GIBCO BRL) were maintained in suspension in Sf900II medium or as monolayer cultures in supplemented Grace's medium (GIBCO BRL) with 10% fetal calf serum (FCS). CHO M3A cells are derived from CHO-IEβ8 expressing the β-galactosidase gene under the control of the viral ICP4 promoter (Montgomery et al, 1996, Cell 87:427–436; Terry-Allison et al., 1998 Journal of Virology 72:5802–5810) and express constitutively the full length human HveC under the control of a CMV promoter. M3A cells were grown in HAM's F12 medium supplemented with 10% FCS, 250 μg/ml G418 and 300 μg/ml puromycin. IMR5, SY5Y (human neuroblastoma cell lines), were grown in DMEM with 10% FCS. 5 HSV-1 KOS 1112(Montgomery et al., 1996, Cell 87:427–436) and HSV-1 rid1 tk12 were purified from infected Vero cells and titered on Vero cells.

Glycoproteins and antibodies: Soluble glycoproteins such as gD(306t), gD(285t), were derived from HSV-1strain KOS unless otherwise noted, gD)-2(306t) was from HSV-2 strain 333 and gD(rid1t) from HSV-1 strain rid1. Construction and purification of these proteins from baculovirus infected cell supernatant was described elsewhere (Nicola et al., 1997, J. Virol. 71 :2940–2946; Nicola et al., 1996, D. J. Virol. 70:3815–3822; Rux et al., 1998, Journal of Virology 72:7091–7098; Sisk et al., 1994, 1. Virol. 68:766–775). Rabbit polyclonal serum R7 was raised against HSV-2 gD purified from infected mammalian cells (Isola et al., 1989, D. J. Virol. 63:2325–2334). Anti tetra-His MAb was purchased from Qiagen Inc. (Valencia, Calif.). Anti HveC MAb R1.302 is disclosed in (Lopez et al., 1997, In: Identification of a new class of IgU superfamily antigens expressed in hematopoiesis, pp. 1081–1083, Garland Publishing ed., New York) was kindly provided by S. McClellan, Beckman/Coulter (cOCCHI ET AL., 1998, j. VIROL. 72:9992–10002).

Construction of recombinant baculoviruses and purification of soluble receptors. The strategy to generate soluble HveC(346t) was described previously herein and in (Willis et al., 1998 In: S. M. Brown and A. R. Mac Lean ed, Methods in Molecular Medicine, vol. 10, Herpes Simplex Virus Protocols, Huniana Press Inc., Totowa, N.J.) and applied here to generate all HveC constructs. The plasmid pBG38 was used as template for PCR amplification using the upstream primer (C5) 5'-GCGTGATCA-GGTGGTCCAGGTGAACGACTCCATGTAT-3' (SEQ ID NO:24) and the downstream primer 5'-CGGCCCGGGCTAATGATGATGATGATGATGCTGC-ACGTTGAGAGTGAGG CTTTCC-3' (SEQ ID NO:25) for HveC(245t) or 5'-CGGCCCGGGCTAATGATGATGA-TGATGATGCATCACCGTGAGAflGAGCTGGCTTTCT-3' (SEQ ID NO:26) for HveC(143t). The cloning strategy using the vector pVTBac was described earlier herein and in (Willis et al., 1998 hi: S. M. Brown and A. R. Mac Lean ed, Methods in Molecular Medicine, vol. 10, Herpes Simplex Virus Protocols, Humana Press Inc., Totowa, N.J.) and plasmids pCK329 and pCK330, respectively, were generated and used to produce recombinant baculoviruses bac-HveC(245t) and bac-HveC(143t). HveC(245t) contains amino acids 31–245 from human HveC with an extra aspartic acid residue at the N-terminus and a 6-histidine tail at the C-terminus of the protein added during the amplification and cloning process. HveC(143t) contains amino acids 31 to 143 of human HveC with the same C- and N-terminal additions.

All soluble receptors, containing a C-terminus 6-histidine tag, have been purified by nickel affinity chromatography (Ni-NTA superfiow, Qiagen Inc., Valencia, Calif.) as described previously herein and in (Whitbeck et al., 1997, J. Virol. 71:6083–6093; Willis et al., 1998 In: S. M. Brown and A. R. Mac Lean ed, Methods in Molecular Medicine, vol. 10, Herpes Simplex Virus Protocols, Humana Press Inc., Totowa, N.J.). Purified soluble HveC proteins were dialyzed against 100 mM sodium phosphate pH 8.0, 150 mM NaCl and concentrated.

Enzyme-1 inked immunosorbent assay (ELISA): I) A standard ELISA 20 using immobilized receptor and soluble gD was described previously herein. ii) Competition ELISA: HveC(346t) at 10 μg/ml in phosphate-buffered saline (PBS) was adsorbed to microtiter plates for 2 hours at room temperature (RT) Plates were washed with 0.1% Tween 20 in PBS and blocked with 5% milk, 0.2% Tween-20 in PBS (PBST-milk) for 1 hour at room temperature. Plates were then incubated overnight at 4° C. with PBST-milk containing a constant concentration of gD and variable concentrations of soluble receptors as competitors. The plates were washed and the bound gD was detected with R7 antiserum (diluted 1:1000 in PB ST-milk) for 1 hour followed by goat anti-rabbit IgG coupled to horseradish peroxidase (diluted in 1:1000 in PBST-milk) for 30 minutes. The plates were washed with 20 mM citric acid pH 4.5 prior to the addition of substrate (ARTS, Moss Inc.). Absorbance was read at 405 nm.

Blocking assay: Cells were grown to confluence in 96-well plates in their respective medium and chilled for 15 minutes at 4° C. prior to the addition of virus. HSV-1 KOS tk12 or HSV-1 rid1 tk12 was preincubated with soluble receptors at varying concentrations in cold medium containing 30 mM HEPES for 90 minutes. Culture medium was removed and 100 μl of virus containing medium was added (MOI=1 pfu/cell). Cells were then incubated at 37° C. for 5 to 6 hours and lysed in NP-40(0.5% final). Fifty μl of cell lysate was mixed with an equal volume of β-galactosidase substrate (chlorophenol red-β-galactopyranoside). The level of virus entry was monitored by reading absorbance at 595 nm for 50 min to record enzymatic activity expressed as ΔAOD/hour. Blocking activity of soluble receptors is expressed as the percentage of virus entry into cells under test conditions as compared to viral infection in absence of inhibitor (100%).

Gel filtration: Purified proteins were diluted in PBS and loaded onto a Superdex 200 column (Pharmacia HR 10/30) as described previously herein.

Electrophoresis: Non-denaturing and non-reducing PAGE has been described previously (Cohen et al., 1986, J. Virol. 60:157–166). Proteins were separated on precast Tris-glycine gels (Novex) using 200 mM glycine, 25 mM Tris base, 0.1% SDS as running buffer. Proteins were then visualized by silver staining of the gel (Pharmacia Silver Stain Kit) or transferred to nitrocellulose prior to antibody detection.

Binding of HveC to virus: Soluble receptor (100 μg) was mixed with $10^7$ PFU of purified HSV-1 KOS (about $4\times10^8$ particles) or $10^7$ PFU of purified HSV-1 rid1 (about $3\times10^8$ particles) in 150 μl PBS for 90 minutes at 4° C. The virus was subjected to sedimentation through a sucrose step-gradient (10–30–60%) for 4.5 hours at 16000×g. The viral band was then collected and analyzed by western blots as described previously herein and in (Nicola et al., 1998, J. Virol. 72:3595–3601) using anti tetra-His (Qiagen Inc., Valencia, Calif.) and anti-VPS antibodies.

Measurement of binding of gD to HveC with an optical biosensor: Biosensor experiments were carried out on a Biacore X optical biosensor (Biacore AB) at 25° C. following the protocol previously described (Rux et al., 1998, Journal of Virology 72:7091–7098; Willis et al., 1998, J. Virol. 72:5937–5947) with the following modifications. The running buffer was HBS-EP (10 mM HEPES, 150 mM NaCl, 3 mM EDTA, 0.005% polysorbate 20), pH 7.4. Approximately 1600 response units (RU) of HveC(346t) or 300 RU of HveC(143t) were coupled to flow cell I (Fc1) of a CMS sensor chip via primary amines according to the manufacturer's specifications. Fc2 was activated and blocked without the addition of protein. Soluble gD was serially diluted in HBS-EP. Each gD sample was injected for 2 min to monitor association. Then the sample was replaced by HBS-EP flow, and the dissociation was monitored for 2 minutes. During the binding and dissociation phases of gD to HveC, the flow path was set to include both flow cells, the flow rate was 50 µl/min and the data collection rate was set to high (5 measurements /mm). To regenerate the HveC surface, brief pulses of 0.2 M $Na_2CO_3$, pH 10, were injected until the response signal returned to baseline. Sensorgrams were corrected for non-specific binding and refractive index changes by subtracting the control sensorgram (Fc2) from the HveC surface sensorgram (Fc1). Data were analyzed with B1Aevaluation software, version 3.0, (Biacore, Inc., 1997 B1Aevaluation software handbook, version 3.0, Uppsala, Sweden) Model curve fitting 20 was done by using a 1:1 Langmuir interaction with drifting baseline. This models the simple interaction between ligand and receptor following L+R (LR. The rate of association ($k_{on}$) was measured from the forward reaction, and $k_{off}$ was measured from the reverse reaction (Biacore, Inc., 1997 B1Aevaluation software handbook, version 3.0, Uppsala, Sweden).

The Results of the experiments presented in this Example are now described.

Figure 21A:
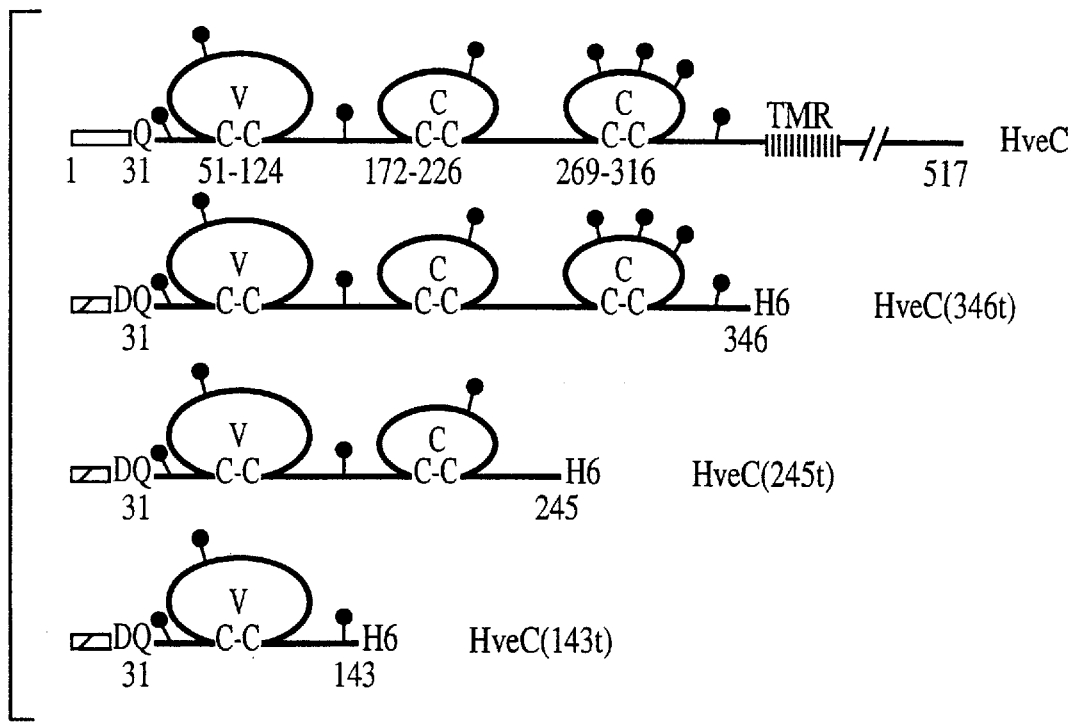
FIGS. 21A and 21B, is a schematic representation of HSV receptors (FIG. 21A) and gD constructs (FIG. 21B). Full length HveC is shown as a solid line with amino acids numbered from the initial methionine. The white box of FIG. 21A indicates HveC natural signal peptides. gD from HSV-1KOS is represented with amino acids numbered from the N-terminus of the mature gD after cleavage of the gD signal peptide (white box of FIGS. 21B). Disulfide bonds are indicated by dotted lines. The black lollipops represent putative N-1 inked carbohydrates. The hatched box represents the mellitin signal peptide used in the baculovirus constructs. Baculovirus-expressed proteins are truncated (t) at the indicated amino acid prior to the transmembrane region (TMR). H6, six-histidine tag added at the C-terminus.
Figure 21B:
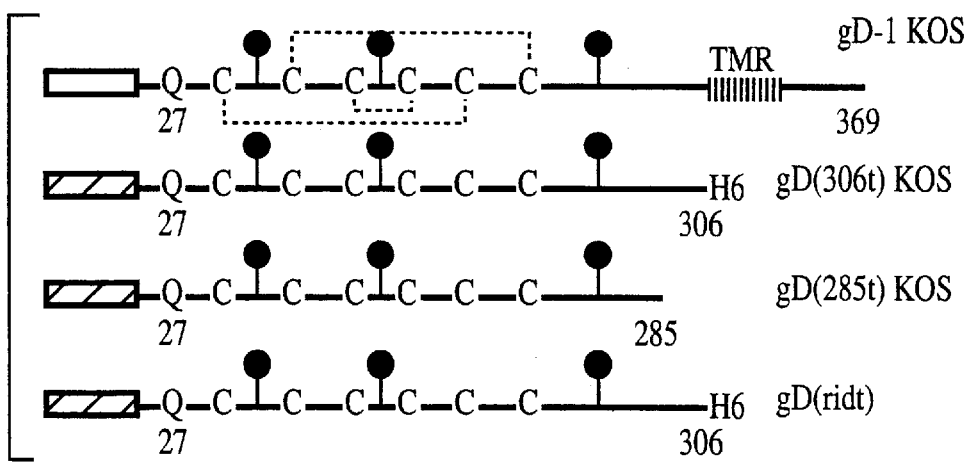
Figures 22A, 22B, 22C:
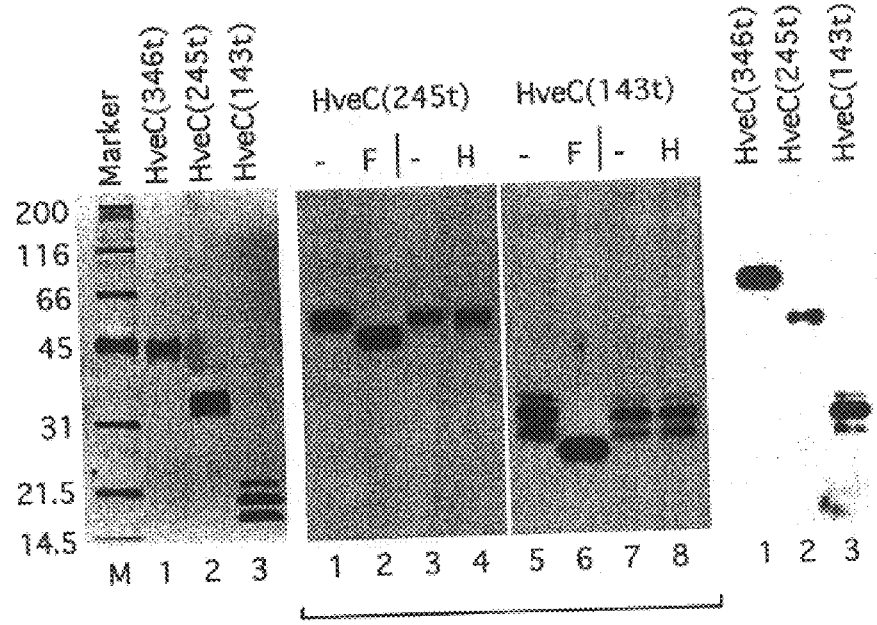
FIGS. 22A, 22B, and 22C, is a series of images of gels, depicting purified soluble receptors. Receptors purified from recombinant baculovirus infected Sf9 cell supernatants were separated by PAGE.

Production and characterization of baculovirus-expressed HveC receptors. Soluble receptors were purified from supernatant of recombinant baculovirus infected 519 cells. HveC (143t) contains the N-terminal Ig-1 ike V-domain, and HveC(245t) encompasses two N-terminal domains (FIG. 21). Their properties were compared to the previously described HveC(346t) herein, which includes all three Ig-domains of HveC and ends just before the transmembrane region (FIG. 21). As shown previously, HveC(:346t) migrated as a 45 kDa glycoprotein by SDS-PAGE, although mass spectrometry revealed a molecular weight of 40 kDa herein. HveC(245t) migrated as a heterogeneous glycoprotein of 33 to 34 kDa (FIG. 22A). Its molecular weight, determined by mass spectrometry was 28.0 kDa for the main species carrying three N-1 inked oligosaccharides (N—CHO); minor products with 2 or 4 N—CHO were also present. In SDS-PAGE, HveC(143t) migrated as three bands probably representing the protein with one, two or three N-1 inked carbohydrates. The apparent sizes were 17, 19 and 22 kDa respectively (FIG. 22A). Mass spectrometric analysis of HveC(143t) detected two major products of 14.5 and 15.6 kDa as well as a minor product of 16.7 kDa. The observed increment of size correlated with the addition of one N-1 inked carbohydrate chain in insect cells (Kuroda et al., 1990, Virology 174:418–429; Rux et al., 1996, 1996, J. Virol. 70:5455–5465). In both cases treatment of HveC(245t) and HveC(143t) with glycopeptidase F yielded a single faster-migrating band (FIG. 22B). All N—CHO on HveC(143t) were resistant to endoglycosidase H, whereas N—CHO on HveC(245t) were partially sensitive (FIG. 22B). Thus, the endoglycosidase data suggest that the oligosaccharide on Asn 202 present in HveC(245t) but not HveC(143t) might not be processed from the high-mannose type to the complex type. The presence of three glycosylated forms of HveC (143t) indicated that 3 N—CHO consensus attachment sites were used. A fourth Asn residue proposed as an N—CHO attachment site in the original sequence of HveC/PRRI (Lopez et al., 1995, Gene 155:261–265) at position 82 in an Asn-Pro-Ser pseudo-consensus site is probably not glycosylated.

Figure 23A:
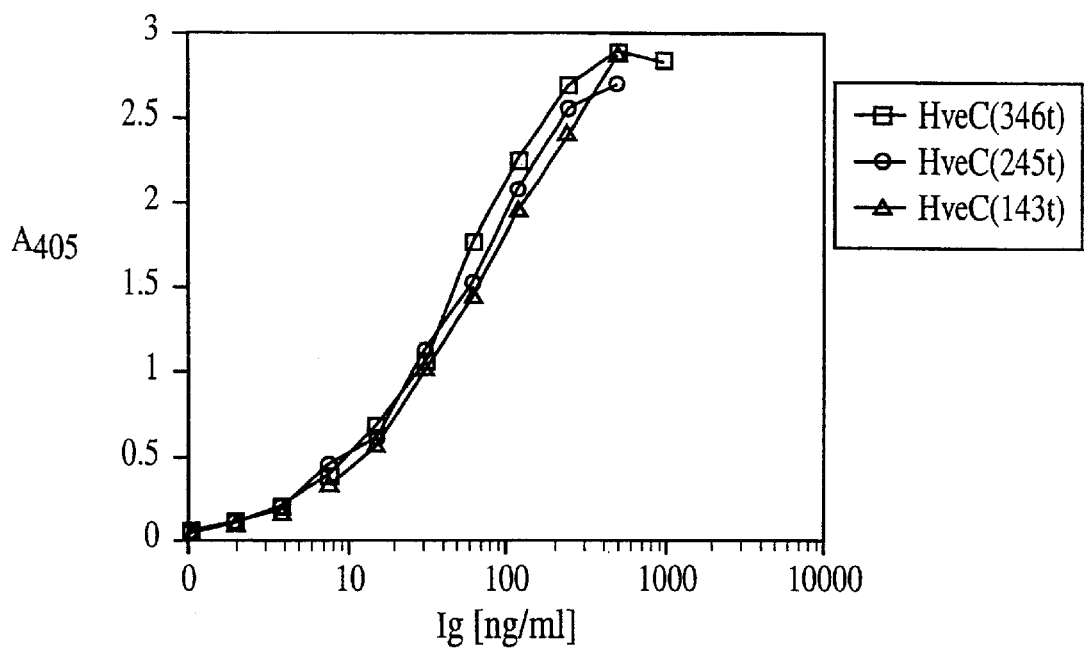
FIGS. 23A and 23B, is a series of graphs depicting detection of HveC truncations with MAbs by ELISA. Detection of immobilized truncated HveC proteins with anti tetra-His Ig (Qiagen. Inc.
Figure 23B:
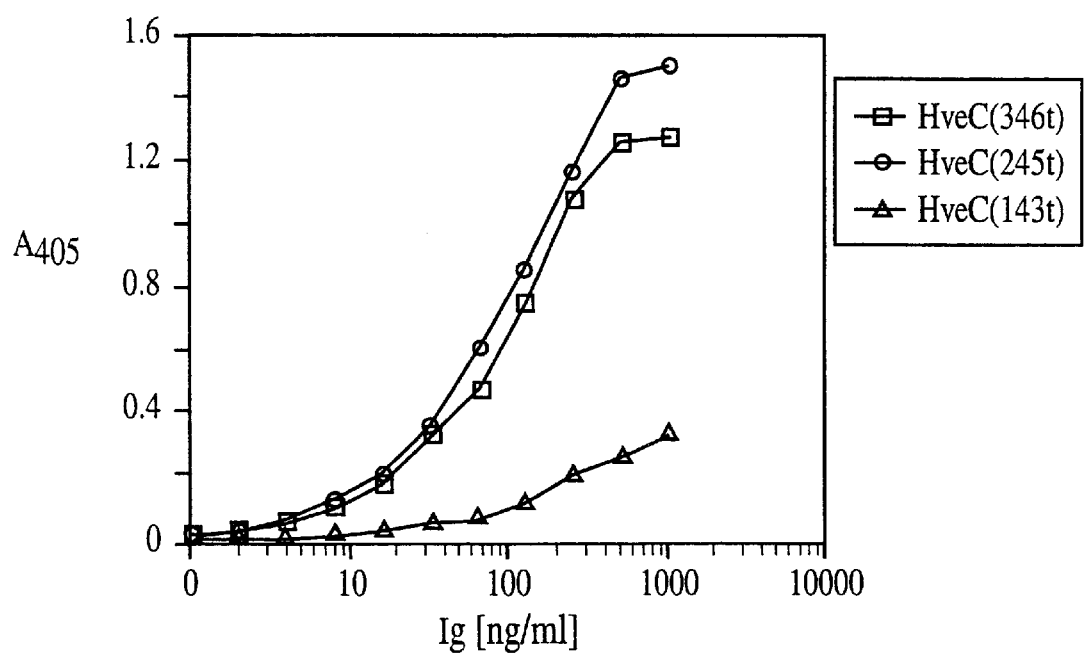

Detection of HveC truncations with MAbs. The NIAb R1.302 binds to the single V-domain of HveC on cells and blocks virus entry (Cocchi et al., 1998, Proc. Natl. Acad. Sci. USA 95:15700–15705; Cocchi et al., 1998, J. Virol. 72:9992–10002). This neutralizing MAb was used to probe a native western blot of the three soluble HveC proteins (FIG. 22C). The antibody detected each receptor including all 3 glycosylated forms of HveC(143t). Detection of HveC (143t) by MAb R1.302 was abolished when PAGE was performed under reducing and denaturing conditions. This indicated that Ri 0.302 recognized a non-1 linear epitope on HveC(143t) and that the purified proteins, including the one domain HveC(143t), were correctly folded. The native conformation of HveC truncations was also tested in an ELISA (FIG. 23). As expected, all truncated forms of HveC reacted similarly with the anti tetra-His antibody, indicating that comparable amounts of proteins had been immobilized (FIG. 23A). In the same setting, MAb R1.302 was used to detect a conformation dependent epitope on truncated HveC immobilized on an ELISA plate (FIG. 23B). Both HveC (346t) and HveC(245t) reacted with similar efficiency. In contrast HveC(143t) was less efficiently recognized by this MAb, suggesting a loss of conformation of this small HveCt.

Figure 24A:
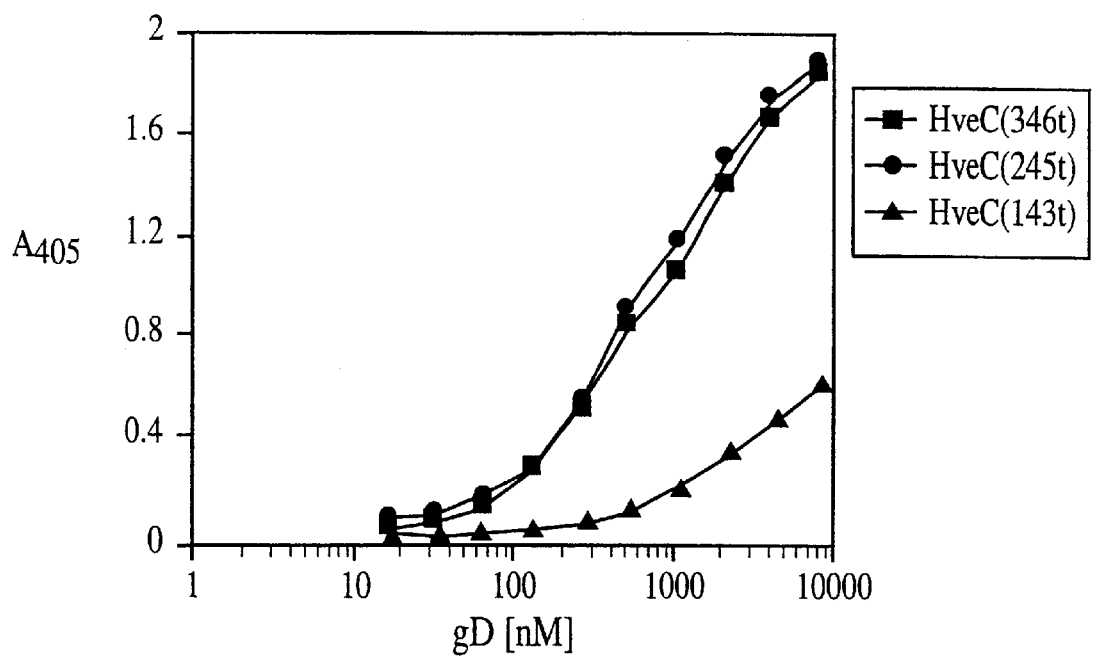
FIGS. 24A and 24B, is a series of graphs depicting direct ELISA. Plates coated with HveC truncated proteins at 200 nM in PBS were incubated with increasing concentrations of gD(306t) (FIG. 24A) or gD(285t) (FIG. 24B) from HSV-1strain KOS. Bound gD was detected with R7 antiserum followed by peroxidase-conjugated secondary antibody and substrate. Absorbance was read at 405 nm.
Figure 24B:
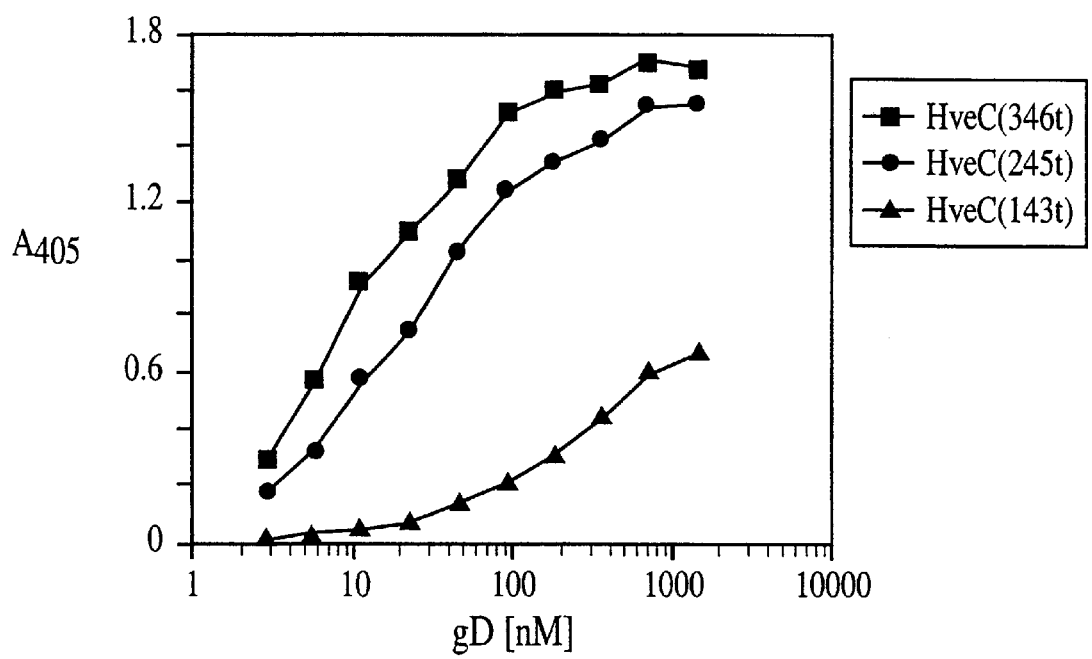

Interaction of truncated HveC with gD by ELISA. HveC (346t) has the ability to bind gD directly in an ELISA herein. In this experiment, the binding of smaller truncations of HveC to gD by ELISA was analyzed. First, the level of binding of gD to the immobilized forms of HveCt was tested. Varying concentrations of soluble gD(306t) (FIG. 24B) were allowed to bind to each immobilized HveC form. Bound gD was then detect:ed using polyclonal R7 serum (FIG. 24A). gD(306t) bound to both HveC(346t) and HveC (245t) with similar efficiency indicating that the most C-terminal Ig domain is dispensable for the interaction of HveC with gD. However, gD(306t) bound less efficiently to HveC(143t). The shorter gD(285t) which displays an enhanced binding affinity for HveC over that of gD(306t) (see below and Rux et al., 1998, Journal of Virology 72:7091–7098) bound to HveC(143t) with reduced ability as compared with HveC(346t) and HveC(245t) (FIG. 24B).

Figure 25A:
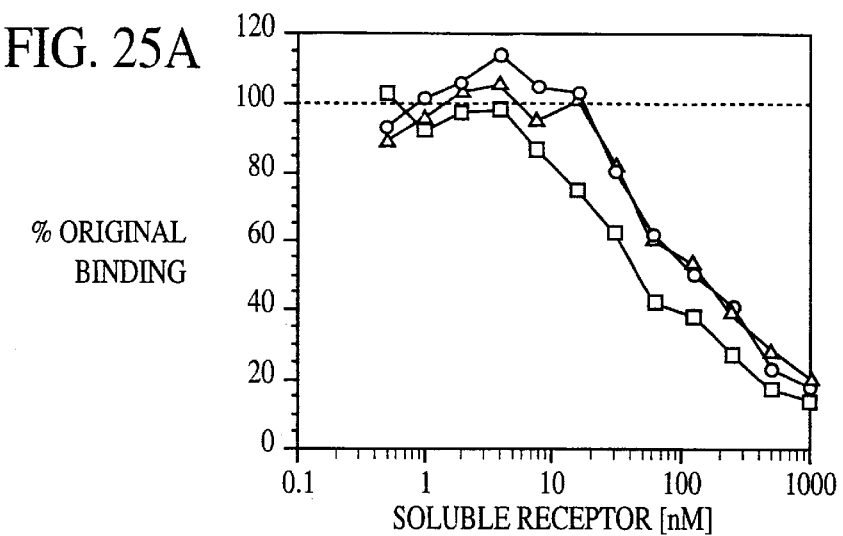
FIGS. 25A, 25B, and 25C, is a series of graphs depicting competition ELISA. Plates were coated with HveC(346t) and incubated with a constant amount of purified gD together with increasing concentrations of HveC truncated receptors as competitors. 1 µM gD-1(306t) from HSV-1 KOS, (FIG. 25A) 0.1 µM gD-1(rid1t) and (FIG. 25B) 1 µM gD-2(306t) from HSV-2 strain 333(FIG. 25C). gD) bound to the immobilized receptor was detected with R7 antiserum. In these figures, squares correspond to data relating HveCt(346t), circles correspond to data relating to HveC(245t), and triangles correspond to data relating to HveC(143t).

Binding of HveC truncations with PD in solution. The ability of each truncated HveC to bind gD by ELISA correlated with its capacity to be recognized by the conformation-dependent neutralizing MAb R1.302. Since heat denatured HveC(346t) completely failed to bind gD by ELISA, the decreased binding ability of HveC(143t) might reflect a partial denaturation that could have occurred during purification or because of immobilization on the ELISA plate. To clarify this point, a competition ELISA was performed where the binding between gD and the three receptor forms occurred in solution. In this experiment, HveC(346t) was immobilized on the plate. Then a constant amount of soluble gD(306t) corresponding to the half-saturating concentration for the bound HveC(346t) was added in the absence or presence of one of the soluble receptors which acts as a competitor for binding of gD (FIG. 25A). Soluble HveC(346t), HveC(245t) or HveC(143t) competed for binding of gD(306t) to the immobilized HveC(346t) in a dose dependent manner. Both soluble HveC(245t) and HveC (143t) were able to compete gD binding nearly as well as soluble HveC(346t) which competes with itself on the plate for gD binding.

HveC(346t) is also known to bind gD from HSV-2 and gD derived from the mutant HSV-1 rid1 herein and Whitbeck et al., 1997, J. Virol. 71:6083–6093). The rid1 form of gD has a point mutation at position 27 which prevents its binding to HveA but enhances its binding to HveC in an ELISA herein and Whitbeck et al., 1997, J. Virol. 71:6083–6093). Using the competition assay, the binding of soluble gD(rid1t) from the rid1 strain of HSV-1(FIG. 25B) and of gD-2(306t) from HSV-2 strain 333(FIG. 25C) to truncated HveC forms was In the case of HveC(143t), the V-domain alone, its affinity for the various forms of gD followed the same trend. gD(306t) having a KD of $1.2 \times 10^{-6}$ M had the lowest affinity and gD(285t) ($K_D = 3.5 \times 10^{-8}$ M) exhibited the highest affinity. Again, the variation in affinity was caused primarily by changes in the rate of complex formation. In addition, gD(rid1t) exhibited an intermediate affinity for HveC(143t). Both HveC(346t) and HveC(143t) displayed similar affinity to HveC(285t) or HveC(rid1t) with no significant differences in either on or off rates, whereas gD(306t) appeared to have a slightly higher affinity for HveC(346t) than HveC(143t).

TABLE 2

Kinetic and affinity values for HveCT-gDt complex formation

| | gD (306t) KOS | | | gD (285t) KOS | | | Gd (306T) rid1 | | |
|---|---|---|---|---|---|---|---|---|---|
| | $k_{on}$ ($10^3$ s$^{-1}$ M$^{-1}$) | $k_{off}$ ($10^{-2}$ s$^{-1}$) | $K_D^a$ ($10^{-6}$M) | $k_{on}$ ($10^3$ s$^{-1}$ M$^{-1}$) | $k_{off}$ ($10^{-2}$ s$^{-1}$) | $K_D$ ($10^{-6}$M) | $k_{on}$ ($10^3$ s$^{-1}$ M$^{-1}$) | $k_{off}$ ($10^{-2}$ s$^{-1}$) | $K_D$ ($10^{-6}$M) |
| HveC (346)[b] | 2.2 | 0.7 | 3.2 | 190 | 0.73 | 0.038 | 27 | 0.47 | 0.17 |
| HveC (143)[b] | 9.0 | 1.1 | 1.2 | 370 | 1.3 | 0.035 | 39 | 0.8 | 0.2 |

[a]KD = $k_{off}$/kon
[b]Data represent an average of at least two experiments also tested. In the case of gD-1rid1 mutant and gD-2, all truncations competed binding to HveC(346t) with similar efficiency. Thus, it was concluded that :3oluble gD binds HveC(143t) as well as it does to the other two truncated forms of HveC. Therefore the poor binding seen by direct ELISA (FIG. 24B) is due to changes in HveC(143t) that occur as a result of immobilization on the ELISA plate. Furthermore the data in FIG. 25 suggest that the affinity of all three HveC truncations for gD is similar.

Figure 25B:
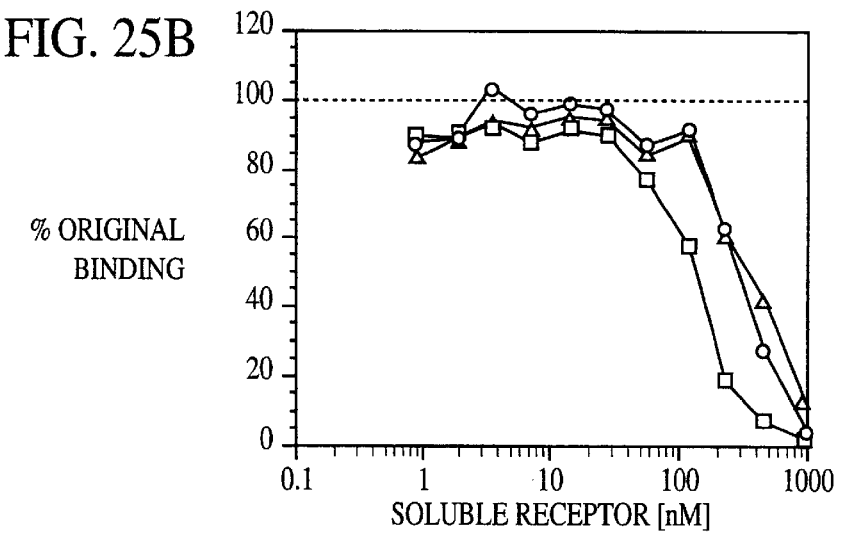
Figure 25C:
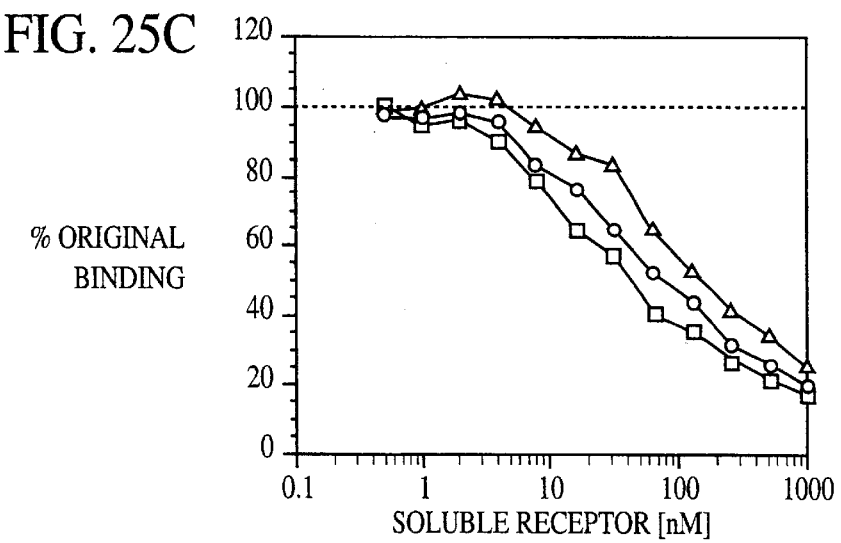
Figure 26A:
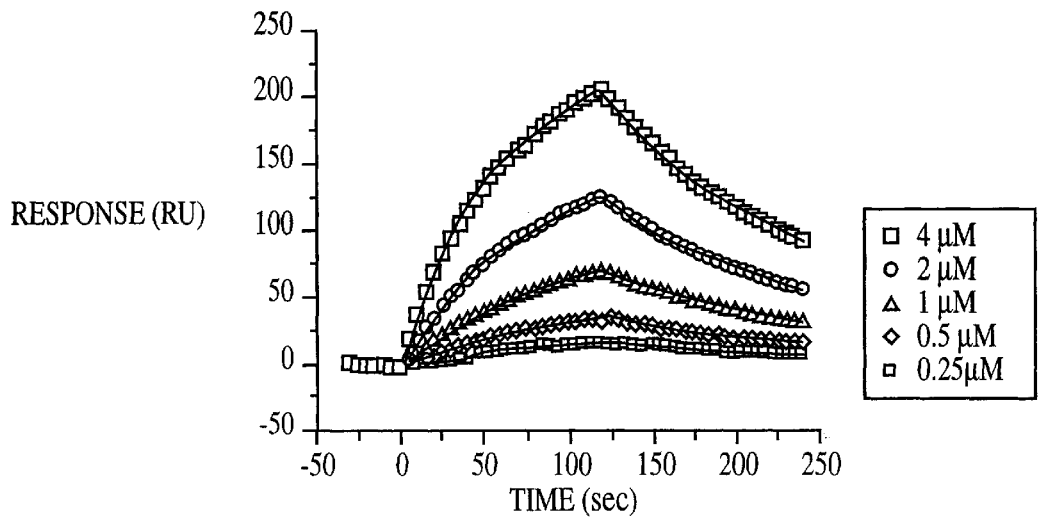
FIGS. 26A–26F, is a series of graphs depicting an analysis of gD binding to HveC in real time. HveC(346t) (FIG. 26A, 26C and 26E) or HveC(143t) (FIG. 26B, 26D and 26F) were immobilized on a CM5 biosensor chip to 1600 RU and 300 RU respectively in a Biacore X instrument. Various concentrations of gD(306t) (FIG. 26A and 26B), gD(285t) (FIG. 26C, and 26D), gD(rid1 t) (FIG. 26E, and 26F) were flowed over the chip for 2 minutes (association) and then replaced by buffer for another 2 minutes (dissociation). Sensorgrams of corrected data are represented after subtracting signal from the control flow cell. Data points were collected at 5 Hz but for clarity, only one every 25 points are represented here by a symbol. The solid line corresponds to the best fit obtained after global fitting with the BIAevaluation 3.0 software.
Figure 26B:
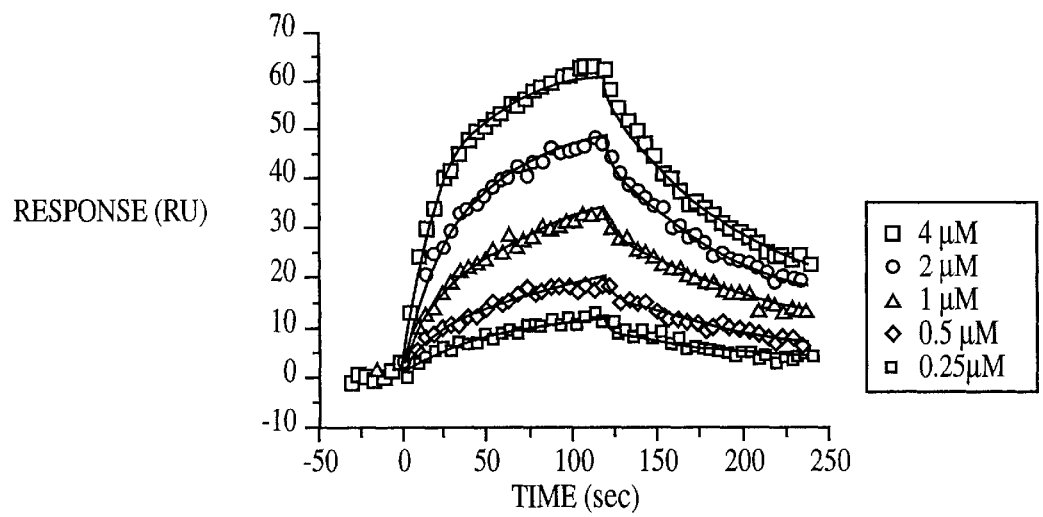
Figure 26C:
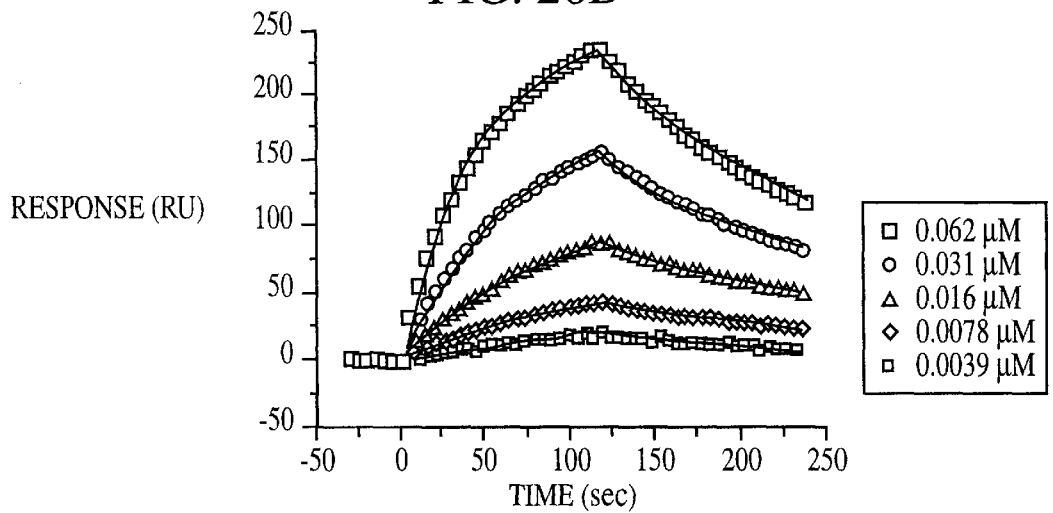
Figure 26D:
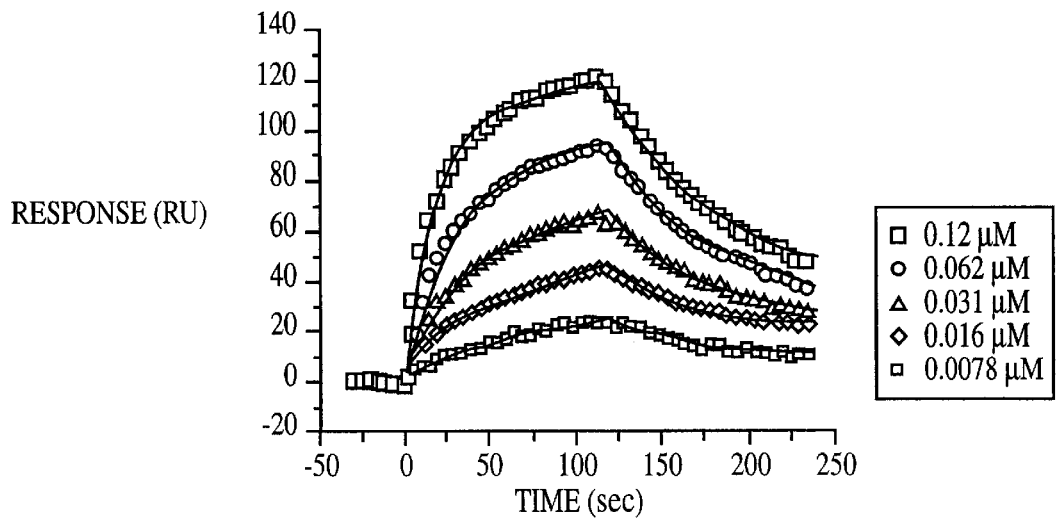
Figure 26E:
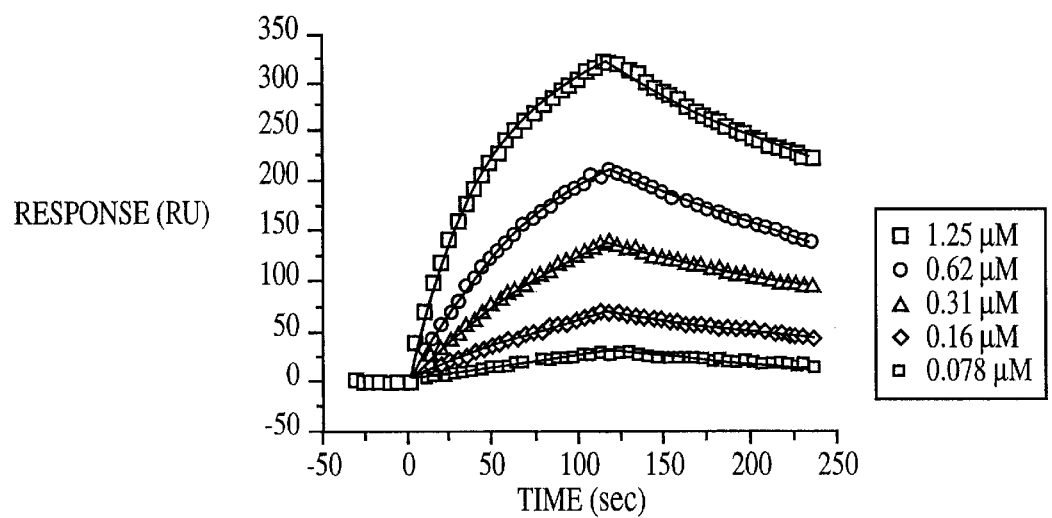
Figure 26F:
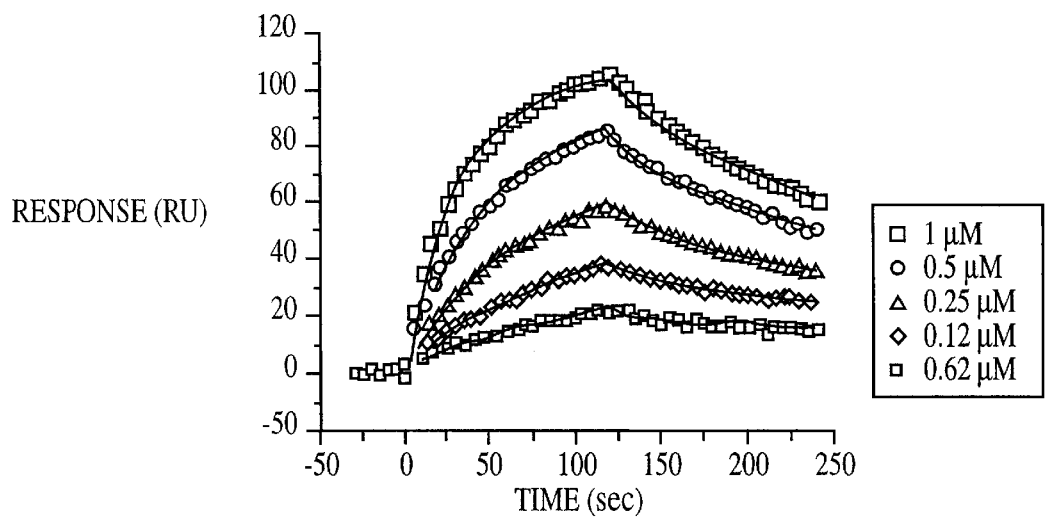

Affinity of binding between gD and HveC(346t) or HveC (143t). Biosensor analysis was previously used to measure affinity between gD mutant proteins and truncated receptor HveA (Rux et al., 1998, Journal of Virology 72:709–7098; Willis et al., 1998, J. Virol. 72:5937–5947). In the present experiment, the same approach was used to determine the affinity of gD complex formation with HveC(346t) and with the shorter form HveC(143t). HveC was coupled on the surface of one flow cell (Fc1) of a CM5 chip via primary amines and the second flow cell (Fc2) was left bare. The Fc2 response representing background sticking and bulk change of refractive index was subtracted from the Fc1 response too obtain specific binding data (FIG. 26). Serial dilutions of gD(306t) (FIGS. 26A–B), gD(285t) (FIGS. 26C–D) and gD(rid1t) (FIGS. 26E–F) were flowed over chips carrying HveC(346t) (FIGS. 26A, C, E) or HveC(143t) (FIGS. 25B, D, F). After establishing a baseline, the association of gD to immobilized HveC was monitored for 120 seconds. Then buffer was substituted for gD solution and the dissociation of the complex was followed for another two minutes. A global fit of the data was obtained using the B1Aevaluation 3.0 software for a 1:1 Langmuir model (FIG. 26). Kinetics values and affinity constants for each of the pairs tested are summarized in Table 2. In the case of HveC(346t), a dissociation constant (KD) of $3.2 \times 10^{-6}$ M for gD(306t) was calculated. The affinity of gD(285t) for HveC(346t) was enhanced more than 80 times, mainly because of an increase of the on rate ($k_{on}$). The association between HveC(346t) and gD(rid1t) exhibited a $K_D = 1.7 \times 10^{-7}$ M. The 20 fold increase in affinity compared to gD(306t) was also due to a higher on rate.

Figure 27A:
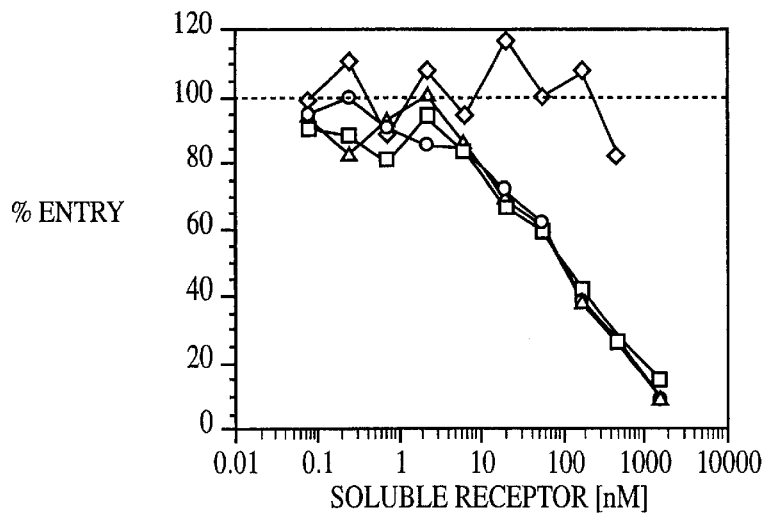
FIGS. 27A, 27B, and 27C, is a series of graphs depicting blocking of HSV infection with truncated soluble HveC. HSV-i KOS tk12 was preincubated with HveC(346t) (squares), HveC(143t) (circles), HveC(245t) (triangles), or BSA (diamonds) prior to addition to M3A (FIG. 27A), IMRS (FIG. 27B) or SY5Y cells (FIG. 27C). Cells were lysed at 5.5 hours post-infection and kinetic activity of β-galactosidase was measured. 100% of entry correspond to β-gal activity following infection with HSV-1KOS tk12 at a similar MOI (0.5–1 PFU/cell) in absence of soluble inhibitor.
Figure 27B:
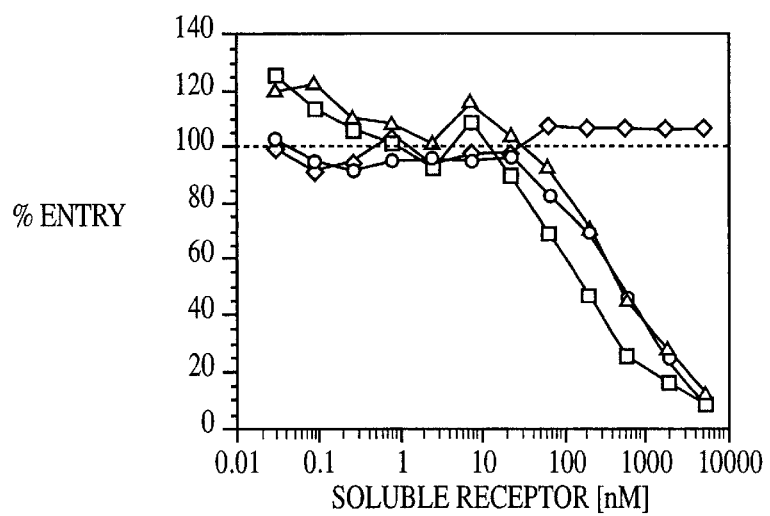
Figure 27C:
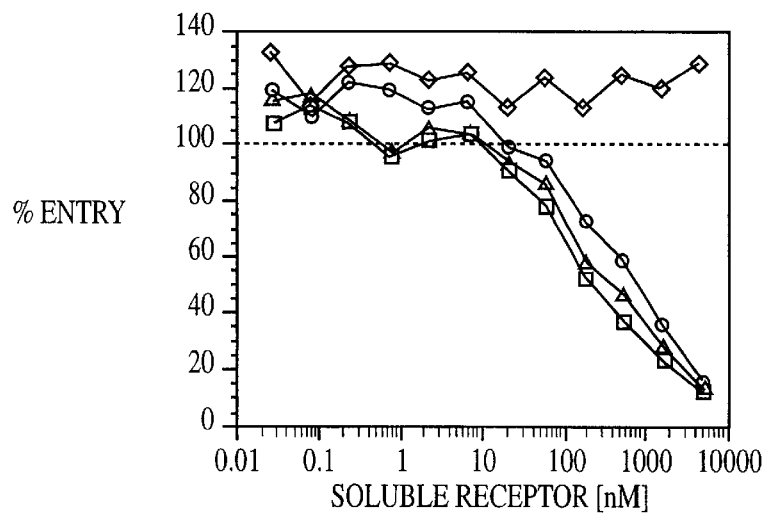

Blocking of HSV infection with soluble truncated forms of HveC. Since soluble forms of HveC were able to bind gD in solution, they were tested for their ability to block HSV-1 infection of several human cell lines. In the standard assay, purified HSV-1KOS tk12 was preincubated with the three soluble receptors prior to addition to target cells. M3A cells, derived from CHO cells, express full-length human HveC constitutively. Infection of M3A cells with HSV-1 KOS tk12 was efficiently blocked by all three HveC truncations (FIG. 27A). No significant difference was detected in the ability of any of the truncations to inhibit infection. This study was extended to neuroblastoma cell lines IMR5 and SY5Y, which have previously been shown to be sensitive to HSV-1 infection. Moreover, infection of these cells was inhibited by soluble HveC(346t). The data presented in FIGS. 27B and 27C demonstrate that HveC(245t) and HveC(143t) were able to block HSV-1 infection of these cells as efficiently as HveC(346t). Infection of non-differentiated NT-2 cells and HeLa cells could also be blocked by all three soluble forms of HveC with similar efficiency.

Figure 28:
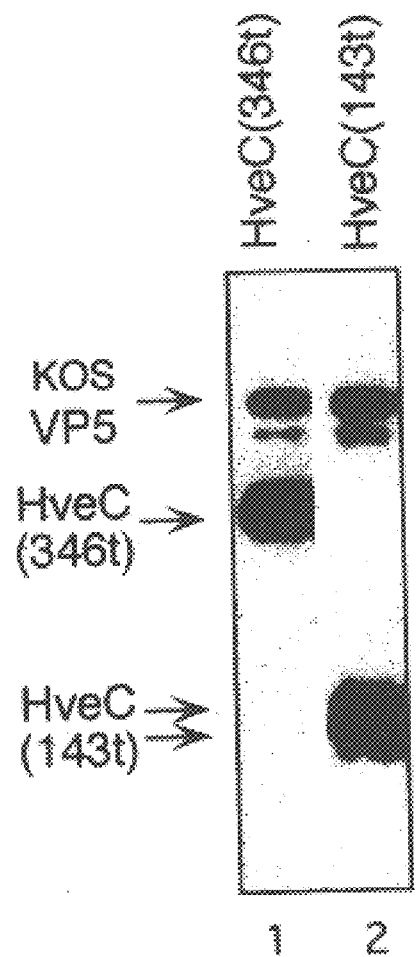
FIG. 28 is an image of a gel depicting binding of soluble HveC to HSV particles. Purified HveC(346t) or HveG(143t) (100 µg) were incubated with $10^7$ u of purified HSV-1 KOS, for 90 min at 4° C. Viral particles were then sedimented through a discontinuous sucrose gradient. The virus-containing fraction was collected, concentrated and analyzed by western blot for detection of HveC and virus. Receptors were detected with anti tetra-His antibody and VP5 capsid protein was detected with NC-1 polyclonal rabbit serum simultaneously.

Binding of soluble HveC to virion. The ability to block infection suggested that soluble forms of HveC directly interacted with viral particles. Binding of HveC(346t) with gD on HSV-1 KOS virions was shown previously herein. Here, the data demonstrate that the single Ig domain HveC (143t) bound directly to viral particles. Purified virions were preincubated with the soluble receptors prior to sedimentation through a sucrose gradient. The presence of receptor in the virus band collected from the gradient is indicative of direct binding of receptor to virion. On the western blot analysis of the viral band, both HveC(346t) and HveC(143t) could be detected and thus were bound to KOS viral particles (FIG. 28). The different glycosylated forms of HveC(143t) could be detected. Similar amounts of each virus were recovered and loaded on the gel as reflected by the amount of VP5 protein detected with NC 1 antibody (FIG. 28). Both HveC(346t) and HveC(143t) were also able to bind to purified HSV rid1 particles in this assay.

Figure 29A:
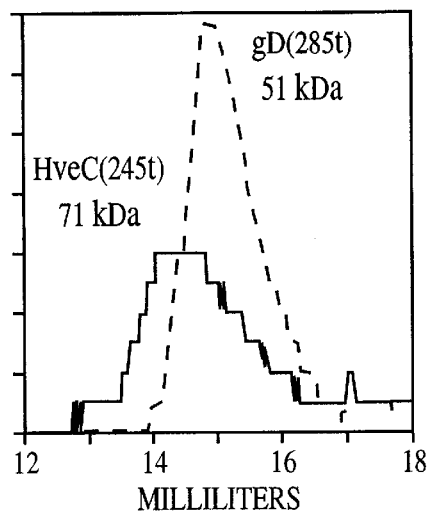
FIGS. 29A–29F, is a series of graphs depicting gel filtration chromatography of HveC(143t) and HveC(24St) alone or in a complex with gD(285t). The elution profiles of HveC(245t) and HveC(243t) loaded at 33 and 66 µM respectively, on a Superdex200 column are shown in FIGS. 29A and 29B as solid lines. The elution profiles of gD(285t) (26 mM) is shown as a dotted line in FIGS. 29A and 29B. The elution profiles of gD(285t):HveC (245t) complex (FIGS. 29C and 29E) or gD(285t):HveC (143t) (FIGS. 29D and 29F) at the given ratios are shown. Molecular weights are determined by calibrating the column with standards of proteins of known molecular weight ranging from 13.7 to 669 kDa. The shaded area in FIG. 29F indicates the fraction used for quantification of HveC(143t) and gD(285t) in FIG. 30.
Figure 29B:
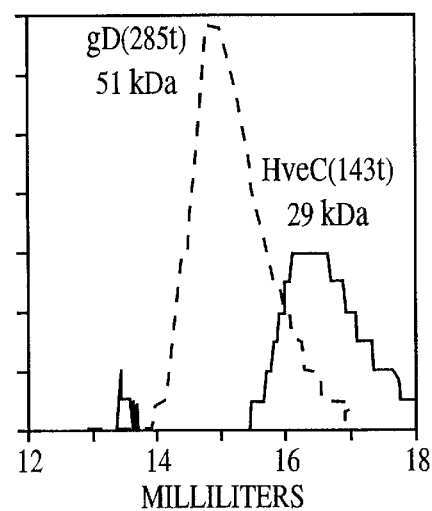

Oligomerization of HveC(143t) or HveC(245t). It has been demonstrated previously that HveC(346t) in solution appears as a high molecular weight complex of 176 kDa, a size consistent with that of a tetramer herein. Here, gel filtration studies were performed with all three HveC truncations on a Superdex 200 S size exclusion column. HveC (245t) having a molecular weight determined by mass spectrometry of 28 kDa, eluted with an apparent size of a 71 kDa (FIG. 29A) consistent with the formation of a dimer in solution. Similarly, the 15 kDa HveC(143t) formed a 29 kDa dimer in solution (FIG. 29B). The difference in oligomerization between HveC(346t), a tetramer, and HveC(245t), a dimer, suggests that the 3rd Ig-domain of HveC can promote a higher level of oligomerization of HveC. gD)(285t) eluted from the column with an apparent size of 51 kDa consistent with the presence of a dimeric form of gD (FIGS. 29A–B). Previously, it was observed that gD was essentially a dimer in solution and on virus (Handler et al., 1996, J. Virol. 70:6067–6075; Willis et al., 1998, J. Virol. 72:5937–5947).

Figure 29C:
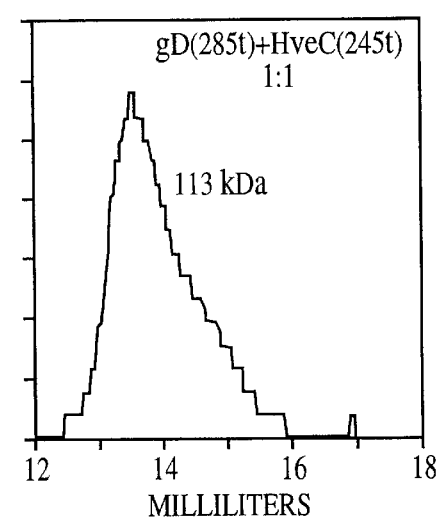
Figure 29D:
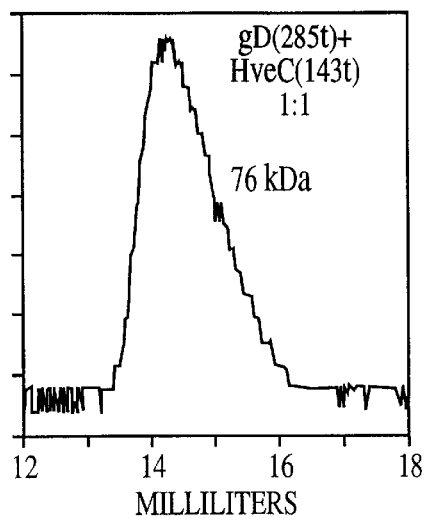
Figure 29E:
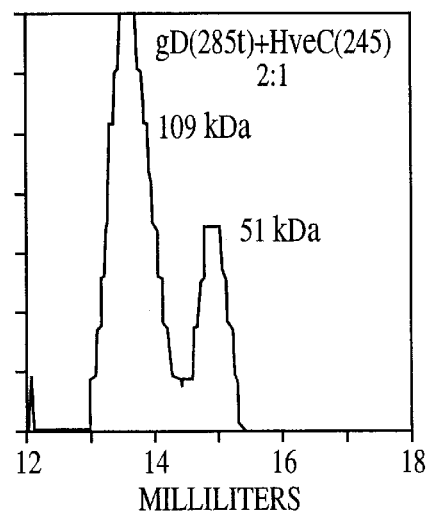
Figure 29F:
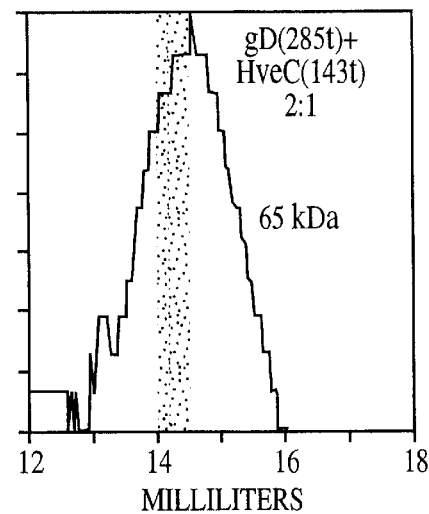

Complex formation in solution. Direct binding in solution of HveC(346t) to a mutant form of gD from HSV-1 KOS has been demonstrated. It was found that gD(A290–299t) bound to HveC(346t) with a stoichiometry of 2:1 and disrupted the putative HveC(346t) tetramer herein. Here, the sizes of complexes formed between gD(285t) and HveC(245t) by gel filtration were analyzed (FIGS. 29C and 29E). When equimolar amounts of HveC(245t) and gD(285t) were mixed, a complex of 113 kDa eluted from the column, a size consistent with a complex containing one dimer of gD and one dimer of HveC(245t) (51 kDa+71 kDa), hence with a stoichiometry of 1:1. When twice the amount of gD(285t) was added to HveC(245t), a peak of free gD(285t) dimer could be detected on the profile (FIG. 29E) and by western blot. When initially present at equimolar concentrations, HveC(143t) and gD(285t) formed a complex with an apparent size of 76 kDa (FIG. 29D), a size consistent with a complex containing one dimer of each component (29 kDa+51 kDa), also with a stoichiometry of 1:1. No free receptor was detected. When twice the amount of gD(285t) was initially present, the peak shifted to 65 kDa (FIG. 29F). This was due to an excess of free gD in fractions containing minimal amount of HveC(143t) as detected by western blot analysis of the fractions. Since the 1:1 ratio did not correlate with the stoichiometry obtained earlier with gD(346t) and gD(A290–299t), the study was repeated with HveC(346t) and gD(285t). In the presence of excess gD(285t) the complex eluted with a size of 76 kDa consistent with the previously observed complex made of two dimers of gD and one dimer of HveC(346t), a stoichiometry of 2:1.

Figure 30:
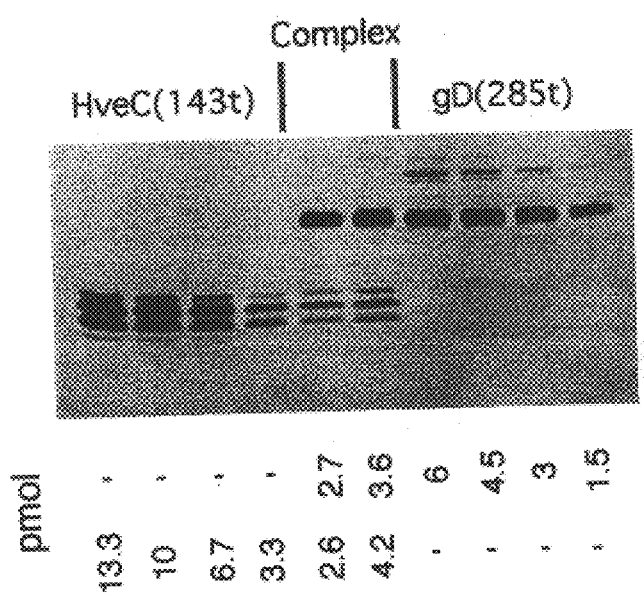
FIG. 30 is an image of a gel depicting quantification of gD(285t) and HveC(143t) in a complex. Two aliquots of a fraction containing the gD(285t):HveC(143t) complex separated by gel filtration (FIG. 29F) were loaded on a 16% polyacrylamide gel (lanes 5 and 6). Standards of known amounts of HveC(143t) and gD(285t) were loaded in lanes 1–4 and lanes 7–10, respectively, wherein amounts of proteins are indicated under the gel. After silver staining of the gel, the intensity of the protein bands was measured. The amount of each protein in the complex is indicated, based on the comparison with the standards.
Figure 31A:
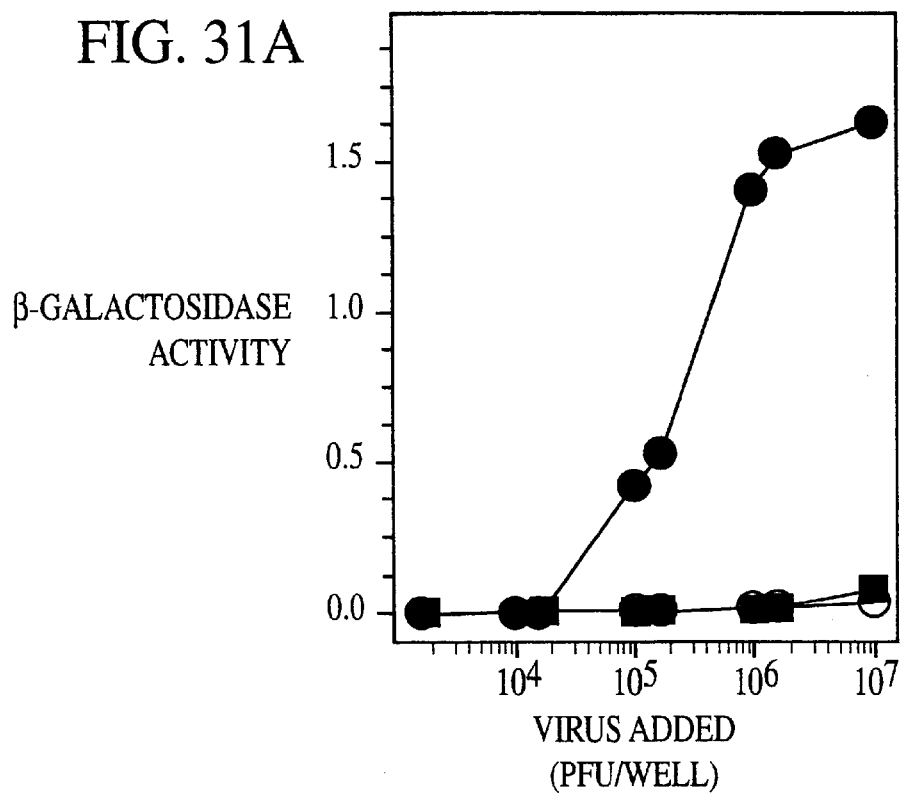
FIG. 31, comprising FIGS. 31A, 31B, 31C, arid 31D, is a series of graphs depicting infection, or the absence thereof, of HveB or HveC expressing cell lines with HSV-1(KOS) (FIGS. 31A and 31B) or HSV-1(Rid1) (FIGS. 31C and 31D). The receptor-expressing cell lines were derived from murine melanoma cells, B78H1 (FIGS. 31A and 31C), or from CHO cells (FIGS. 31B and 31D). In these figures, filled circles corresopnd to data relating to HveC, filled squares correspond to data relating to HveB, and open circles correspond to data relating to the control.
Figure 31B:
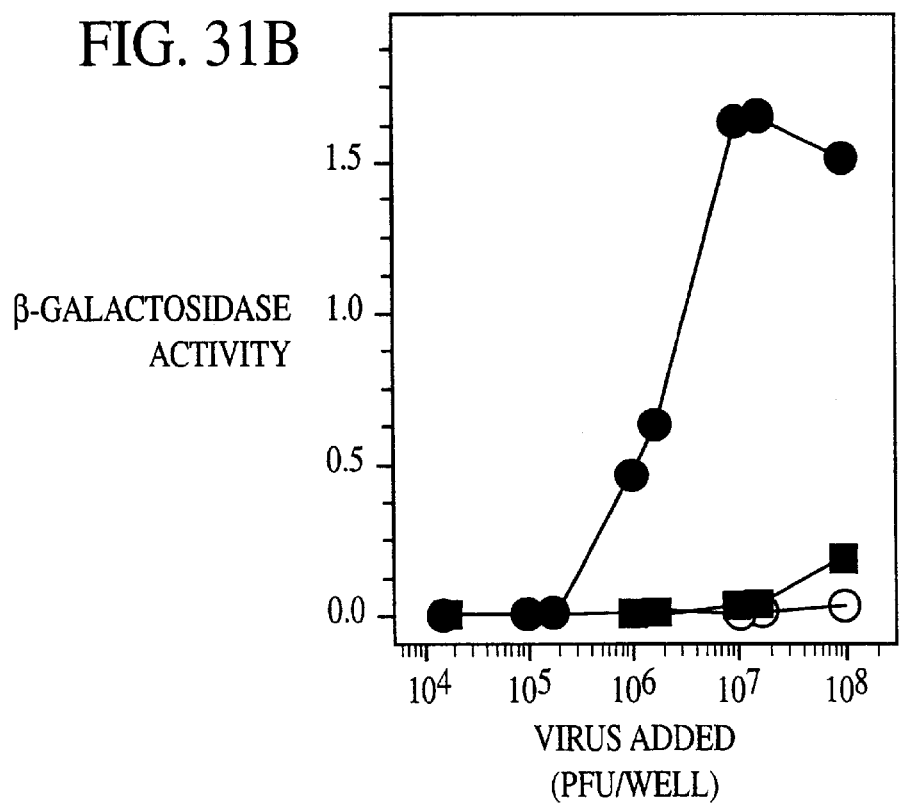
Figure 31C:
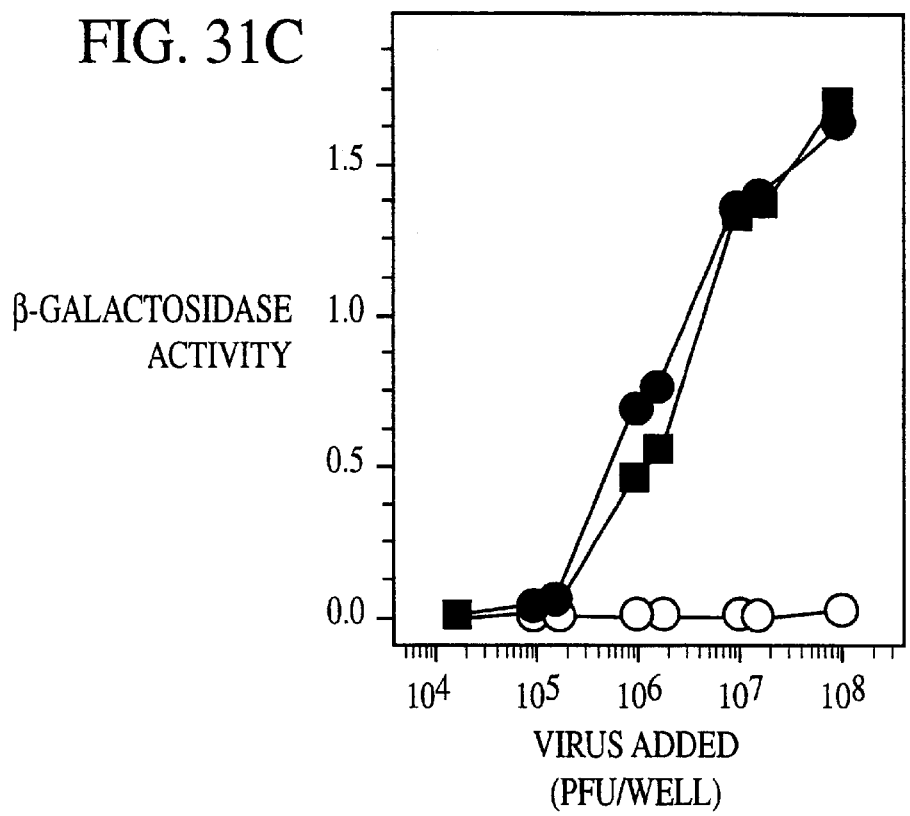
Figure 31D:
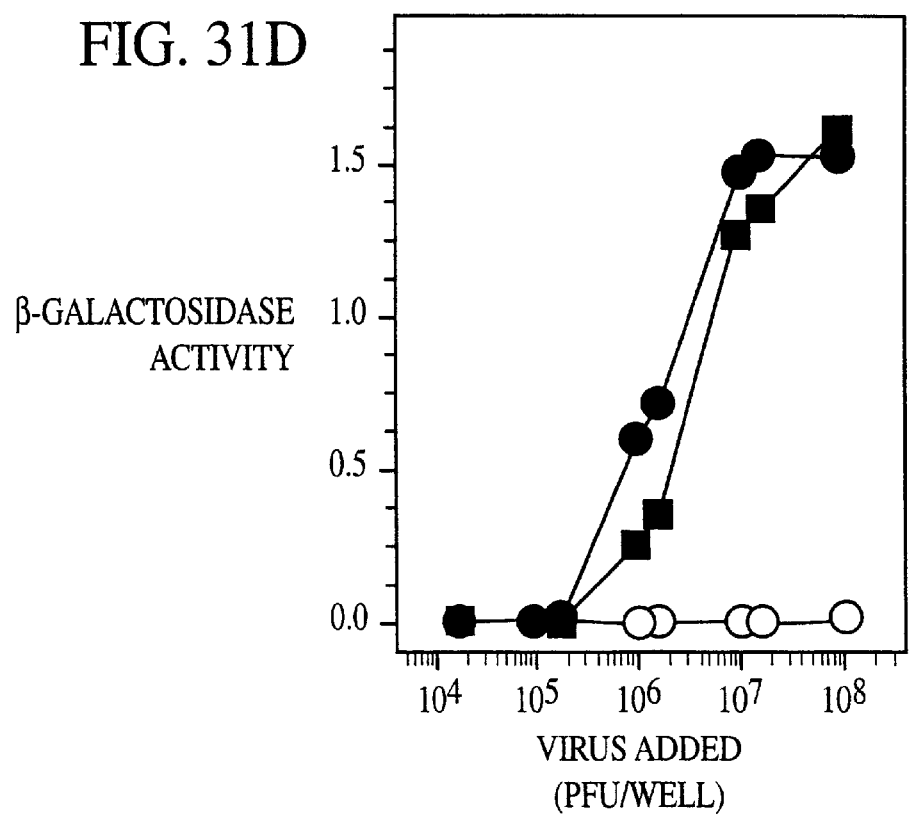
Figure 32A:
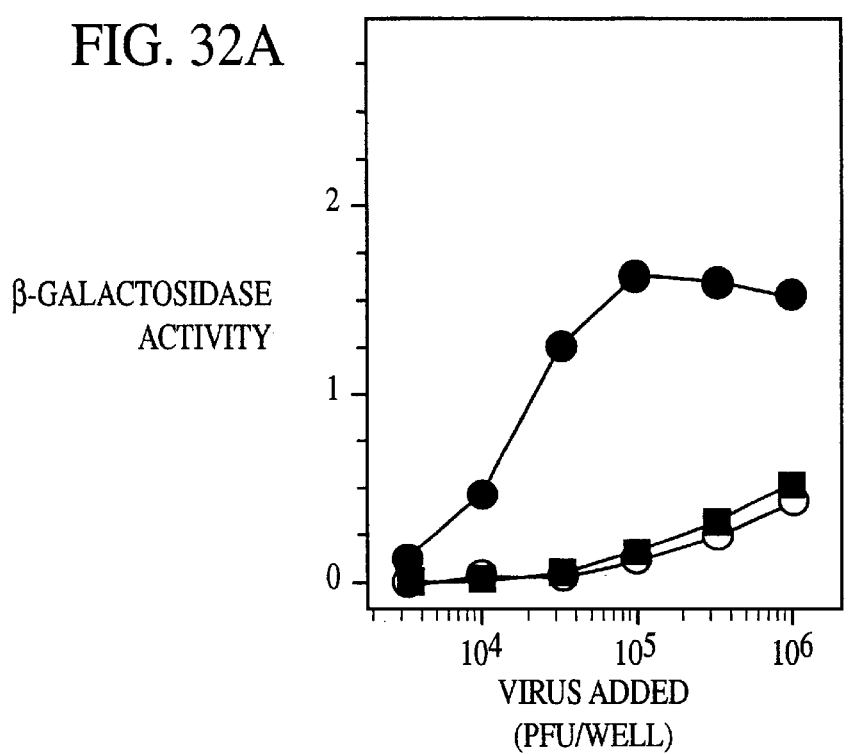
FIGS. 32A, 32B, 32C, and 32D, is also a series of graphs depicting infection, or the absence thereof, of HveB or HveC expressing cell lines with HSV-2(333) (FIGS. 32A and 32B) or HSV-1(SC16) (FIGS. 32C and 32D). The receptor-expressing cell lines were derived from murine melanoma cells, B78H1 (FIGS. 32A and 32C), or from CHO cells (FIGS. 32B and 32D). In these figures, filled circles correspond to data relating to HveC, filled squares correspond to data relating to HveB, and open circles correspond to data relating to the control.
Figure 32B:
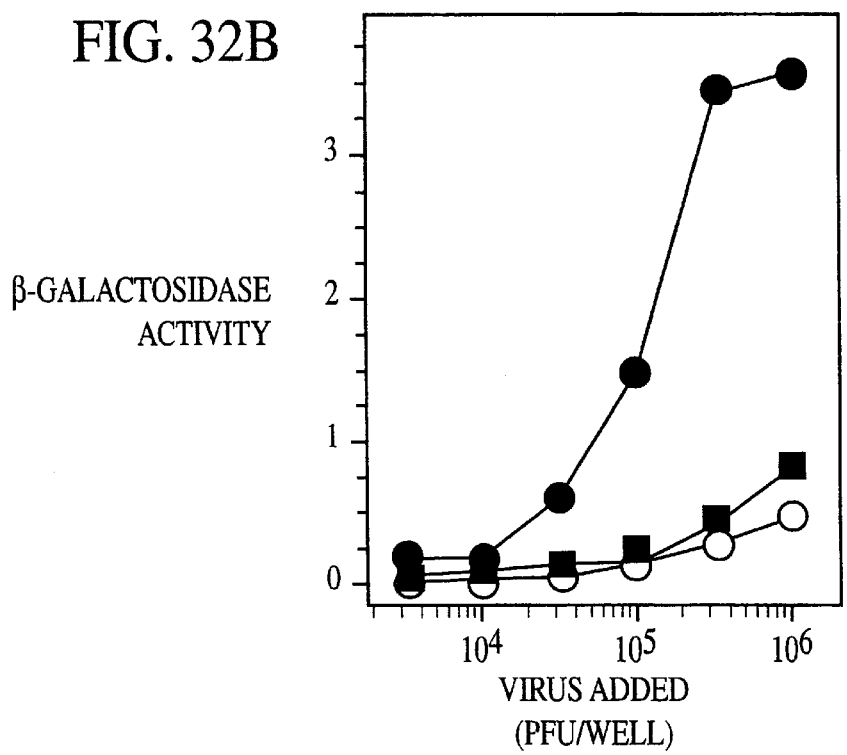
Figure 32C:
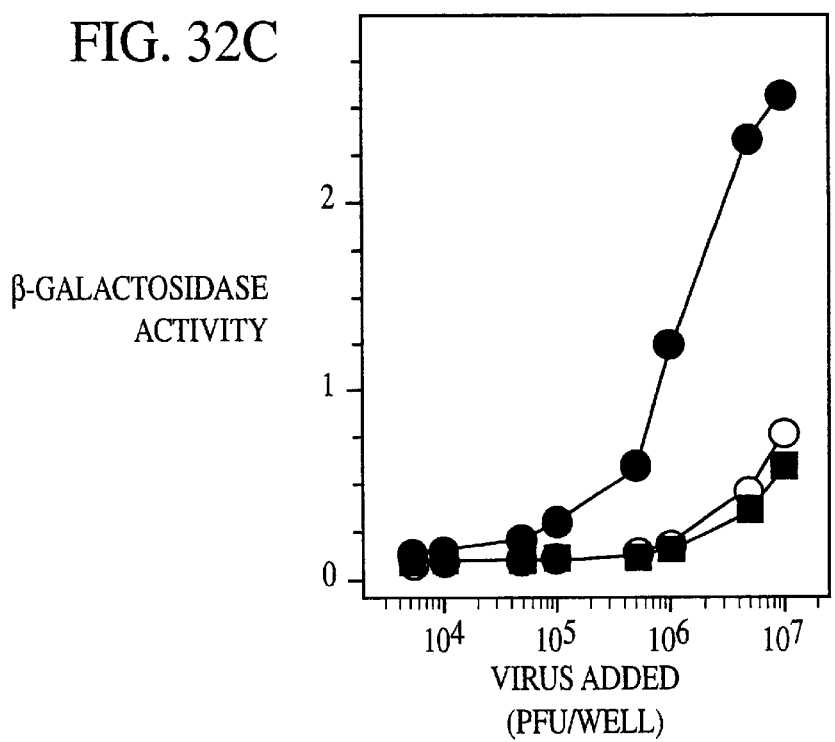
Figure 32D:
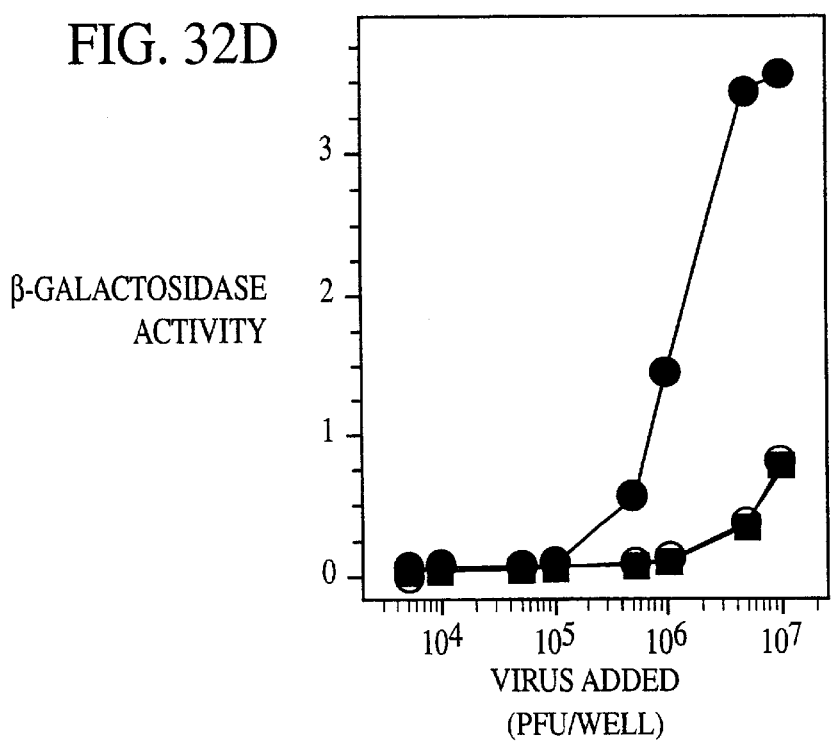
Figure 33A:
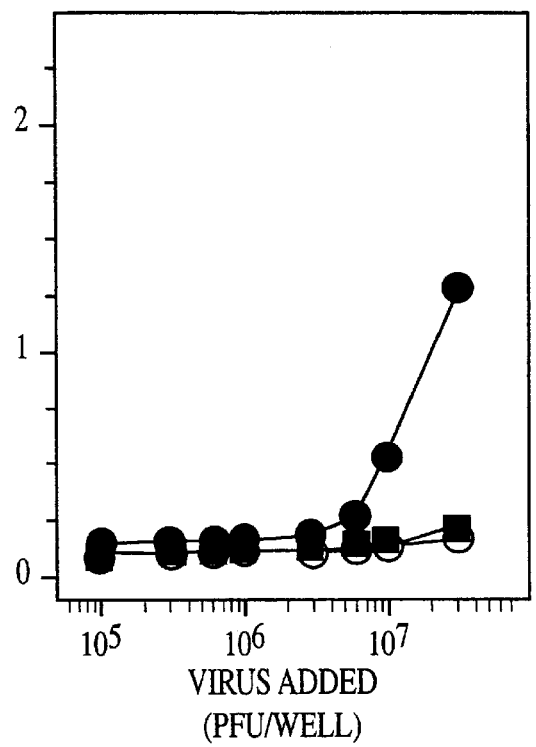
FIGS. 33A, 33B, 33C, and 33D, is a series of graphs depicting infection, or the absence thereof, of HveB or HveC expressing cell lines with pseudorabies virus (FIGS. 33C and 33D) or bovine herpesvirus type 1 (FIGS. 33A and 33B) The receptor-expressing cell lines were derived from murine melanoma cells, B78H1 (FIGS. 33A and 33C), or from CHO cells (FIGS. 33B and 33D). In these figures, filled circles correspond to data relating to HveC, filled squares correspond to data relating to HveB, and open circles corresopnd to data relating to the control.
Figure 33B:
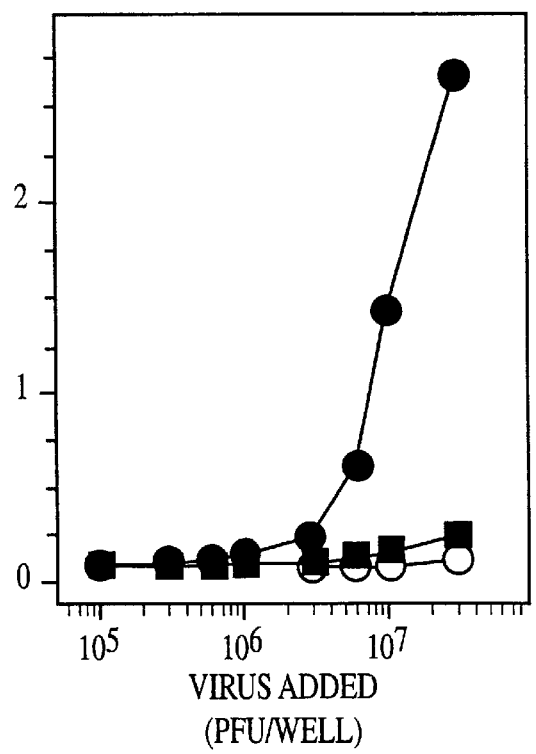
Figure 33C:
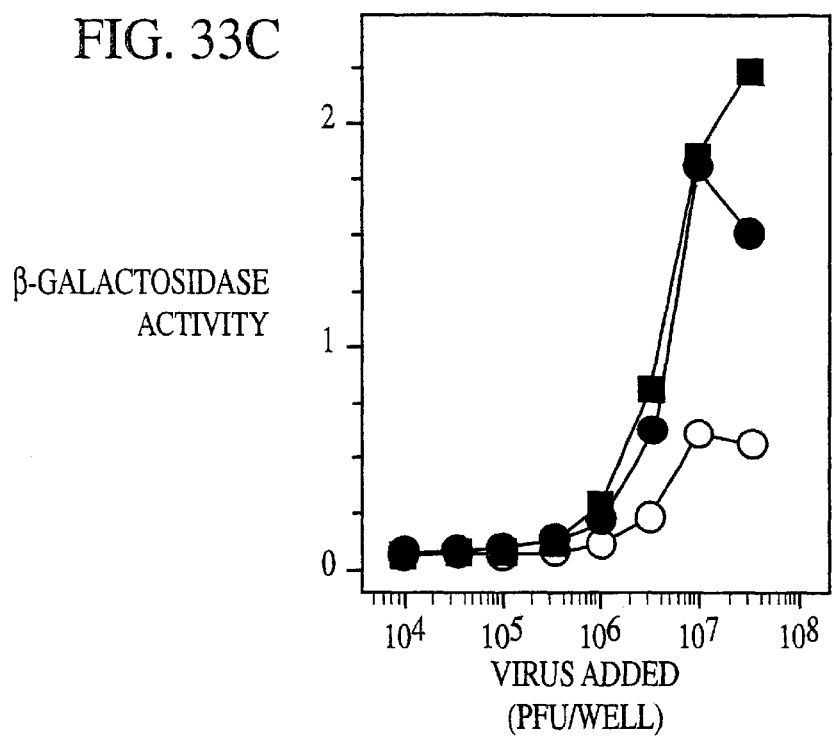
Figure 33D:
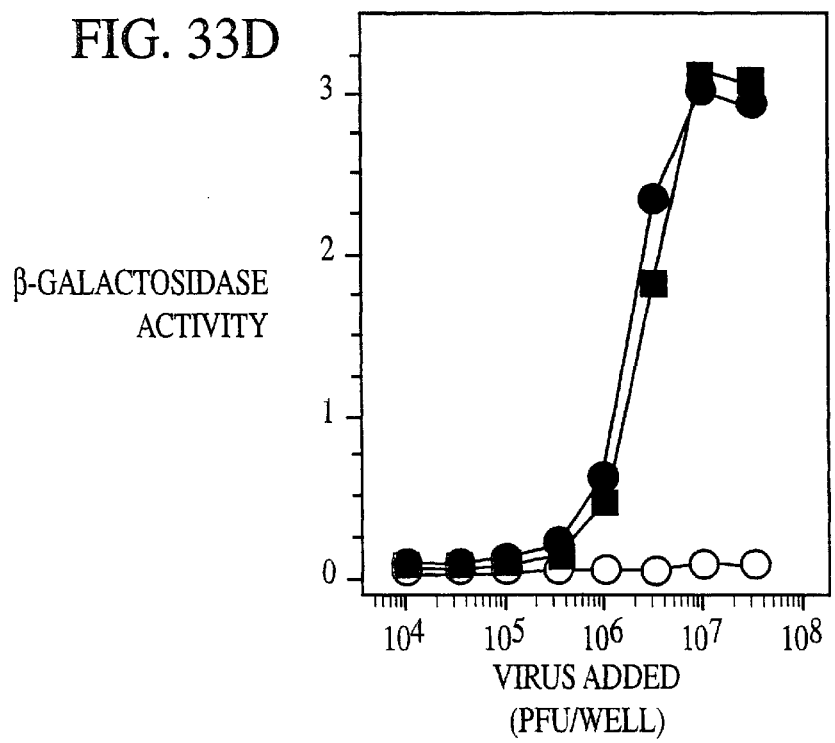

To confirm the stoichiometry of the gD(285t):HveC(143t) complex, each component of the complex was separated and quantified by PAGE (FIG. 30). A fraction of the complex generated in excess of gD(285t), but selected outside the free gD peak was analyzed at 2 different dilutions (FIG. 30, lanes 5 and 6). By comparing the intensity of the silver stained proteins in the fraction with known standards (lanes 1–4, 7–10), it was determined that similar amounts of gD(285t) and HveC(143t) were present in the complex. This indicated a 1:1 ratio of HveC(143t) to gD(285t), supporting the ratio deducted from the size of the complex. This experiment could not be performed with the gD(285t):HveC(245t) complex because both protein monomers are too close in size to be sufficiently separated on a gel to allow accurate quantification. When the amount of gD(285t) and HveC(346t) in the complex, formed in presence of excess gD(285t), were quantified using silver stained gel analysis, the 2:1 ratio was obtained confirming the previous observations herein.

EXAMPLE 5

Cell Lines Which Express HveB and HveC

Most cultured cell types are susceptible to infection by herpes simplex virus (HSV) and express multiple receptors for HSV entry. In the experiments presented herein, several of those receptors have been identified. These data establish that each receptor can function independently as a viral entry receptor and that each has different specificities for various strains of HSV and certain animal herpesviruses.

In order to define the requirements for HSV entry via each of the specific receptors and to search for agents capable of blocking entry via each receptor, a series of cell lines have been generated which express individual HSV entry receptors.

These lines were generated by transfecting cell lines that are normally devoid of HSV receptors with plasmids expressing either HveB or HveC.

Three cell lines which are resistant to entry of some or all strains of herpes simplex virus (HSV) have been used in these studies aimed at identifying human cell surface receptors for HSV entry. These cell lines are Chinese hamster ovary (CHO) cells, mouse melanoma cells, designated B78H1, and swine testes cells. Tranfection into these cells of plasmids expressing a single human receptor for HSV renders them susceptible to HSV entry via that receptor. Stable CHO and B78H1 cell lines have been generated that constitutively express HveB and HveC. The plasmids used to generate these cell lines were pMW20 and pBG38, which comprise the cDNAs for HveB and HveC, respectively, in pcDNA3. The drug G418 was used to select for cells that stably maintained the plasmids, all of which cells contained the neomycin selectable marker gene. Flow cytometry was conducted, using antibodies specific for HveB and HveC, to identify clones of G418-resistant cells that expressed HveB or HveC. Control cell lines were transfected with pcDNA3 and were similarly selected in G418.

The results of the experiments conducted on the cell lines were designed to demonstrate the changes in susceptibility of B78H1 cells and CHO cells to various herpesviruses as a result of expression of HveB or HveC therein. All of the viruses used were recombinants that expressed β-galactosidase encoded by the viral genome immediately upon entry into a susceptible cell. These recombinant viruses have been described elsewhere herein. Expression of enzyme activity is therefore a measure of the number of cells infected at the various input doses of viruses used.

In FIGS. 31 and 32, it can be seen that strains HSV-1 (KOS), HSV-1(5C16) and HSV-2(333), all of which express wild-type gD, can infect B78H1 cells and CHO cells expressing HveC, but do not infect those cells which express HveB and do not infect control cells. Note that HveB expression renders CHO cells somewhat susceptible to HSV-2(333) entry although HveC is clearly a much more effective entry receptor for this virus. In contrast, the virus strain which expressed an altered form of gD, HSV-1(KOS) Rid1, can infect B78H1 cells and CHO cells expressing either HveB or HveC, but not control cells. Thus, these cells are useful cells for the identification of clinical isolates of HSV that have altered receptor specificity, due to mutations in gD, and therefore altered pathogenicity. These cells can also be useful for screening for agents that block entry via one or both receptors.

In FIG. 33, there is shown the fact that cells which express HveC were susceptible to both the porcine pseudorabies virus (PRV) and bovine herpesvirus type 1 (BHV), whereas cells which express HveB were susceptible to PRV but not to BHV. PRV can infect control B78H1 cells more readily that the other viruses tested because these cells express an endogenous receptor for PRV. Therefore, enhancement of PRV entry due to HveB or HveC expression in B78H1 cells is minimal.

The disclosures of each and every patent, patent application, and publication cited herein are hereby incorporated herein by reference in their entirely.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cellular herpesvirus entry protein consisting of the polypeptide set forth in SEQ ID NO:4 suspended in a pharmaceutically active carrier.

2. The cellular herpesvirus entry protein of claim 1, wherein said alphaherpesvirus is selected from the group consisting of HSV-1, HSV-2, PRV and BHV-1.

3. An isolated nucleic acid consisting of SEQ ID NO:4.

* * * * *

SEQUENCE LISTING

<160> NUMBER OF SEQ ID NOS: 26

<210> SEQ ID NO 1
<211> LENGTH: 1928
<212> TYPE: DNA
<213> ORGANISM: Homo sapiens

<400> SEQUENCE: 1

```
gagcagaaca gggaggctag agcgcagcgg gaaccggccc ggagccggag ccggagcccc      60
acaggcacct actaaaccgc ccagccgatc ggcccccaca gagtggcccg cgggcctccg     120
gccgggccca gtcccctccc gggccctcca tggcccgggc cgctgccctc ctgccgtcga     180
gatcgccgcc gacgccgctg ctgtggccgc tgctgctgct gctgctcctg gaaaccggag     240
cccaggatgt gcgagttcaa gtgctacccg aggtgcgagg ccagctcggg ggcaccgtgg     300
agctgccgtg ccacctgctg ccacctgttc ctggactgta catctccctg gtgacctggc     360
agcgcccaga tgcacctgcg aaccaccaga atgtggccgc cttccaccct aagatgggtc     420
ccagcttccc cagcccgaag cctggcagcg agcggctgtc cttcgtctct gccaagcaga     480
gcactgggca agacacagag gcagagctcc aggacgccac gctggccctc cacgggctca     540
cggtggagga cgagggcaac tacacttgcg agtttgccac cttccccaag gggtccgtcc     600
gagggatgac ctggctcaga gtcatagcca agcccaagaa ccaagctgag gcccagaagg     660
tcacgttcag ccaggaccct acgacagtgg ccctctgcat ctccaaagag ggccgcccac     720
ctgcccggat ctcctggctc tcatccctgg actgggaagc caaagagact caggtgtcag     780
ggaccctggc cggaactgtc actgtcacca gccgcttcac cttggtgccc tcgggccgag     840
cagatggtgt cacggtcacc tgcaaagtgg agcatgagag cttcgaggaa ccagccctga     900
tacctgtgac cctctctgta cgctaccctc ctgaagtgtc catctccggc tatgatgaca     960
actggtacct cggccgtact gatgccaccc tgagctgtga cgtccgcagc aacccagagc    1020
ccacgggcta tgactggagc acgacctcag gcaccttccc gacctccgca gtggcccagg    1080
gctcccagct ggtcatccac gcagtggaca gtctgttcaa taccaccttc gtctgcacag    1140
tcaccaatgc cgtgggcatg ggccgcgctg agcaggtcat ctttgtccga gaaaccccca    1200
gggcctcgcc ccgagatgtg ggcccgctgg tgtggggggc cgtggggggg acactgctgg    1260
tgctgctgct tctggctggg gggtccttgg ccttcatcct gctgagggtg aggaggagga    1320
ggaagagccc tggaggagca ggaggaggag ccagtggcga cggggattc tacgatccga    1380
aagctcaggt gttgggaaat ggggacccg tcttctggac accagtagtc cctggtccca    1440
tggaaccaga tggcaaggat gaggaggagg aggaggagga agaagggca gagaaaggcc    1500
tcatgttgcc tccacccca gcactcgagg atgacatgga gtcccagctg gacggctccc    1560
tcatctcacg gcgggcagtt tatgtgtgac ctggacacag acagagacag agccaggccc    1620
ggccctcccg ccccgacct gaccacgccg gcctagggtt ccagactggt tggacttgtt    1680
cgtctggacg acactggagt ggaacactgc ctcccacttt cttgggactt ggagggaggt    1740
ggaacagcac actggacttc tcccgtctct agggctgcat ggggagcccg gggagctgag    1800
```

-continued

```
tagtggggat ccagagagga cccccgcccc cagagacttg gttttggctc cagccttccc      1860
ctggccccgt gacactcagg agttaataaa tgccttggag gaaaacaaaa aaaaaaaaaa      1920
aaaaaaaa                                                                1928
```

<210> SEQ ID NO 2
<211> LENGTH: 479
<212> TYPE: PRT
<213> ORGANISM: Homo sapiens

<400> SEQUENCE: 2

```
Met Ala Arg Ala Ala Ala Leu Leu Pro Ser Arg Ser Pro Pro Thr Pro
  1               5                  10                  15

Leu Leu Trp Pro Leu Leu Leu Leu Leu Leu Glu Thr Gly Ala Gln
                 20                  25                  30

Asp Val Arg Val Gln Val Leu Pro Glu Val Arg Gly Gln Leu Gly Gly
             35                  40                  45

Thr Val Glu Leu Pro Cys His Leu Leu Pro Pro Val Pro Gly Leu Tyr
         50                  55                  60

Ile Ser Leu Val Thr Trp Gln Arg Pro Asp Ala Pro Ala Asn His Gln
 65                  70                  75                  80

Asn Val Ala Ala Phe His Pro Lys Met Gly Pro Ser Phe Pro Ser Pro
                 85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
        115                 120                 125

Gly Leu Thr Val Glu Asp Glu Gly Asn Tyr Thr Cys Glu Phe Ala Thr
    130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
    210                 215                 220

Leu Val Pro Ser Gly Arg Ala Asp Gly Val Thr Val Thr Cys Lys Val
225                 230                 235                 240

Glu His Glu Ser Phe Glu Glu Pro Ala Leu Ile Pro Val Thr Leu Ser
                245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
        275                 280                 285

Pro Glu Pro Thr Gly Tyr Asp Trp Ser Thr Ser Gly Thr Phe Pro
    290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Arg Ala
```

|  | | 340 | | | | 345 | | | | 350 | |
|---|---|---|---|---|---|---|---|---|---|---|---|
| Ser | Pro | Arg | Asp | Val | Gly | Pro | Leu | Val | Trp | Gly | Ala | Val | Gly | Gly | Thr |
| | | 355 | | | | 360 | | | | 365 | |

| Leu | Leu | Val | Leu | Leu | Leu | Ala | Gly | Gly | Ser | Leu | Ala | Phe | Ile | Leu |
|---|---|---|---|---|---|---|---|---|---|---|---|---|---|---|
| | 370 | | | | 375 | | | | 380 | |

| Leu | Arg | Val | Arg | Arg | Arg | Lys | Ser | Pro | Gly | Ala | Gly | Gly |
|---|---|---|---|---|---|---|---|---|---|---|---|---|
| 385 | | | | 390 | | | | 395 | | | | 400 |

| Ala | Ser | Gly | Asp | Gly | Phe | Tyr | Asp | Pro | Lys | Ala | Gln | Val | Leu | Gly |
|---|---|---|---|---|---|---|---|---|---|---|---|---|---|---|
| | | | 405 | | | | 410 | | | | 415 | |

| Asn | Gly | Asp | Pro | Val | Phe | Trp | Thr | Pro | Val | Val | Pro | Gly | Pro | Met | Glu |
|---|---|---|---|---|---|---|---|---|---|---|---|---|---|---|---|
| | | | 420 | | | | 425 | | | | 430 | |

| Pro | Asp | Gly | Lys | Asp | Glu | Glu | Glu | Glu | Glu | Glu | Lys | Ala | Glu |
|---|---|---|---|---|---|---|---|---|---|---|---|---|---|
| | | 435 | | | | 440 | | | | 445 | |

| Lys | Gly | Leu | Met | Leu | Pro | Pro | Pro | Ala | Leu | Glu | Asp | Asp | Met | Glu |
|---|---|---|---|---|---|---|---|---|---|---|---|---|---|---|
| | 450 | | | | 455 | | | | 460 | |

| Ser | Gln | Leu | Asp | Gly | Ser | Leu | Ile | Ser | Arg | Arg | Ala | Val | Tyr | Val |
|---|---|---|---|---|---|---|---|---|---|---|---|---|---|---|
| 465 | | | | | 470 | | | | 475 | |

<210> SEQ ID NO 3
<211> LENGTH: 1710
<212> TYPE: DNA
<213> ORGANISM: Homo sapiens

<400> SEQUENCE: 3

```
cacccagccc accccgcccc ggccgacggc tgcagctgac ctggatcctt cgagcgcccg      60
ccgaccgcca gcgatcttcc ctcatcttcc gggctggttt ctgctgcgcg aggagcgctg     120
ccctcgccgc ccctctcgcc ggaccccggg ccccgatggc tcggatgggg gcttgcgggc     180
gccgctggac gctggtgggg actcgctctc ggcttgaccg cattcttcct cccaggcgtc     240
cactcccagg tggtccaggt gaacgactcc atgtatggct catcggcac agacgtggtt      300
ctgcactgca gctttgccaa cccgcttccc agcgtgaaga tcacccaggt cacatggcag     360
aagtccacca atggctccaa gcagaacgtg gccatctaca cccatccat gggcgtgtcc      420
gtgctggctc cctaccgcga gcgtgtggaa ttcctgcggc cctccttcac cgatggcact     480
atccgcctct cccgcctgga gctggaggat gagggtgtct acatctgcga gtttgctacc     540
ttccctacgg gcaatcgaga aagccagctc aatctcacgg tgatggccaa acccaccaat     600
tggatagagg gtacccaggc agtgcttcga gccaagaagg ggcaggatga caaggtcctg     660
gtggccacct gcacctcagc caatgggaag cctcccagtg tggtatcctg ggaaactcgg     720
ttaaaaggtg aggcagagta ccaggagatc cggaacccca atggcacagt gacggtcatc     780
agccgctacc gcctggtgcc cagcagggaa gcccaccagc agtccttggc ctgcatcgtc     840
aactaccaca tggaccgctt caaggaaagc ctcactctca acgtgcagta tgagcctgag     900
gtaaccattg agggtttga tggcaactgg tacctgcagc ggatggacgt gaagctcacc     960
tgcaaagctg atgctaaccc cccagccact gagtaccact ggaccacgct aaatggctct    1020
ctccccaagg gtgtggaggc ccagaacaga accctcttct tcaagggacc catcaactac    1080
agcctggcag ggacctacat ctgtgaggcc accaacccca tcggtacacg ctcaggccag    1140
gtggaggtca atatcacaga attcccctac accccgtctc ctcccgaaca tgggcggcgc    1200
gccgggccgg tgcccacggc catcattggg ggcgtggcgg ggagcatcct gctggtgttg    1260
attgtggtcg gcgggatcgt ggtcgccctg cgtcggcgcc ggcacacctt caagggtgac    1320
tacagcacca agaagcacgt gtatggcaac ggctacagca aggcaggcat cccccagcac    1380
```

-continued

```
cacccaccaa tggcacagaa cctgcagtac cccgacgact cagacgacga gaagaaggcc    1440
ggcccactgg gtggaagcag ctatgaggag gaggaggagg aggaggaggg cggtggaggg    1500
ggcgagcgca aggtgggcgg ccccaccccc aaatatgacg aggacgccaa gcggccctac    1560
ttcaccgtgg atgaggccga ggcccgtcag gacggctacg ggaccggac  tctgggctac    1620 cagtacgacc ctgagcagct ggacttggct gagaacatgg tttctcagaa cgacgggtct    1680
ttcatttcca agaaggagtg gtacgtgtag                                     1710
```

<210> SEQ ID NO 4
<211> LENGTH: 517
<212> TYPE: PRT
<213> ORGANISM: Homo sapiens

<400> SEQUENCE: 4

```
Met Ala Arg Met Gly Leu Ala Gly Ala Ala Gly Arg Trp Trp Gly Leu
  1               5                  10                  15

Ala Leu Gly Leu Thr Ala Phe Phe Leu Pro Gly Val His Ser Gln Val
             20                  25                  30

Val Gln Val Asn Asp Ser Met Tyr Gly Phe Ile Gly Thr Asp Val Val
         35                  40                  45

Leu His Cys Ser Phe Ala Asn Pro Leu Pro Ser Val Lys Ile Thr Gln
     50                  55                  60

Val Thr Trp Gln Lys Ser Thr Asn Gly Ser Lys Gln Asn Val Ala Ile
 65                  70                  75                  80

Tyr Asn Pro Ser Met Gly Val Ser Val Leu Ala Pro Tyr Arg Glu Arg
                 85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

Ala Glu Tyr Gln Glu Ile Arg Asn Pro Asn Gly Thr Val Thr Val Ile
        195                 200                 205

Ser Arg Tyr Arg Leu Val Pro Ser Arg Glu Ala His Gln Gln Ser Leu
    210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
                245                 250                 255

Asn Trp Tyr Leu Gln Arg Met Asp Val Lys Leu Thr Cys Lys Ala Asp
            260                 265                 270

Ala Asn Pro Pro Ala Thr Glu Tyr His Trp Thr Thr Leu Asn Gly Ser
        275                 280                 285

Leu Pro Lys Gly Val Glu Ala Gln Asn Arg Thr Leu Phe Phe Lys Gly
    290                 295                 300

Pro Ile Asn Tyr Ser Leu Ala Gly Thr Tyr Ile Cys Glu Ala Thr Asn
```

```
305                 310                 315                 320
Pro Ile Gly Thr Arg Ser Gly Gln Val Glu Val Asn Ile Thr Glu Phe
                325                 330                 335
Pro Tyr Thr Pro Ser Pro Pro Glu His Gly Arg Arg Ala Gly Pro Val
                340                 345                 350
Pro Thr Ala Ile Ile Gly Gly Val Ala Gly Ser Ile Leu Leu Val Leu
                355                 360                 365
Ile Val Val Gly Gly Ile Val Val Ala Leu Arg Arg Arg Arg His Thr
                370                 375                 380
Phe Lys Gly Asp Tyr Ser Thr Lys Lys His Val Tyr Gly Asn Gly Tyr
385                 390                 395                 400
Ser Lys Ala Gly Ile Pro Gln His His Pro Pro Met Ala Gln Asn Leu
                405                 410                 415
Gln Tyr Pro Asp Asp Ser Asp Asp Glu Lys Lys Ala Gly Pro Leu Gly
                420                 425                 430
Gly Ser Ser Tyr Glu Glu Glu Glu Glu Glu Gly Gly Gly Gly
                435                 440                 445
Gly Glu Arg Lys Val Gly Pro His Pro Lys Tyr Asp Glu Asp Ala
        450                 455                 460
Lys Arg Pro Tyr Phe Thr Val Asp Glu Ala Glu Ala Arg Gln Asp Gly
465                 470                 475                 480
Tyr Gly Asp Arg Thr Leu Gly Tyr Gln Tyr Asp Pro Glu Gln Leu Asp
                485                 490                 495
Leu Ala Glu Asn Met Val Ser Gln Asn Asp Gly Ser Phe Ile Ser Lys
                500                 505                 510
Lys Glu Trp Tyr Val
        515

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer
      PRR2A8

<400> SEQUENCE: 5
agaagcagca gcaccagcag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Primer
      PRR2A9

<400> SEQUENCE: 6
aaggtcacgt tcagccagga                                              20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Primer
      HVEM288

<400> SEQUENCE: 7
atcatatgtg tgaaaagaag a                                            21
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Primer HHVENT03

<400> SEQUENCE: 8
caggttatcg tgtgaaggag                                                20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 9
gcgagatctg cgagttcaag tgcta                                          25

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence:Primer

<400> SEQUENCE: 10
gcgtgatcag tggtgatgat ggtgatgcac cagcggaccc acatctc                  47

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence:Synthetic Peptide; HveB Ectodomain

<400> SEQUENCE: 11

Asp Val Arg Val Gln Val Leu Pro Glu Val Arg Gly Gln Leu Gly Gly
 1               5                  10                  15
Thr Val Glu Leu Pro Cys
            20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:Primer int 1

<400> SEQUENCE: 12
tccttcaccg atggcactat cc                                             22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Primer 108

<400> SEQUENCE: 13
acacgtacca ctccttcttg                                                20

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Primer 104

<400> SEQUENCE: 14
gctctagagc ggctacacgt accactcctt                               30

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer
      pvr01

<400> SEQUENCE: 15
tctggagctt gaagaagtgg g                                        21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Primer pvr07

<400> SEQUENCE: 16
caccttgtgc cctctgtctg                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Primer pvr08

<400> SEQUENCE: 17
cctctcagtc ccgacgctgt                                          20

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 18

Glu Ala Glu Tyr Gln Glu Ile Arg Asn Pro Asn Gly Thr Val
 1               5                  10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 19

Glu Ala Arg Val Pro Gly Asp Ser Gly Thr Pro Met Ala Pro Val
 1               5                  10                  15

<210> SEQ ID NO 20

```
<211> LENGTH: 20
<212> TYPE: DNA
<213> ORGANISM: Artificial Sequence
<220> FEATURE:
<223> OTHER INFORMATION: Description of Artificial Sequence:Primer 105

<400> SEQUENCE: 20
tcaacaccag caggatgctc                                                   20

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 21
gcgtgatcag gtggtccagg tgaacgactc catgtat                                37

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:Primer

<400> SEQUENCE: 22
cggtgatcaa tgatgatgat gatgatgttc gggaggagac ggggtgta                    48

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence:Synthetic
      Peptide; representing AA 155-172 of HveC

<400> SEQUENCE: 23

Ala Val Leu Arg Ala Lys Lys Gly Gln Asp Asp Lys Val Leu Val Ala
 1               5                  10                  15
Thr Cys

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 24
gcgtgatcag gtggtccagg tgaacgactc catgtat                                37

<210> SEQ ID NO 25
<211> LENGTH: 55
<212> TYPE: DNA
<213> ORGANISM: Artificial Sequence
<220> FEATURE:
<223> OTHER INFORMATION: Description of Artificial Sequence:Primer

<400> SEQUENCE: 25
cggcccgggc taatgatgat gatgatgatg ctgcacgttg agagtgaggc tttcc            55

<210> SEQ ID NO 26
<211> LENGTH: 58
<212> TYPE: DNA
<213> ORGANISM: Artificial Sequence
```

-continued

```
<220> FEATURE:
<223> OTHER INFORMATION: Description of Artificial Sequence:Primer

<400> SEQUENCE: 26
cggcccgggc taatgatgat gatgatgatg catcaccgtg agattgagct ggctttct       58
```